(12) United States Patent
Kaouk et al.

(10) Patent No.: US 12,714,389 B2
(45) Date of Patent: Aug. 25, 2026

(54) ULTRASOUND SENSING SYSTEM

(71) Applicant: Method AI, Inc., Cleveland, OH (US)

(72) Inventors: Jad Kaouk, Hunting Valley, OH (US); Charles D. Emery, Gilbert, AZ (US); Douglas Teany, Medfield, MA (US); John-Michael Sungur, Brookline, MA (US); Christopher Lee Laine, Bellingham, MA (US)

(73) Assignee: METHOD AI, INC., Cleveland, OH (US)

( * ) Notice: Subject to any disclaimer, the term of this patent is extended or adjusted under 35 U.S.C. 154(b) by 53 days.

(21) Appl. No.: 18/683,486

(22) PCT Filed: Aug. 11, 2022

(86) PCT No.: PCT/US2022/040128
§ 371 (c)(1),
(2) Date: Feb. 13, 2024

(87) PCT Pub. No.: WO2023/018914
PCT Pub. Date: Feb. 16, 2023

(65) Prior Publication Data

US 2025/0134488 A1 May 1, 2025

Related U.S. Application Data

(60) Provisional application No. 63/332,652, filed on Apr. 19, 2022, provisional application No. 63/232,953, filed on Aug. 13, 2021.

(51) Int. Cl.

| | |
|---|---|
| ***A61B 8/08*** | (2006.01) |
| ***A61B 8/00*** | (2006.01) |
| ***A61B 8/12*** | (2006.01) |

(52) U.S. Cl.
CPC ............. *A61B 8/0841* (2013.01); *A61B 8/12* (2013.01); *A61B 8/4209* (2013.01); *A61B 8/4281* (2013.01); *A61B 8/4477* (2013.01); *A61B 8/54* (2013.01)

(58) Field of Classification Search
None
See application file for complete search history.

(56) References Cited

U.S. PATENT DOCUMENTS

| | | | |
|---|---|---|---|
| 4,375,818 | A | 3/1983 | Suwaki et al. |
| 5,331,947 | A | 7/1994 | Shturman |
| 6,004,269 | A | 12/1999 | Crowley et al. |
| 7,223,239 | B2 | 5/2007 | Schulze et al. |
| 2004/0092821 | A1 | 5/2004 | Hering et al. |

(Continued)

OTHER PUBLICATIONS

International Search Report and Written Opinion for PCT/US2022/040128; mail date Feb. 6, 2023; 11 pages.

*Primary Examiner* — Keith M Raymond
*Assistant Examiner* — Ashish S. Jasani
(74) *Attorney, Agent, or Firm* — RATHE LINDENBAUM LLP

(57) ABSTRACT

An organ surface ultrasound probe includes a head, a pump and a controller. The head may include a transducer, a housing supporting the transducer and a flexible bladder containing an acoustic coupling medium for positioning between the transducer and the exterior surface of the organ. The controller is to output control signals causing the pump to inflate the bladder to different inflation states.

9 Claims, 21 Drawing Sheets

(56) References Cited

U.S. PATENT DOCUMENTS

| | | | | |
|---|---|---|---|---|
| 2004/0210136 | A1 | 10/2004 | Varghese et al. | |
| 2005/0261586 | A1* | 11/2005 | Makin | A61B 8/546 600/459 |
| 2013/0226040 | A1* | 8/2013 | Michael | A61B 8/4488 601/2 |
| 2016/0030773 | A1 | 2/2016 | Burdette et al. | |
| 2016/0206373 | A1* | 7/2016 | Chen | A61B 5/0084 |
| 2016/0249859 | A1 | 9/2016 | Babkin et al. | |
| 2016/0374710 | A1* | 12/2016 | Sinelnikov | A61B 17/3207 600/439 |
| 2017/0105792 | A1* | 4/2017 | Barnes | A61B 18/14 |
| 2020/0297412 | A1* | 9/2020 | Maini | A61B 8/12 |
| 2021/0085384 | A1* | 3/2021 | Maini | A61B 18/1477 |
| 2022/0233209 | A1* | 7/2022 | Borody | A61B 1/015 |

* cited by examiner

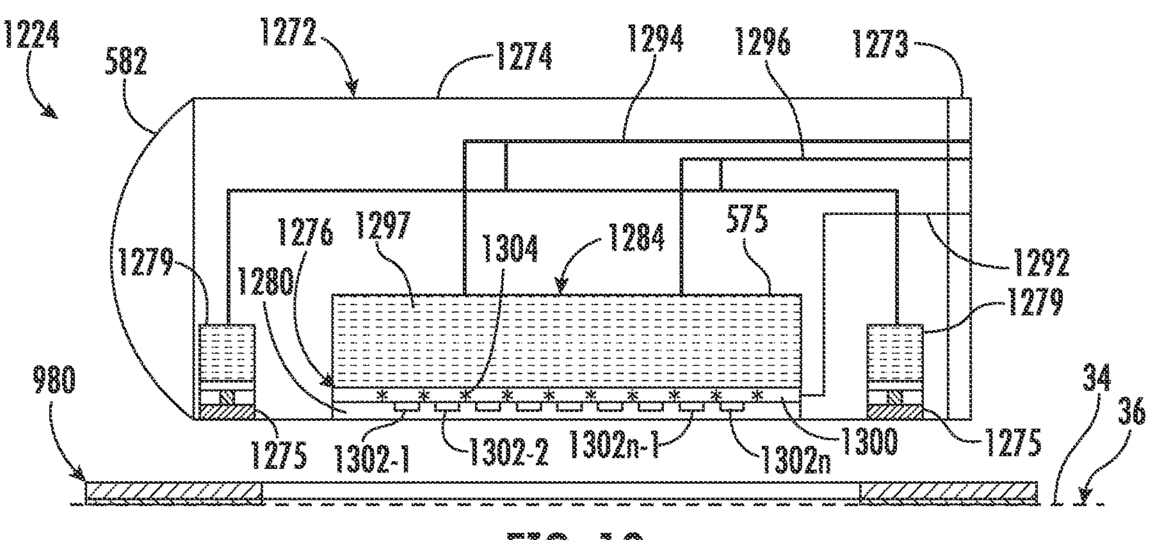
FIG. 19
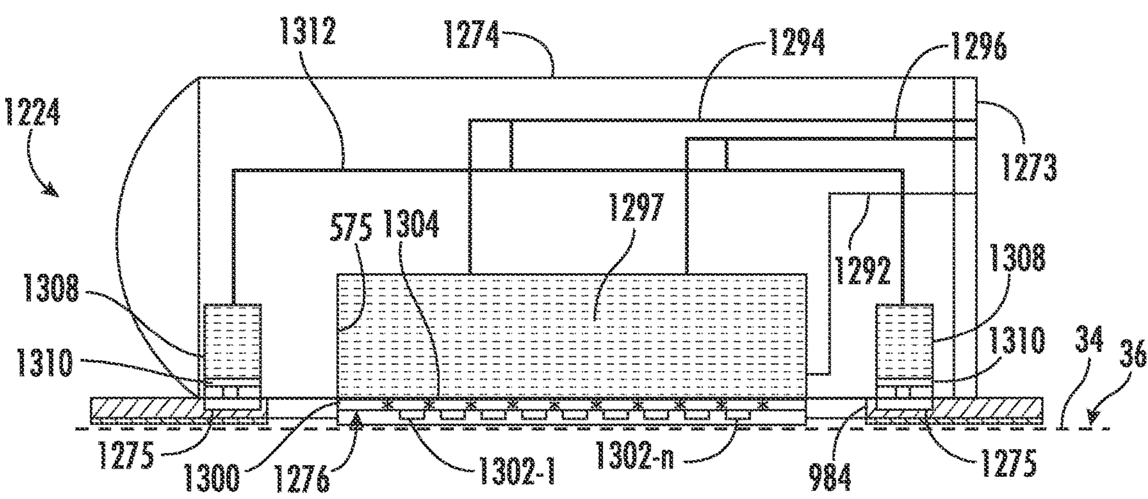
FIG. 20
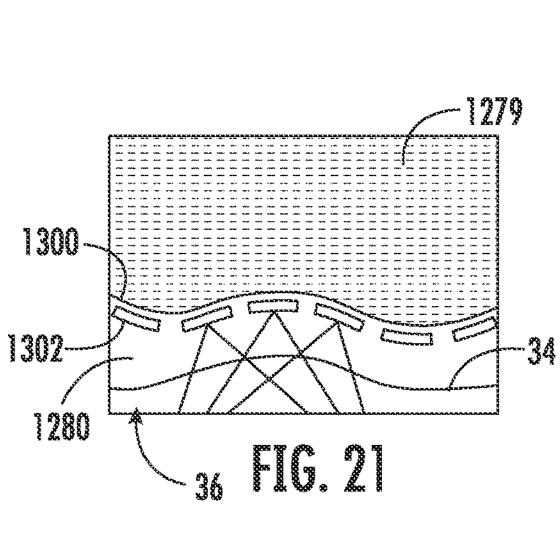
FIG. 21
FIG. 22
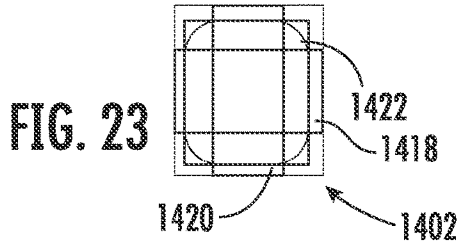
FIG. 23

1835
260
1824
1820
1862
1826
1924
2024
1832-1
33
1832-2
1876
1876
599
599
1880
1880
1833-1
1833-2
1835
1830
33
A
a 260
1820
1862
1835-1
1835-2
1830
1832-1
1832-2
1924
584
A1
A2
1739
2042
1876
1876
2024
1840-1
1840-2
34
36
276
1080
599
1880
1835
599
1880
A
a

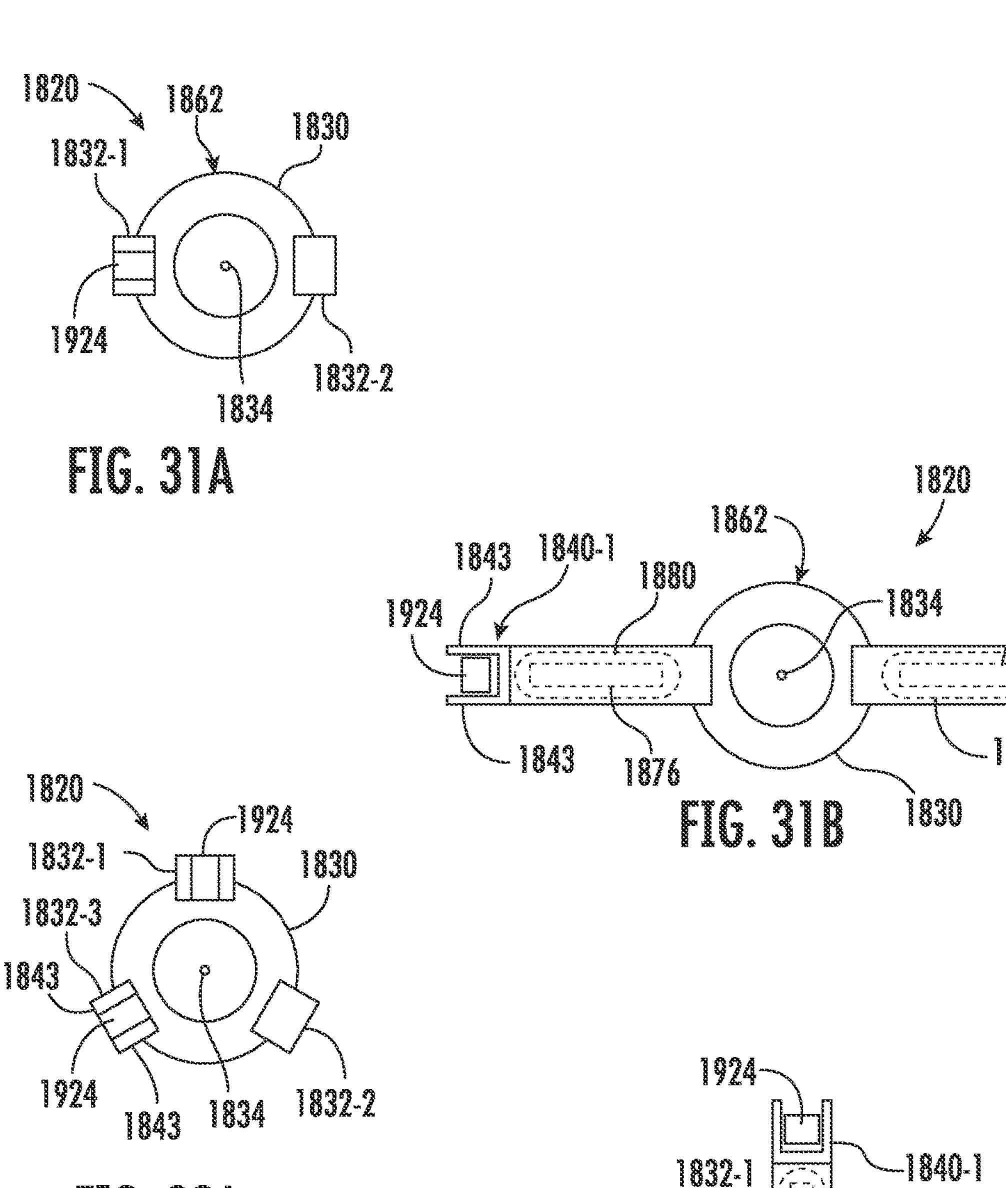
FIG. 31A
FIG. 31B
FIG. 32A
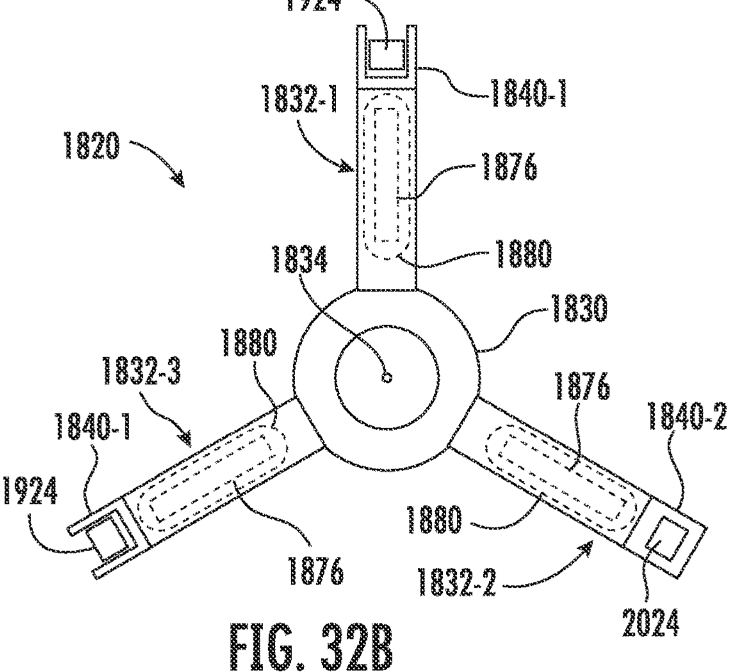
FIG. 32B

ULTRASOUND SENSING SYSTEM

This application claims the benefit of U.S. Provisional Patent Application No. 63/232,953, filed Aug. 13, 2021, entitled ULTRASOUND PROBE FOR MONITORING TISSUE DEFORMATION, and claims the benefit of U.S. Provisional Patent Application No. 63/332,652, filed Apr. 19, 2022, entitled ULTRASOUND SENSING SYSTEM, the disclosures of which are incorporated herein by reference in their entireties.

BACKGROUND

Medical procedures, such as surgeries, sometimes involve the positioning and manipulation of a tool or effector within an organ of a patient. Precise and accurate positioning of the tool often presents a challenge. Interactions of the tool with the organ may displace or move portions of the organ, demanding real-time tool positioning and operation adjustments.

BRIEF DESCRIPTION OF THE DRAWINGS

FIG. 19 is a sectional view schematically illustrating portions of an example organ surface ultrasound probe with a sensing head disconnected from an organ conformable panel and with an acoustic coupler retracted within the sensing head.

FIG. 20 is a sectional view schematically illustrating the portions of the example organ surface ultrasound probe of FIG. 19 with the sensing head connected to the organ conformable panel and with the acoustic coupler projecting from the sensing head through the organ conformable panel.

FIG. 21 is an enlarged sectional view illustrating portions of the example organ surface ultrasound probe of FIG. 20 in contact with an organ surface.

FIG. 22 is a sectional view illustrating portions of an example conformable transducer for use in the organ surface ultrasound probe of FIG. 19.

FIG. 23 is a top view of portions of the example conformable transducer of FIG. 22.

FIG. 31A is a top view of the example ultrasound sensing system of FIG. 29.

FIG. 31B is a top view of the example ultrasound sensing system of FIG. 30.

FIG. 32A is a top view illustrating portions of an example ultrasound sensing system with an example sensing head having wings in a retracted state.

FIG. 32B is a top view illustrating portions of the example ultrasound sensing system of FIG. 32A with the wings and an extended state.

Figure 1:
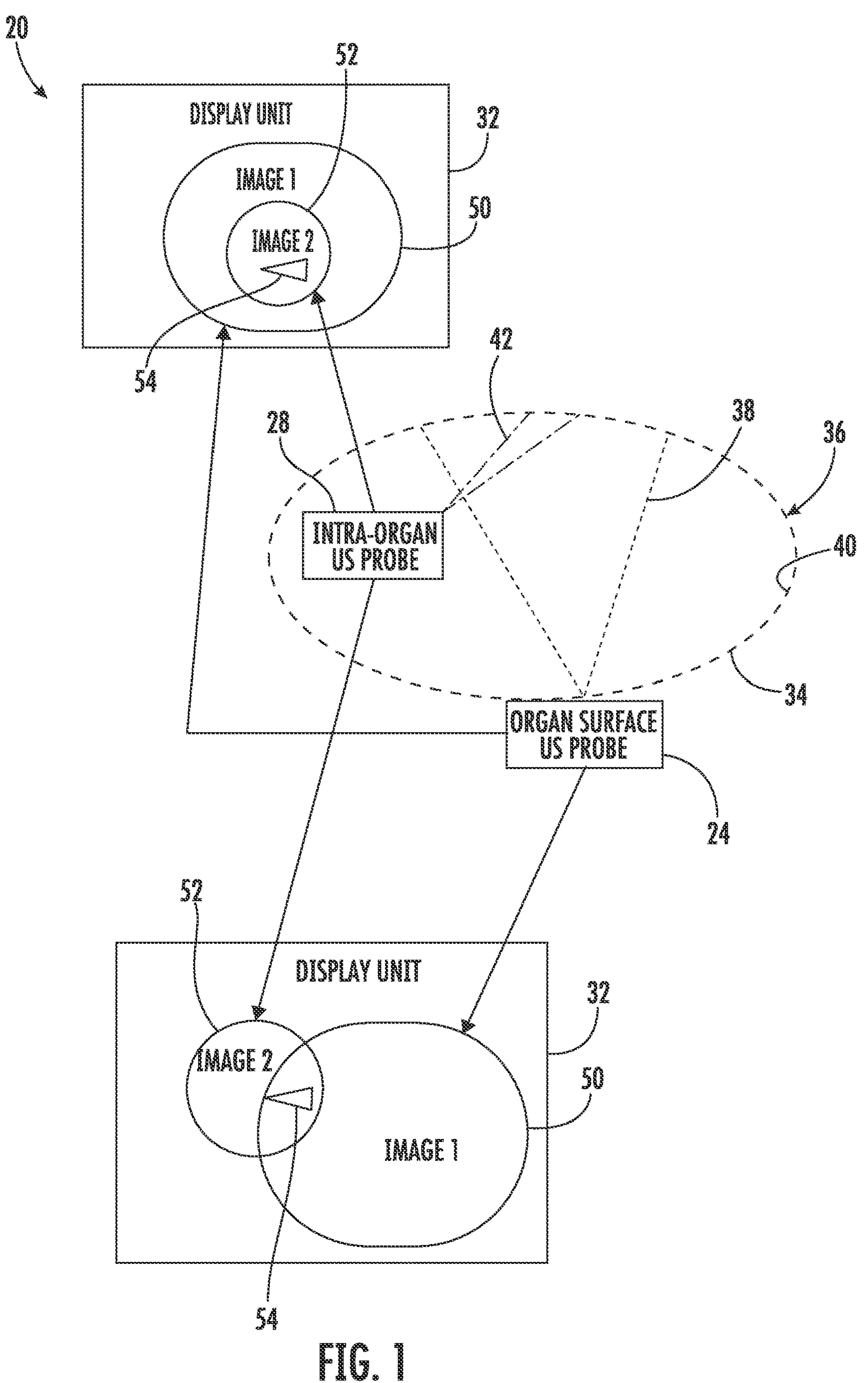
FIG. 1 is a diagram schematically illustrating an example ultrasound sensing system.

Throughout the drawings, identical reference numbers designate similar, but not necessarily identical, elements. The figures are not necessarily to scale, and the size of some parts may be exaggerated to more clearly illustrate the example shown. Moreover, the drawings provide examples and/or implementations consistent with the description; however, the description is not limited to the examples and/or implementations provided in the drawings.

DETAILED DESCRIPTION OF EXAMPLES

Disclosed are example ultrasound sensing systems that facilitate real-time monitoring of interior portions of an organ of a patient while a medical procedure is being performed on the organ. The example ultrasound sensing systems monitor a target tissue of an organ, such as a tumor, in relation to a surgical tool where the localization of the target tissue relative to the surgical tool may be accomplished using the ultrasound images or the ultrasound images and other sensitive data to mathematically describe the position of the target tissue relative to the surgical tool. As a result, such example ultrasound sensing systems may facilitate more precise and accurate positioning of a tool within the organ relative to the target tissue, compensating for movement of the tool/organ, such as movement caused by interaction of the tool with the organ or movement resulting from involuntary respiration.

In some implementations, the example ultrasound sensing systems monitor the target tissue of the organ using multiple ultrasound probes in conjunction with one another, such as a first ultrasound probe comprising an organ surface ultrasound probe and a second ultrasound probe which is positioned closed to a region of interest of the organ (such as a tumor) than the first ultrasound probe. In some implementations, the second ultrasound probe comprises an intra-organ ultra-sound probe. In some implementations, the second ultrasound probe comprises a second organ surface ultrasound probe. In some implementations, the second ultrasound probe comprises a micro-transducer. In some implementations, the example ultrasound sensing systems monitor the target tissue using a single ultrasound probe, such as an organ surface ultrasound probe.

The ultrasonic probes discussed herein may be configured for doppler ultrasound, 2D, 3D ultrasound, stereoscopic ultrasound, elastography and other known ultrasound technologies. In one implementation the ultrasonic probes are configured to provide a combination of doppler and other ultrasound images.

In some implementations, a processing unit, following instructions contained in a non-transitory computer-readable medium, receives ultrasound data from each of the two ultrasound probes and registers or superimposes such data. For example, ultrasound data values from each of the two sensors may be assigned or aligned to the same physical location. In some implementations, the processing unit receives such ultrasound data and processes such ultrasound data to superimpose the ultrasound data in real-time. In some implementations, the receipt and registration of particular ultrasound data by the processing unit may not be in real-time. Such registration of ultrasound data may assist a control or other device to carry out surgical automation or robotic surgery. In some implementations, the registered ultrasound data from the two ultrasound probes is not displayed but is used and manipulated by a control system for controlling automated surgery and/or for providing instruction or recommendations to a medical practitioner performing surgery. In some implementations, the superimposed and/or registered ultrasound data may be communicated to a display unit which uses the registered ultrasound data to generate and display superimposed and registered ultrasound images for viewing by a medical practitioner or other person.

In some implementations, the first and/or second ultrasound probes may operate in different modes depending upon where the ultrasound energy is being focused. For example, in circumstances where the ultrasound probe is focusing its energy on a region which is to be surgically removed, a controller may increase the intensity of the ultrasound energy to a level above or exceeding existing Food and Drug Administration (FDA) guidelines for exposure levels for healthy tissue. Because the tissue receiving the otherwise excessive ultrasound output exposure levels is designated for removal, any risk of damage to such tissue caused by excessive acoustic output exposure levels is not relevant and disregarded. Because the ultrasound probe is operated at a higher intensity in the focused upon area of the organ, which is to be removed, the penetration of the ultrasound waves into the tissue may be deeper and the images generated or derived from such ultrasound waves may have a greater resolution.

The example ultrasound sensing systems may utilize both an organ surface ultrasound probe connected to an exterior surface of an organ and an intra-organ ultrasound probe inserted the organ surface ultrasound probe has a first field-of-view and the intra-organ ultrasound probe has a second field-of-view less than the first field-of-view. A display unit superimposes and registers a first image based upon output of the organ surface ultrasound probe and a second image based upon output of the intra-organ ultrasound probe. In some implementations, the display unit partially overlays or registers the first image and the second image. In some implementations, the registration of the first and second images may be part of a much larger scheme that registers not only ultrasound images, but also optical data, such as images captured by cameras or endoscopic devices.

Disclosed are example ultrasound sensing systems that may be operated by controller such that the acoustic field emission of the organ surface ultrasound probe or the intra-organ ultrasound probe is focused on the tissue identified or designated for surgical removal and has an output exposure level exceeding the FDA acoustic output exposure level guidelines for the organ or particular procedure. Because the tissue receiving the otherwise excessive ultrasound output exposure levels is designated for removal, any risk of damage to such tissue caused by excessive acoustic output exposure levels is not relevant and disregarded. Because the organ surface ultrasound probe and/or the intra-organ ultrasound probe is operated at a higher intensity in the focused upon area of the organ, which is to be removed, the penetration of the ultrasound waves into the tissue may be deeper and the images generated or derived from such ultrasound waves may have a greater resolution.

Disclosed are example organ surface ultrasound probes. The example organ surface ultrasound probes are to be supported along an exterior surface of a patient's organ. In some implementations, the example organ surface ultrasound probes may be used independent of any intra-organ ultrasound probe. For example, in some implementations, the example organ surface ultrasound probes may provide a full region of interest or volume for monitoring the manipulation and positioning of a surgical tool. In implementations where the example organ surface ultrasound probe is used in conjunction with an intra-organ ultrasound probe, the organ surface ultrasound probe may provide cross-sectional or volume ultrasound imaging. In such implementations, the image provided by the organ surface ultrasound probe need not necessarily be real time, whereas the image provided by the intra-organ ultrasound probe is real-time. In some implementations, the image or ultrasound data provided by the intra-organ ultrasound probe is not in real-time. The example organ surface ultrasound probes utilize a transducer that is acoustically coupled to the exterior surface of the organ by an acoustic coupler. In such implementations, the acquisition and display rate may be based upon or a result of surgical speed and any requirements for tracking and registration.

In some implementations, the organ surface ultrasound probes are inserted within the patient using an insertion shaft which may pass through a tube or trocar. The insertion shaft may be pivotally coupled to a head of the probe which supports the transducer and the acoustic coupler. In some implementations, the insertion shaft includes multiple segments which are pivotable relative to one another. In yet other implementations, the head of the probe is itself directly pivotally connected to the insertion shaft.

In some implementations, the insertion shaft may be separable or removable from the head, permitting the head of the probe to remain adjacent to or secured to the exterior surface of the organ and permitting the insertion shaft to be withdrawn. In some implementations, the insertion shaft is configured to be selectively reattached to the head as desired. In some implementations, the transducer and other components of the probe head may communicate with an external control system via electrical cables and/or fluid tubes which extend along and are coupled to the insertion shaft. In some implementations, such cables and/or fluid tubes are releasably connected to the insertion shaft, permitting withdrawal of the insertion shaft while maintaining a connection between the cables and/or fluid tubes and the head of the probe while the head of the probe remains secured to the exterior surface of the organ. In some implementations, the insertion shaft may be omitted where the head of the probe is inserted into the patient and positioned adjacent to the exterior surface of the organ using separate positioning tools. In open surgery, the head of the probe may be directly positioned upon the exterior surface of the organ to be monitored.

In some implementations, the transducer and the acoustic coupler are supported and housed within a head of the probe. The transducer and the acoustic coupler are retracted into the housing or head of the probe during insertion of the probe into the body of the patient. Once the probe has been properly inserted and positioned, the acoustic coupler may be moved, extended or enlarged so as to project beyond the housing into conformable contact with the exterior surface of the organ.

The example organ surface ultrasound probes may retain the acoustic coupler in conformable contact with the exterior surface of the organ in various manners. Because the example organ surface ultrasound probes are generally affixed to the organ of interest, the example probes provide a "set it and forget it" functionality wherein the probe and its transducer positioned on the organ of interest are fixed through duration of a medical or surgical procedure without support from a secondary ultrasound transducer. The position of the probe and its transducer on the organ of interest may be fixed at a location and orientation such that the imaging or visualization of the target tissue, such as the tumor, and region of interest in the organ, are optimized through duration of the medical or surgical procedure.

In some implementations, an adhesive layer on the acoustic coupler is used to secure and retain the acoustic coupler to the exterior surface of the organ. In some implementations, an adhesive layer provided on the housing of the probe adheres to the exterior surface of the organ and retains the acoustic coupler relative to the organ. In some implementations, the housing of the probe may include grippers configured to grip the exterior surface of the organ in regions of the organ about the acoustic coupler. In some implementations, the grippers may include vacuum cups. In some implementations, the vacuum cups may rely on passive vacuum. In some implementations, the vacuum cups are connected to a vacuum source for selectively generating suction or a vacuum to selectively grip the exterior surface of the organ.

In some implementations, a conformable panel is first adhered or otherwise secured to the exterior surface of the organ. The conformable panel may include a window or aperture and may extend into conformable contact with the exterior surface of the organ The conformable panel serves as a landing pad for the housing of the probe. The housing of the probe is mountable to the conformable panel over or adjacent the window or aperture. In some implementations, the housing of the probe is adhesively bonded to the conformable panel. In some implementations, the probe may include couplers for permanently or releasably coupling the housing of the probe to the conformable panel. Such couplers may utilize a snap fit, a press fit or other mechanical releasable connections to the conformable panel. In some implementations, the couplers are movable between retracted positions in which the couplers are at least partially retracted or recessed within the probe housing, such as for insertion of the probe into the patient, and extended positions beyond the housing in coupling engagement with the conformable panel.

In some implementations, the transducer is generally fixed in both position and orientation, emitting mechanical waves in directions perpendicular to a longitudinal axis of the head. In some implementations, the transducer is pivotably coupled to the head and/or translatable relative to the head, permitting the orientation and the positioning of the transducer to vary depending upon the profile or topography of the exterior surface of the organ. In some implementations, the positioning/extension/retraction and/or orientation/angle of the transducer is controllable independent of the topography of the exterior surface of the organ, permitting a direction and/or depth of the field-of-view of the transducer to be varied and controlled. In some implementations, the housing of the probe supports an actuator for altering the positioning and/or orientation of the transducer relative to the housing and, in some implementations, relative to the acoustic coupler. In some implementations, portions of the actuator used to adjust the positioning and/or orientation of the transducer may be located external to the head of the probe, communicating with the head of the probe through a cable and/or fluid line connected to the head.

In particular implementations, the transducer may comprise a conformable transducer. One example conformable transducer may include a flexible substrate that supports an array of individual transducer elements. In some implementations, the flexible substrate may further support sensors for detecting flexing or bending of the flexible substrate which may correlate to the angular positions of the individual transducer elements. One example of such a sensor is a strain sensor mounted to or formed as part of the flexible substrate. Signals from the transducers and from the sensors in or on the flexible substrate may be communicated to a local or remote control using electrical lines supported upon or embedded within the flexible substrate.

In some implementations, the organ surface ultrasound probe may include individual actuators that selectively move portions of the flexible substrate to flex or bend portions of the flexible substrate and control the steering or direction of the individual transducer elements. As a result, individual transducer elements may be steered and/or focused in a desired direction. In some implementations, the individual actuators may comprise piezoelectric or piezo-resistive actuators or PZT bimorphs spaced along the flexible substrate to individually move respective portions of the substrate and to individually steer associated transducer elements of the conformable transducer.

In some implementations, the acoustic coupler comprises a bladder containing a fluid. In some implementations, the bladder is connected to a fluid line and a fluid pump which selectively inflate and deflate the bladder to move the acoustic coupler between a retracted position in which the acoustic coupler is retracted or recessed within a housing of the probe and an extended position beyond the housing of the probe in which the acoustic coupler is in conformable contact with the exterior surface of the organ. In some implementations, the pressure of the fluid within the bladder may be directly or indirectly monitored with a pressure sensor or multiple pressure sensors. Indirect sensing of the pressure within the bladder may be achieved using a pressure sensor external to the bladder and along the fluid line. The pressure of the fluid within the bladder may be used to determine an extent to which the bladder has been inflated and/or degree to which the bladder (the acoustic coupler) is being pressed against the exterior surface of the organ. In some implementations, the bladder may be inflated to a pressure that exceeds a predefined threshold which correlates to a target amount of pressure being exerted by the bladder against the exterior surface of the organ. In some implementations, an external sensor, such as an external ultrasound sensor, positioned on the exterior anatomy of the patient, may be used to determine when the acoustic coupler of the probe is against and in acoustic contact with the surface of the organ.

In some implementations, the transducer is at least partially immersed within the fluid. In such implementations, the bladder may be connected to a fluid inlet line and a fluid outlet line would supply fluid into the interior of the bladder and draw fluid from the interior of the bladder. As a result, fluid may be circulated through and across the bladder and across the transducer to cool the transducer and surrounding portions of the probe. Cooling the transducer may reduce the likelihood of damage to the transducer caused by overheating and/or may reduce the risk of the probe becoming too warm or hot while within the patient.

In some implementations, the temperature of the transducer is directly or indirectly monitored using a sensor or multiple sensors. The temperature of the sensor may be indirectly monitored using sensors that sense the temperature of the fluid within the bladder or the fluid circulating within the probe or external to the probe. The sensed temperature may be used to control the rate at which fluid is circulated through the bladder and/or the temperature of the fluid being circulated. For example, in some implementations, the fluid may be circulated through a passive heat extractor, such as a heat sink. In some implementations, an active heat extractor, such as a fan or Peltier device may be used to further extract heat from the passive heat extractor to further reduce the temperature of the circulating fluid.

In some implementations, the transducer is not at least partially submersed within a fluid serving as the acoustic coupler, but instead abuts a face of the acoustic coupler. In such implementations, an actuator may be used to translate the transducer which in turn moves the acoustic coupler. The acoustic coupler may be moved from a retracted state within the housing to an extended state beyond the housing and in conformable contact with an organ by using an actuator to translate the position of the transducer.

In particular implementations, much of the control over the head of the organ surface ultrasound probe is carried out with an external probe control system. For purposes of this disclosure, the term "external" refers to the relationship of the component or system with respect to the patient. In this case, the external probe control system is located external to the anatomy or body of the patient. The external probe control system communicates with the various components of the head of the probe using and cables (wires or bundles of wires) and/or fluid lines/tubes which extend into the body of the patient to the head of the probe which is adjacent to the exterior surface of the organ. As discussed above, such cables and/or fluid lines may remain attached to the head even after separation of the head from the tool used to position and insert the head. In some implementations, such cables for communicating with the transducer or sensors located on the head may be omitted where the sensing head is configured to wirelessly communicate with the external probe control system.

In some implementations, at least portions of the control over the functions of the head may be carried out using components locally located on the head. For example, the head itself may locally house or support actuators, pumps, and/or fluid reservoirs (for inflating/deflating the bladder of an acoustic coupler). In some implementations, the head of the probe may house or support a local controller or processing unit for controlling certain operations of the head. Such a controller/processing unit may be in the form of an integrated circuit, such as an application-specific integrated circuit or a field programmable gate array.

Disclosed are example intra-organ ultrasound probes for use in the described example ultrasound sensing systems or for use in other ultrasound sensing systems. The example intra-organ ultrasound probes may have a sensing head that is selectively movable relative to an insertion shaft used to position the probe into and within an interior of an organ. In some implementations, the sensing head is removably coupled to the insertion shaft for separation from the insertion shaft while within the organ. In some implementations, the head may be magnetically coupled to the insertion shaft.

In some implementations, the insertion shaft may have an adjustable length. For example, in some implementations, the insertion shaft may be telescopic. In some implementations, the insertion shaft may comprise a plurality of segments, wherein each segment is movable relative to other segments. The insertion shaft may include a plurality of markings to facilitate detection by an organ surface ultrasound probe.

In particular examples, the intra-organ ultrasound probe has a tip that includes a sensor to detect engagement of the tip with soft tissue. In some implementations, the tip may comprise a sharp transparent lens for soft tissue puncturing and a forward sensor rearward the sharp lens which has a field-of-view through the transparent lens. In some implementations, the probe extends along an axis, wherein a transducer of the probe is configured to sense in a direction transverse to the axis. In some implementations, the transducer may be selectively movable relative to a remainder of the head by an actuator. In some implementations, the tip of the probe may be elastomeric and/or blunt.

For purposes of this application, the term "processing unit" shall mean a presently developed or future developed computing hardware that executes sequences of instructions contained in a non-transitory memory. Execution of the sequences of instructions causes the processing unit to perform steps such as generating control signals. The instructions may be loaded in a random-access memory (RAM) for execution by the processing unit from a read only memory (ROM), a mass storage device, or some other persistent storage. In other embodiments, hard wired circuitry may be used in place of or in combination with software instructions to implement the functions described. For example, a controller may be embodied as part of one or more application-specific integrated circuits (ASICs). Unless otherwise specifically noted, the controller is not limited to any specific combination of hardware circuitry and software, nor to any particular source for the instructions executed by the processing unit.

For purposes of this disclosure, the term "coupled" shall mean the joining of two members directly or indirectly to one another. Such joining may be stationary in nature or movable in nature. Such joining may be achieved with the two members, or the two members and any additional intermediate members being integrally formed as a single unitary body with one another or with the two members or the two members and any additional intermediate member being attached to one another. Such joining may be permanent in nature or alternatively may be removable or releasable in nature. The term "operably coupled" shall mean that two members are directly or indirectly joined such that motion may be transmitted from one member to the other member directly or via intermediate members. The term "fluidly coupled" shall mean that two or more fluid transmitting volumes are connected directly to one another or are connected to one another by intermediate volumes or spaces such that fluid may flow from one volume into the other volume.

For purposes of this disclosure, the phrase "configured to" denotes an actual state of configuration that fundamentally ties the stated function/use to the physical characteristics of the feature proceeding the phrase "configured to".

For purposes of this disclosure, the term "releasably" or "removably" with respect to an attachment or coupling of two structures means that the two structures may be repeatedly connected and disconnected to and from one another without material damage to either of the two structures or their functioning.

For purposes of this disclosure, unless explicitly recited to the contrary, the determination of something "based on" or "based upon" certain information or factors means that the determination is made as a result of or using at least such information or factors; it does not necessarily mean that the determination is made solely using such information or factors. For purposes of this disclosure, unless explicitly recited to the contrary, an action or response "based on" or "based upon" certain information or factors means that the action is in response to or as a result of such information or factors; it does not necessarily mean that the action results solely in response to such information or factors.

Ultrasound Sensing Systems

FIG. 1 is a diagram schematically illustrating one example ultrasound sensing system 20. System 20 facilitates real-time monitoring of interior portions of an organ of a patient while a medical procedure is being performed on the organ. System 20 further facilitates more precise and accurate positioning of devices within the patient such as an intra-organ ultrasound probe, and organ surface ultrasound probe and any surgical tools. System 20 facilitates compensating for movement of the organ, such as movement caused by interaction of such devices with the organ. System 20 comprises organ surface ultrasound probe 24, intra-organ ultrasound probe 28 and display unit 32.

Organ surface ultrasound probe 24 is configured to connect to an exterior surface 34 of an organ 36. In some implementations, system 20 uses elastography data to direct a robotic arm to position ultrasound probe 24 against the organ with sufficient pressure to maintain the position of ultrasound probe 120 against an outer surface of the patient's organ or against another features of interest. The feedback during a surgical procedure from the elastography data to a robotic system can maintain ultrasound probe 24 affixed to the patient's organ. Organ surface ultrasound probe 24 has a first field-of-view 38. Signals from organ surface ultrasound probe 24 are transmitted to display unit 32 for the generation of an ultrasound image depicting an interior surface of organ 36.

Intra-organ ultrasound probe 28 is configured to be inserted into an interior 40 of organ 36. Intra-organ ultrasound probe 28 has a second field-of-view 42 less than the first field-of-view 38. The field-of-view 42 may be at least partially contained within the larger field-of-view 38 of the organ surface ultrasound probe 24. In one implementation ultrasound probe 24 and ultrasound probe 28 include any combination of one or more of ultrasound sensors, doppler sensors and elastography sensors.

Display unit 32 receives signals from organ surface ultrasound probe 24 and intra-organ ultrasound probe 28. Display unit 32 may include a monitor or display screen and a processing unit that follows instructions contained in a non-transitory computer-readable medium so as to generate and display images on the display screen based upon the signals received from probes 24 and 28. FIG. 1 illustrates two example image display scenarios. As shown at the top of FIG. 1, display unit 32 may concurrently display a first image 50 based upon signals from organ surface ultrasound probe 24 and a second image 52 based upon signals from intra-organ ultrasound probe 28. Images 50 and 52 are co-registered, wherein image 52 is contained within image 50. In some implementations, image 50 has a first resolution, whereas image 52 has a second resolution greater or otherwise better than the first resolution.

In the example illustrated, display unit 32 may also depict an effector/tool 54 on at least one of images 50 and 52. The depicted effector 54 may be generated based upon signals from probe 24 and/or 28 while an actual effector 54 is within the respective field of views. In some implementations, the depicted effector 54 may be digitally generated and may represent a target positioning or location for an actual effector. In some implementations, display unit 32 may depict multiple effectors, a first effector corresponding to the positioning of an actual effector within the field-of-view of one or both of probes 24, 28 and a second effector being digitally generated and corresponding to a targeted positioning for the actual effector. In such an implementation, an operator may be guided to move the actual effector within the field-of-view(s) to a position in which the actual effector overlaps the generated effector target position. In some implementations, the target position may be depicted on the image using other graphics such as a bull's-eye or the like.

In some implementations, the angle and size or location of the effector tool may be projected onto the image without actually being within the image. For example, the angle or view of the image being presented may be based upon or correspond to the current positioning and angle of approach of the effector tool without the effector tool being visually depicted. In one sense, the display unit 32 may depict images that correspond to a hypothetical view of the effector tool as it is moving within the organ.

The bottom of FIG. 1 illustrates display unit 32 partially registering images 50 and 52, wherein such images partially overlap. In the example illustrated, the effector 54 is depicted within an intersection region of images 50 and 52. Because display unit 32 at least partially registers images 50 and 52 from probe 24 and 28, respectively, a medical practitioner or other operator may view larger surrounding region of interest depicted by image 50 and may concurrently view a potentially more detailed image 52 of a region of the organ where the medical procedure is to be carried out.

In some implementations, the organ surface ultrasound probe 24 may emit mechanical waves at a first frequency, whereas the intra-organ ultrasound probe emits mechanical waves at a second frequency greater than the first frequency. In some implementations, the first image 50, based upon signals from organ surface ultrasound probe 24, has a first resolution, whereas the second image 52, based upon signals from intra-organ ultrasound probe 28, the second resolution being greater (finer) than or otherwise better than the first resolution. In some implementations, the organ surface ultrasound probe has a first depth of view, whereas the intra-organ ultrasound probe 28 has a second depth of view less than the first depth of view.

Figures 2, 3A:
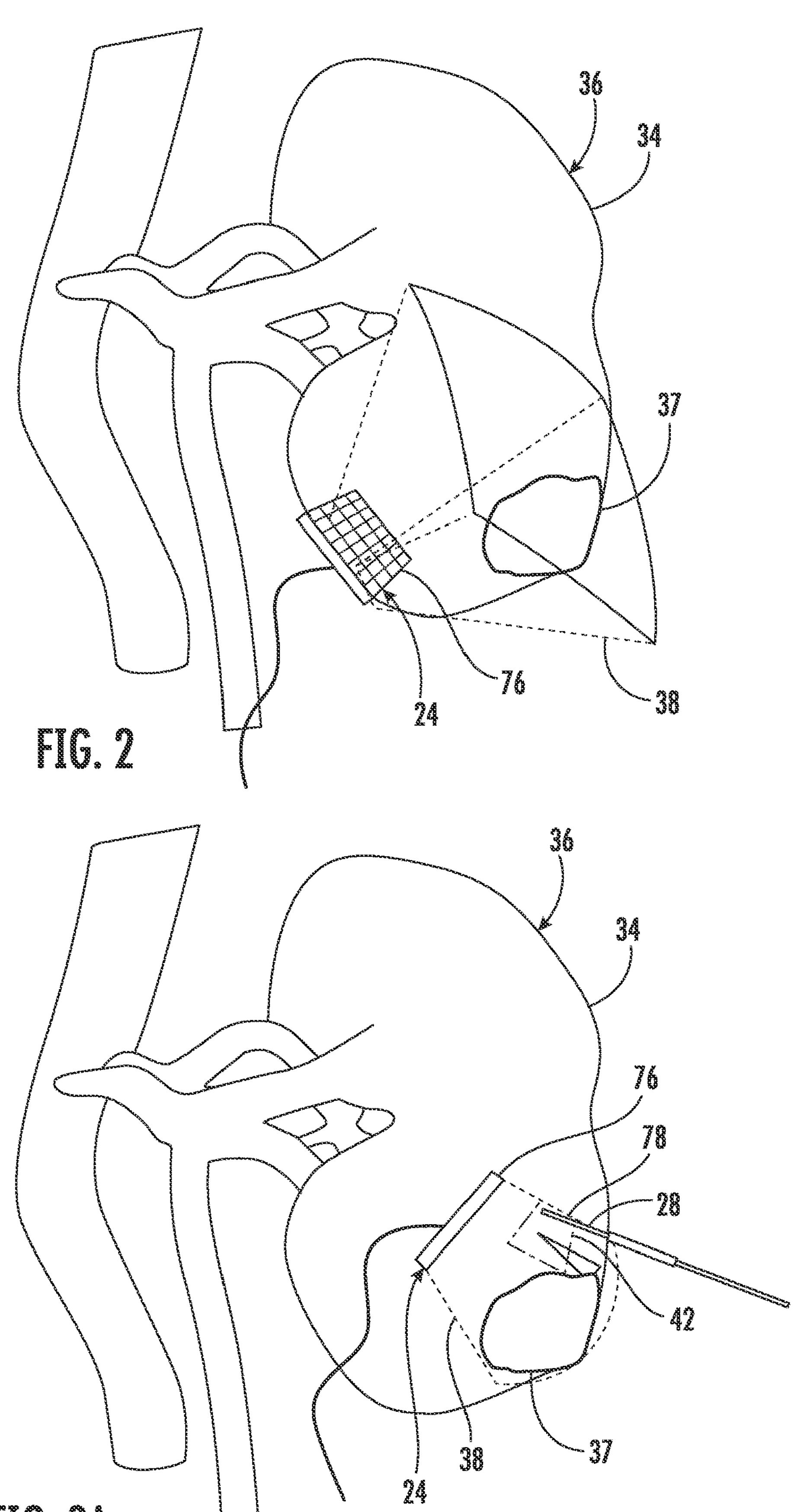
FIG. 2 is a perspective view illustrating one example position of an example organ surface ultrasound probe transducer on a surface of an example organ.
FIG. 3A is a perspective view illustrating one example position of an example organ surface ultrasound probe on a surface of an example organ and an example intra-organ ultrasound probe within the example organ.

FIG. 2 illustrates one example of the positioning of an example transducer 76 of organ surface ultrasound probe 24 secured or affixed to an organ 36 (shown as a kidney) opposite to an example tumor 37 (shown as an endophytic tumor). Transducer 76 has a field-of-view 38 encompassing a three-dimensional volume that may include an entire region of interest, including tumor 37. In the example illustrated, transducer 76 comprises a 2D array or row-column array of transducer elements. Transducer 76 comprises a real-time volume transducer having dimension to facilitate insertion through an access port or trocar. In other implementations, transducer 76 may have other configurations and dimensions.

In the example illustrated, signals from transducer 76 may be used to depict or generate a real-time volumetric image of the tumor 37 as well as nearby vessels and surrounding healthy tissue. The example transducer 76 is affixed and acoustically coupled to the organ 36 opposite to tumor 37. The example transducer 76 is oriented such that the centerline of the ultrasound volume is perpendicular to a midline of the base of the tumor 37. In some implementations, the example transducer 76 is coupled to the exterior surface 34 of organ 36 so as to move with the corresponding movement of the adjacent underlying portions of tumor 36. As a result, transducer 76 and the example organ surface ultrasound probe 24 provide a "set it and forget it" functionality, wherein the example transducer 76 has a fixed position on surface 34 through duration of a surgical or medical procedure, without necessarily requiring support from a secondary ultrasound transducer. In some implementations, a secondary ultrasound transducer may be utilized for further control and/or for monitoring the position of probe 24.

FIG. 3A depicts the organ 36 of FIG. 2 and the organ surface ultrasound probe 24 with transducer 76. FIG. 3A further illustrates the positioning of intra-organ surface ultrasound probe 28 through the exterior surface 34 and into the interior 40 of organ 36. Probe 28 comprises an example transducer 78 which may be in the form of a micro transducer. Transducer 78 has a field-of-view 42 containing those portions of tumor 37 where a medical procedure is to occur. Field-of-view 42 is contained within the larger field-of-view 38 of the example transducer 76. In the example illustrated, transducer 76 has a first depth of view, whereas transducer 78 has a second depth of view less than the first depth of view. In the example illustrated, transducer 76 emits mechanical waves at a first frequency, whereas transducer 78 emits mechanical waves at a second frequency greater than the first frequency. In some implementations, transducer 76 of the organ surface ultrasound probe operates or emits mechanical waves at a frequency of at least 8 MHz and no greater than 20 MHz, transducer 78 of the intra-organ ultrasound probe emits mechanical waves at a frequency of at least 15 MHz and no greater than 35 MHZ. In some implementations, transducer 78 of the intra-organ ultrasound probe emits mechanical waves at a frequency greater than the frequency at which transducer 76 of the surface ultrasound probe emits mechanical waves.

In some implementations, the organ surface ultrasound probe 24 may remain static or stationary, mounted to organ 36, while the second ultrasound probe 28 may move within the organ, wherein such movement may be based upon movement of an effector or cutting tool. In some implementations, the second ultrasound probe 28 may have a field-of-view that encompasses the effector or cutting tool and/or regions of the organ surface just ahead of the effector or cutting tool, regions contain the expectorant dissipated future path of the effector or cutting tool.

As discussed above, signals from transducers 76 and 78 may be transmitted wirelessly or in a wired fashion to display unit 32 (shown in FIG. 1). Display unit 32 uses such signals to build or generate a co-registered picture-in-picture of ultrasound images as the surgery or medical procedure progresses. During the procedure, the portion of the image generated based upon signals from transducer 78 may be refreshed more frequently than the portion of the image generated based upon signals from transducer 76. In some implementations, the image or image portion based upon the signals from transducer 78 may be refreshed on the display screen in real-time, whereas the image or image portion based upon signals from transducer 76 is not necessarily refreshed on the display screen in real-time.

Figures 3B, 3C:
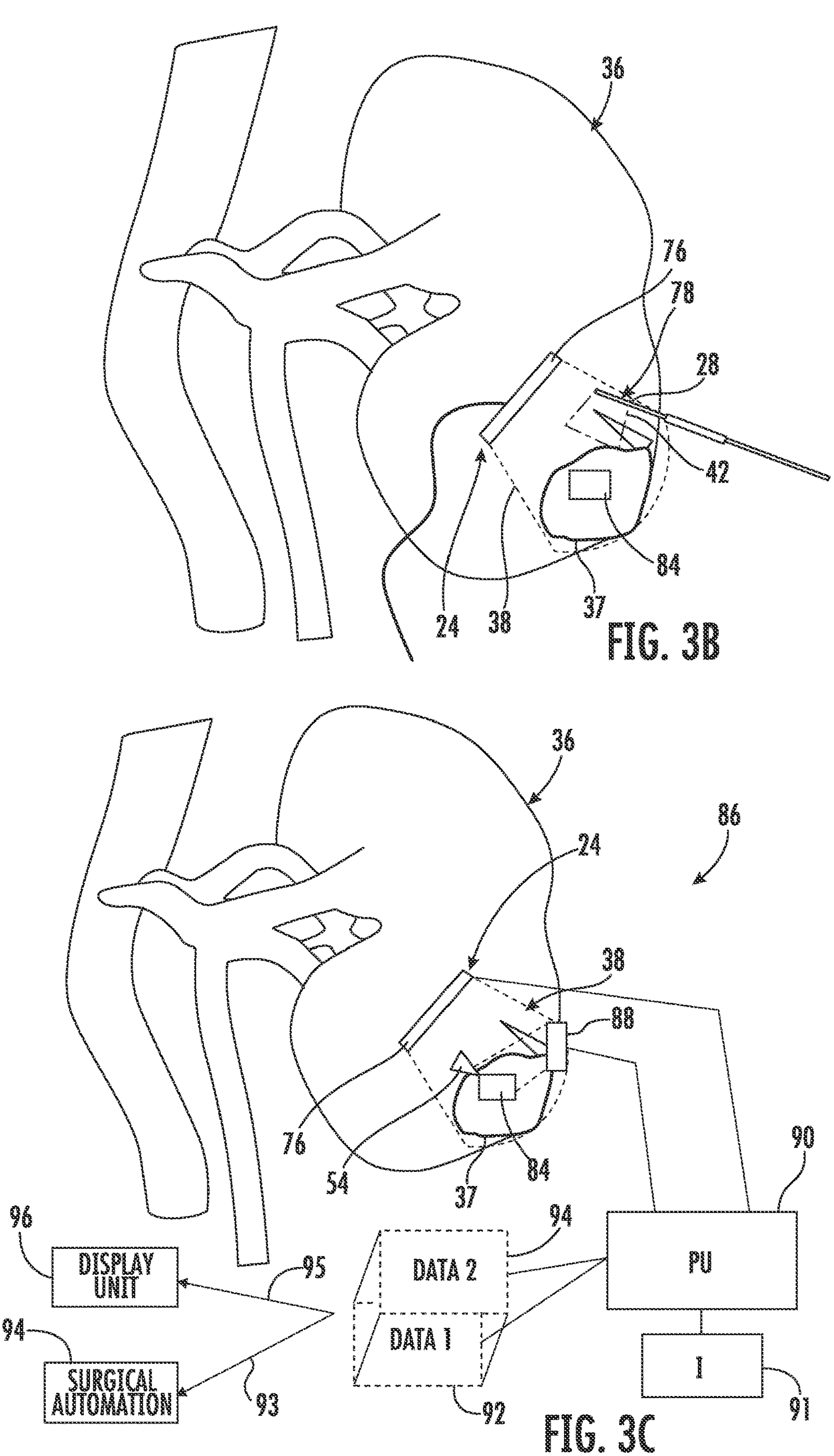
FIG. 3B is a perspective view illustrating an example focus region of either the example organ surface ultrasound probe or the example intra-organ ultrasound probe, the focus region being on an example tumor of an organ which is to be removed.
FIG. 3C is a perspective view illustrating an example ultrasound sensing system.

FIG. 3B illustrates the operation of transducer 76 in distinct modes based upon an area of the organ 36 upon which the ultrasound waves are being focused. The United States Food and Drug Administration (FDA) has guidelines regarding recommended acoustic output exposure levels for different procedures or different types of tissue which are to undergo ultrasound diagnostics. Such guidelines are provided in the following table.

| Use | $I_{SPTA.3}$ (mW/$cm^2$) | $I_{SPPA.3}$ (W/$cm^2$) | or MI |
|---|---|---|---|
| Peripheral Vessel | 720 | 190 | 1.9 |
| Cardiac | 430 | 190 | 1.9 |
| Fetal Imaging & Other[26] | 94 | 190 | 1.9 |
| Ophthalmic | 17 | 28 | 0.23 |

The "Fetal Imaging & Other" category includes abdominal, intraoperative, pediatric, small organ (breast, thyroid, testes, etc.), neonatal cephalic, and adult cephalic use.

The organ surface ultrasound probe 24 may be operated in accordance with such guidelines. However, in some implementations, organ surface ultrasound probe 24 operates outside or beyond such guidelines based upon the particular area or portion of the organ upon which the sound waves are being focused. For example, in some implementations, particular tissue associated with the organ may be designated for surgical removal. In such implementations, organ surface ultrasound probe 24 may be operated by controller such that the acoustic field emission of the organ surface ultrasound probe is focused on the tissue identified or designated for surgical removal and has an exposure level exceeding the FDA acoustic output exposure level guidelines for the organ or particular procedure. Because the tissue receiving the otherwise excessive ultrasound output exposure levels is designated for removal, any risk of damage to such tissue caused by excessive acoustic output exposure levels is not relevant and disregarded. Because the organ surface also probe 24 is operated at a higher intensity in the focused upon area of the organ, which is to be removed, the penetration of the ultrasound waves into the tissue may be deeper and the images generated or derived from such ultrasound waves may have a greater resolution.

In the example illustrated in FIG. 3B, biological tissue of the tumor 37 of organ 36 has been designated for surgical removal. Transducer 76 of organ surface ultrasound probe 24 may be operated in a first mode in compliance with the above noted guidelines when the focus of its ultrasound waves includes healthy tissue, tissue not designated for surgical removal. Transducer 76 of organ surface ultrasound probe 24 may be operated in a second mode having an intensity and output exposure level exceeding the exposure level set forth in the FDA guidelines when the focus of its ultrasound waves is upon tissue designated for removal. The intensity may be measured in terms of a mechanical index, thermal index or any designated parameter as described by a governing body that limits acoustic output. In some implementations, ultrasound probe 24 may be simultaneously or concurrently operated in both the first mode and the second mode, wherein ultrasound probe 24 has multiple concurrent foci, one focus region within healthy tissue, operating under the first mode, and the other focus region within tissue designated for removal, operating under the second mode. In the example illustrated, organ surface ultrasound probe 24 may have ultrasound waves focused on the region or area 84 of the tumor 37 designated for removal, wherein the intensity of such waves result in an output exposure level that exceeds the corresponding exposure level set forth in the FDA guidelines.

In some implementations, the first area of tissue upon which the ultrasound waves are focused during the first mode experiences an exposure level of less than or equal to 190 W/$cm^2$ and wherein the second area of tissue, designated for surgical removal, and upon which ultrasound waves are focused, during the second mode experiences and exposure level that exceeds 190 W/$cm^2$. In some implementations, the first area of tissue upon which the ultrasound waves are focused during the first mode experiences an exposure level of less than or equal to 720 mW/$cm^2$ and wherein the second area of tissue, designated for surgical removal, and upon which ultrasound waves are focused, during the second mode experiences and exposure level that exceeds 720 mW/$cm^2$.

In one particular example implementation, organ surface ultrasound probe is controlled in response to control signals received from a medical practitioner via an input device or is automatically controlled by controller so as to carry out a method wherein organ surface ultrasound probe 24 is operated in a first mode within acoustic field emission focused on organ of the patient and having a first output exposure level. When operating in the first mode, the controller or medical practitioner uses images or data signals acquired from the organ surface ultrasound probe to identify tissue associated with the organ for removal. Organ surface ultrasound probe is then operated in a second mode within acoustic field emission focused on the identified tissue, the acoustic field emission having a second output exposure level greater than the first output exposure level. In some implementations, the first exposure level of less than or equal to 190 W/cm$^2$ and the second exposure level exceeds 190 W/cm$^2$. In some implementations, the first exposure level is less than or equal to 720 mW/cm$^2$ and wherein the second exposure level that exceeds 720 mW/cm$^2$.

In some implementations, the intra-organ ultrasound probe 28 also be operated in distinct modes based upon an area of the organ 36 upon which the ultrasound waves are being focused. In the example illustrated in FIG. 3B, biological tissue of the tumor 37 of organ 36 has been designated for surgical removal. Transducer 78 of intra-organ ultrasound probe 28 may be operated in a first mode in compliance with the above noted guidelines when the focus of its ultrasound waves includes healthy tissue, tissue not designated for surgical removal. Transducer 78 of intra-organ ultrasound probe 28 may be operated in a second mode having an intensity and output exposure level exceeding the exposure level set forth in the FDA guidelines when the focus of its ultrasound waves is upon tissue designated for removal. In the example illustrated, intra-organ ultrasound probe 28 may have ultrasound waves focused on the region or area 84 of the tumor 37 designated for removal, wherein the intensity of such waves result in an output exposure level that exceeds the corresponding exposure level set forth in the FDA guidelines. The greater intensity meeting result in greater ultrasound penetration for deeper imaging and greater image resolution.

In some implementations, the first area of tissue upon which the ultrasound waves are focused during the first mode experiences an exposure level of less than or equal to 190 W/cm$^2$ and wherein the second area of tissue, designated for surgical removal, and upon which ultrasound waves are focused, during the second mode experiences and exposure level that exceeds 190 W/cm$^2$. In some implementations, the first area of tissue upon which the ultrasound waves are focused during the first mode experiences an exposure level of less than or equal to 720 mW/cm$^2$ and wherein the second area of tissue, designated for surgical removal, and upon which ultrasound waves are focused, during the second mode experiences and exposure level that exceeds 720 mW/cm$^2$.

In some particular implementations, intra-organ ultrasound probe 28 may be controlled in response to control signals received from a medical practitioner via an input device or maybe automatically controlled by controller so as to carry out a method wherein intra-organ ultrasound probe 28 is operated in a first mode with an acoustic field emission focused on organ of the patient and having a first output exposure level. When operating in the first mode, the controller or medical practitioner uses images or data signals acquired from the intra-organ ultrasound probe to identify tissue associated with the organ for removal. Intra-organ ultrasound probe is then operated in a second mode within acoustic field emission focused on the identified tissue, the acoustic field emission having a second output exposure level greater than the first output exposure level. In some implementations, the first exposure level of less than or equal to 190 W/cm$^2$ and the second exposure level exceeds 190 W/cm$^2$. In some implementations, the first exposure level is less than or equal to 720 mW/cm$^2$ and wherein the second exposure level that exceeds 720 mW/cm$^2$.

In some implementations, probes 24 and 28 may cooperate with one another, wherein probe 24 is operated such that its ultrasound waves are focused on portions of organ 36 may contain healthy tissue competition not designated for removal, while probe 28 may be operated such as its ultrasound waves are focused on tissue specifically designated for removal. In such an implementation, transducer 76 of probe 24 may be operated in compliance with the above noted guidelines with the focus of its ultrasound waves including healthy tissue, tissue not designated for surgical removal. Transducer 78 of intra-organ ultrasound probe 28 may be operated so as to produce ultrasound waves with an intensity and output exposure level exceeding the exposure level set forth in the FDA guidelines. In the example illustrated, intra-organ ultrasound probe 28 may have ultrasound waves focused on the region or area 84 of the tumor 37 designated for removal, wherein the intensity of such waves result in an output exposure level that exceeds the corresponding exposure level set forth in the FDA guidelines. The greater intensity may result in greater ultrasound penetration for deeper imaging, greater or better image resolution, and an improved signal-to-noise ratio.

The example organ and surgery monitoring shown in FIGS. 3A and 3B concurrently utilizes both of probes 24 and 28 with their respective transducers 76 and 78 to concurrently image a larger surrounding environment of tumor 37 and a potentially more detailed smaller region, inside the tumor 37, where the surgical procedure is to take place. Probes 24 and 28 cooperate to provide a medical practitioner (or automated robotic surgical system) with a larger amount of data. As a result, the medical practitioner or automated robotic surgical system may more precisely and accurately monitor and control the positioning of a surgical tool or effector within the organ 36 relative to the tumor 37.

In some implementations, probes 24 and 28 may be used independently of one another. For example, in some implementations, organ surface ultrasound probe 24 may be used to monitor the positioning of a tool or effector within an organ without the use of intra-organ ultrasound probe 28. In such implementations, probe 24 may provide a three-dimensional volume formed by the field-of-view 38 as shown in FIG. 2. As discussed above, because the probe 24 is fixed to the surface of the organ, probe 24 provides a "set it and forget it" functionality without necessarily requiring support from a secondary ultrasound transducer.

FIG. 3C illustrate portions of an example ultrasound sensing system 86 with multiple ultrasound sensors position for obtaining ultrasound data for region of interest within or on an organ 36. System 86 comprises a first ultrasound probe comprising organ surface ultrasound sensor 24 (described above), a second ultrasound probe 88 and a processing unit 90.

Second ultrasound probe 88 comprises an all ultrasound or transducer configured to be positioned in closer proximity to a region of interest or area of organ 36 than ultrasound probe 24. In the example illustrated, organ surface ultrasound probe 24 is configured to be positioned on the surface of organ 36 at a first distance from the region of interest, tumor 37. Second ultrasound probe 88 is configured to be positioned at a location at a second distance, less than the first distance, from the region of interest, tumor 37. In the example illustrated, the second ultrasound sensor 88 comprises a second organ surface ultrasound probe. In other implementations, the second ultrasound probe 88 may comprise an intra-organ ultrasound probe. Throughout the disclosure, it should be understood that any of the ultrasound sensing systems described as including an intra-organ ultrasound probe may alternatively employ a second organ surface ultrasound probe similar to the second ultrasound sensor 88. In some implementations, the second ultrasound sensor 88 may comprise a micro transducer which may be static, or which may be moved along the surface of organ 36 or within organ 36. For example, in some implementations, the organ surface ultrasound probe may remain static or stationary, mounted to organ 36, while the second ultrasound probe 88 may move along the surface, wherein such movement may be based upon movement of an effector or cutting tool. In some implementations, the second ultrasound probe may have a field-of-view that encompasses the effector or cutting tool and/or regions of the organ surface just ahead of the effector or cutting tool, regions that contain the expected or anticipated future path of the effector or cutting tool.

In some implementations, probe 88 may operate at a different frequency than that of probe 24. For example, in some implementations, transducer 76 of the organ surface ultrasound probe operates or emits mechanical waves at a frequency of at least 8 MHz and no greater than 20 MHz, ultrasound probe 88 emits mechanical waves at a frequency of at least MHz and no greater than 35 MHz. In some implementations, ultrasound probe 88 emits mechanical waves at a frequency greater than the frequency at which transducer 76 of the surface ultrasound probe emits mechanical waves.

Ultrasound data or signals collected by probes 24 and 88 are transmitted to processing unit 90. Processing unit 90, following instructions contained in a non-transitory computer-readable medium 91, superimposes and/or registers the first ultrasound data 92 (schematically represented) obtained from ultrasound probe 24 and the second ultrasound data 94 (schematically represented) obtained from ultrasound probe 88. For example, ultrasound data values from each of the two sensors may be assigned or aligned to the same physical location, a registration of coordinates. As indicated by arrow 93, the registered sets of data 92, 94 may be transmitted to a controller 94 to assist with automation or robotic surgery. As indicated by arrow 95, the superimposed and/or registered ultrasound data may additionally or alternatively be communicated to a display unit 96 which uses the registered ultrasound data to generate and display superimposed and registered ultrasound images for viewing by a medical practitioner or other person.

In some implementations, the first and/or second ultrasound probes 24, 88 may operate in different modes depending upon where the ultrasound energy is being focused. For example, in circumstances where the ultrasound probe is focusing its energy on a region 84 which is to be surgically removed, a controller may increase the intensity of the ultrasound energy to a level above or exceeding existing Food and Drug Administration (FDA) guidelines for exposure levels for healthy tissue. Because the tissue 84 receiving the otherwise excessive ultrasound output exposure levels is designated for removal, any risk of damage to such tissue caused by excessive acoustic output exposure levels is not relevant and disregarded. Because the ultrasound probe is operated at a higher intensity in the focused upon area of the organ, which is to be removed, the penetration of the ultrasound waves into the tissue may be deeper and the images generated or derived from such ultrasound waves may have a greater resolution.

Organ Surface Ultrasound Probe

Figures 4, 5, 6, 7:
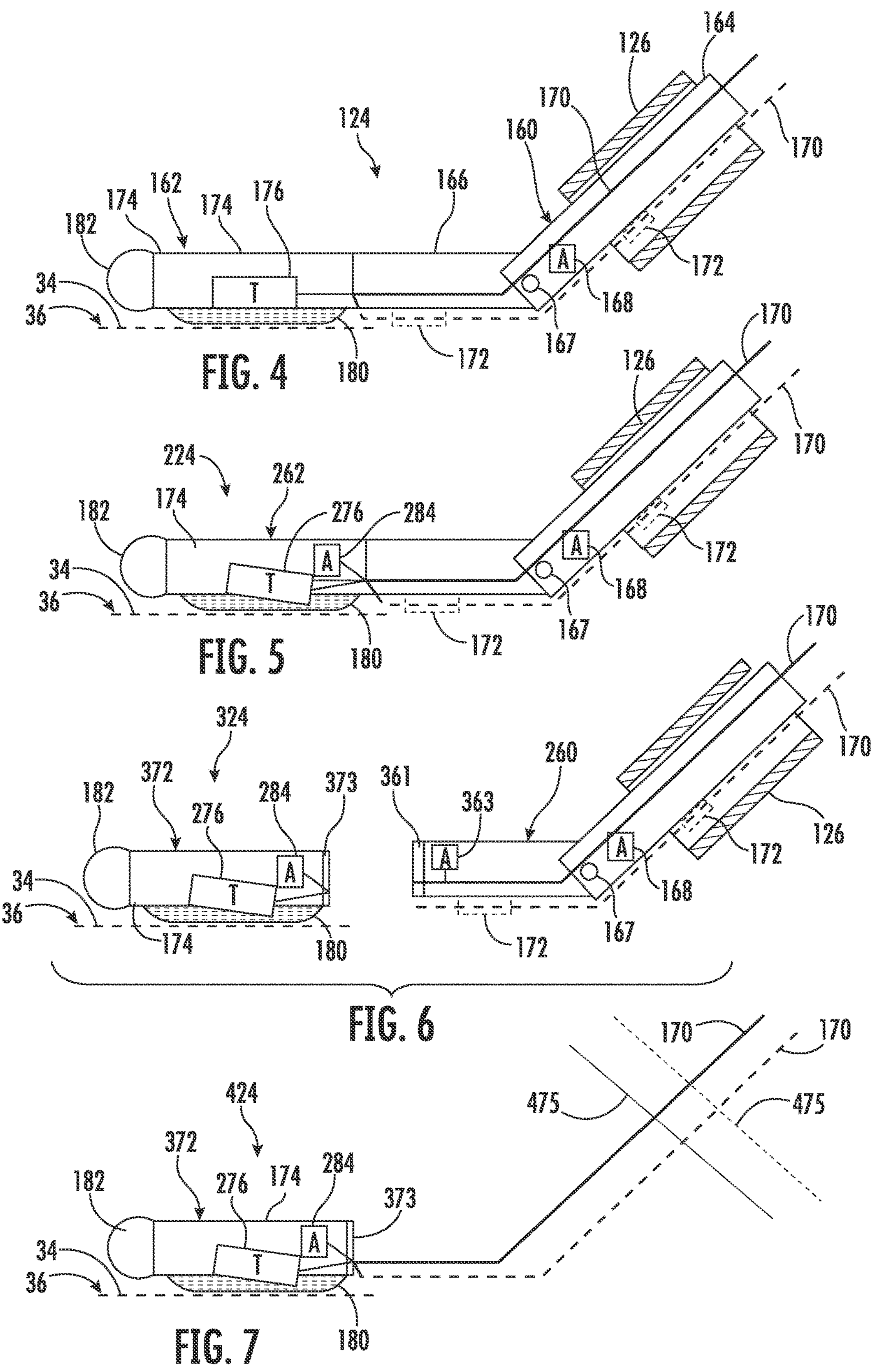
FIG. 4 is a sectional view schematically illustrating portions of an example organ surface ultrasound probe.
FIG. 5 is a sectional view schematically illustrating portions of an example organ surface ultrasound probe.
FIG. 6 is a sectional view schematically illustrating portions of an example organ surface ultrasound probe.
FIG. 7 is a sectional view schematically illustrating portions of an example organ surface ultrasound probe.

FIG. 4 is a diagram schematically illustrating portions of an example organ surface ultrasound probe 124 positioned against or in conformable contact with the exterior surface 34 of organ 36. Probe 124 may be utilized as part of ultrasound sensing system 20 described above. Probe 124 may be used in cooperation with probe 28 and display unit 32 to provide the at least partially registered images 50 and 52 for monitoring an interior surface of organ 36 or may be used independent of and without concurrent use of probe 28. As shown by FIG. 4, probe 124 is inserted through the interior of a tube or trocar 126.

Organ surface ultrasound probe 124 comprises insertion shaft 160 and sensing head 162. Insertion shaft 160 facilitates the positioning of sensing head 162 into conformable contact with surface 34. Insertion shaft 160 is configured to pass through trocar 126 and then be articulated to a proper angle such that sensing head 162 extends substantially parallel to the opposite portions of the exterior surface 34 of organ 36. In the example illustrated, insertion shaft 160 comprises a first or proximal segment 164 and a second or distal segment 166. Segment 166 extends between segment 164 and sensing head 162. Segment 166 is pivotably coupled to segment 164 about a pivot joint 167 such that segment 166 and head 162 may be pivoted to an orientation substantially parallel to surface 34. In the example illustrated, one of segments 164, 166 includes an actuator 168 for selectively and controllably pivoting segments 164, 166 relative to one another about joint 167. Actuator 168 may comprise an electric solenoid, hydraulic or pneumatic cylinder-piston assembly, an electric servo or stepper motor or the like. In some implementations, actuator 168 may be omitted.

Segments 164, 166 of insertion shaft 160 support a bundle 170 of electrical and/or fluid lines. Such electrical lines may include electrical wires or cables for supplying electrical power to and controlling actuator 168 and sensing head 162. Such fluid lines may include tubes or fluid conduits for supplying pressurized fluid to sensing head 162 for purposes such as hydraulically or pneumatically moving portions of head 162 and/or for cooling components of sensing head 162. In some implementations, those fluid lines forming bundle 170 may include a supply line and a return line providing fluid circulation.

As shown in solid lines, in one implementation, bundle 170 is contained within an interior of segments 164 and 166. As shown by broken lines, bundle 170 may additionally or alternatively be supported along an exterior of segments 164, 166. In such an implementation, segments 154 and 166 may additionally include exterior sleeves or guides 172 for retaining bundle 170 against and along the exterior of segments 164 and 166.

In some implementations, sensing head 162 may not rely upon bundle 170 for power and/or communication. For example, bundle 170 may not be connected to sensing head 162. In such an implementation, sensing head 162 may be powered by a locally stored battery or may be powered wirelessly. In such an implementation, sensing head 162 may communicate with external devices, such as display unit 32, in a wireless fashion.

Sensing head 162 of probe 124 generates signals that are used to form image 50 (shown in FIG. 1). Sensing head 162 comprises housing 174, transducer 176, and acoustic coupler 180. Housing 174 comprises a body, stage, or other structure that supports transducer 176. In some implementations, housing 174 has a cylindrical or oval cross-sectional shape with transducer 176 located along a side of the housing 174. In some implementations, housing 174 has a flat shape, a shape where a length and/or width of housing 174 is greater than the thickness of housing 174 (the vertical direction in FIG. 4). In such implementations, transducer 176 may be spread along the flat side of housing 174 which is positioned against the organ surface. In some implementations, housing 174 has a curved outer profile. For example, housing 174 may have a curved side or face that has a radius of curvature chosen so as to substantially match the curvature of the organ surface against or along which housing 174 is to be positioned. In such implementations, transducer 176 may extend along the curved side. In some implementations, transducer 176 may have a curved profile.

In some implementations, housing 174 is formed from a rigid un-bendable material such as a rigid polymer. In other implementations, housing 174 is formed from a bendable or compliant material such as a flexible polymer. In such implementations, housing 174 may be bent to match the curvature of the organ surface. In such implementations, housing 174 may be bent as it is steered through a trocar or move towards the organ surface.

Housing 174 is connected to segment 166 of insertion shaft 160 and terminates at a tip 182. In the example illustrated, tip 182 is blunt, lacking a sharp point which may puncture, cut or potentially damage tissue during insertion. In some implementations, tip 182 is formed from a soft or elastomeric material, further reducing the likelihood of tip 182 causing damage during insertion or movement. In other implementations, tip 182 may be formed from other materials or have other configurations. In some implementations, the surface of housing 174 includes at least one protrusion that attaches to the surface of the patient's organ maintaining housing 174 in a fixed position relative to the surface 34 of the patient's organ even as the patient's organ moves and/or is deformed.

Transducer 176, sometimes referred to as an ultrasonic sensor, comprise a device configured to generate and sense ultrasound energy, mechanical waves. In the example illustrated, transducer 176 comprises an ultrasound transceiver, a device that may convert electrical signals into ultrasound or mechanical waves and that may receive and convert reflected or scattered ultrasound or mechanical waves into electrical signals which are then detected, conditioned, post-processed for display. Such signals, at some point, are transmitted to display unit 32 (shown in FIG. 1) via bundle 170 or wirelessly. In some implementations, transducer 176 comprises a piezoelectric (PZT) transducer that converts alternating electrical current (AC) into ultrasound using piezoelectric crystals, wherein the AC voltage oscillates such crystals to produce the ultrasonic sound or mechanical waves. In some implementations, transducer 176 may comprise a capacitive transducer which generates ultrasound or mechanical waves using electrostatic fields between a conductive diaphragm and a backing plate. In some implementations, transducer 76 may comprise a plurality of individual transducer elements or an array of transducer elements. In some implementations, transducer 176 may comprise a conformable (conformable) transducer, a transducer having multiple transducer element supported by a flexible substrate.

In one implementation piezoelectric crystals forming transducer 176 may be moved about the longitudinal axis. Movement of piezoelectric crystals may be moved with housing or relative to the housing. In one implementation, the ultrasound probe may include a drive mechanism to position or rotate piezoelectric crystals relative to the housing such that when the housing is fixed within a patient's organ it is possible to increase the area in which an image can be obtained from ultrasound probe 108. In one implementation the housing of the probe along with piezoelectric crystals may be positioned or rotated together by a drive mechanism to increase the area of the image obtained.

In one implementation, the piezoelectric crystals may be rotated 360 degrees within the housing or with the housing to provide a 360-degree view of the patient's organ. In this manner, an imaging system may process 360 degrees of the organ with a refresh rate sufficient to provide an updated view per rotation. The frequency of images acquired are sufficient for a surgeon to detect changes and deformation of organ during a surgical procedure. In one implementation, the piezoelectric crystals are rotated back and forth about a longitudinal axis of the ultrasound probe less than 360 degrees. In one implementation, rotation of piezoelectric crystals may be 180 degrees. In one implementation rotation of piezoelectric crystals may be between 0 degrees and 360 degrees and in one other implementation rotation of piezoelectric crystals may be between 180 and 360 degrees. In one implementation rotation is between 0 and 180 degrees.

In one implementation transducer 76 is a linear transducer with the piezoelectric crystals arranged in a linear array along the longitudinal axis of its housing. Although transducer 176 has been described as having piezoelectric crystals, other types of materials known in the art to produce an ultrasonic image may be used. As non-limiting examples chip-based transducers, or micromachined ultrasound transducers (MUTs), that use silicon chips to convert voltage to resonance may be used.

In one implementation real time images show blood flowing through the blood vessels. In surgical robotics, successive ultrasound images are provided to allow a surgeon to manipulate a surgical tool based on the real time images. Stated another way, the images are refreshed with sufficient frequency to provide a surgeon with current information as the surgeon manipulates a patient with a robotic tool. Stated another way, real time ultrasound provides multiple images of an anatomical structure in the form of motion. In one implementation each image is provide multiple times per second. In one example over 10 images are provided per second. In another example over 20 images are provided per second. Real time images allows an imaging system to monitor the organ deformation in real time.

In some implementations, the transducer 176 may be at least partially immersed within the acoustic coupling medium of the acoustic coupler. For example, a bottom face and sides of the transducer 176 may be directly adjacent to the acoustic coupling medium. In some implementations, the acoustic coupling medium may be more of a solid, wherein the transducer 176 abuts a top face of the acoustic coupler 180.

In some implementations, the acoustic coupler 180 may comprise a hydrogel. In some implementations, the hydrogel may include mechanical anchor points located on or embedded in the hydrogel, wherein the anchor points mount and secure transducer 176 to or within the hydrogel. In some implementations, the hydrogel may include electrically conductive traces imprinted upon or embedded in the hydrogel, wherein the electrically conductive traces facilitate electrical powering of transducer 176 and transmission of electrical signals to and from transducer 176. Such electrical signals may be control signals for controlling transducer 176 as well as data signals representing or based upon sensed reflected ultrasound/mechanical waves.

FIG. 5 is a diagram schematically illustrating portions of an example organ surface ultrasound probe 224. FIG. 5 illustrates an example of how a transducer may be controllably repositioned to selectively adjust the field of view of the transducer. Probe 224 may be utilized as part of ultrasound sensing system 20 described above. Probe 224 may be used in cooperation with probe 28 and display unit 32 to provide the at least partially registered images 50 and 52 for monitoring an interior surface of organ 36 or may be used independent of and without concurrent use of probe 28. Probe 224 is similar to probe 124 except that probe 224 comprises sensing head 262 in place of sensing head 162. The remaining components of probe 224 which correspond to components of probe 124 numbered similarly.

Sensing head 262 is similar to sensing head 162 except that head 262 comprises transducer 276 and actuator 284. Transducer 276 may be similar to transducer 176 except that transducer 276 is movably coupled to housing 174 such that transducer 276 may pivot or otherwise move relative to housing 174 to alter the field of view of transducer 276. In some implementations, transducer 276 may be movably supported by a gimbal or other joint supported by housing 174. In some implementations, transducer 276 may be supported by a flexible substrate which may be bent or flexed to reposition transducer 276. In some implementations, transducer 276 may be supported within or on a hydrogel which may be bent or deformed to alter the angle or positioning of transducer 276.

Actuator 284 comprises a device to selectively alter the orientation (angle) and/or extension/retraction of transducer 276 relative to housing 174. In one implementation, actuator 284 comprises piezoelectric or piezo-resistive actuators or a PZT bimorphs spaced along a flexible substrate to individually move respective portions of the substrate and to individually steer associated transducer elements supported by the flexible substrate. In some implementations, actuator 284 may comprise other mechanical actuators such as solenoids, hydraulic or pneumatic pneumatically driven pistons or the like. Actuator 284 is controlled via electrical signals received via bundle 170 or received wirelessly from an external probe control system.

FIG. 6 is a diagram schematically illustrating portions of an example organ surface ultrasound probe 324. FIG. 6 illustrates an example of how a sensing head supporting a transducer may be releasably coupled to and separable from an insertion shaft, permitting the sensing head to remain secured to the exterior surface 34 of organ 36 while insertion shaft 260 is withdrawn. Probe 324 may be utilized as part of ultrasound sensing system 20 described above. Probe 324 may be used in cooperation with probe 28 and display unit 32 to provide the at least partially registered images 50 and 52 for monitoring an interior surface of organ 36 or may be used independent of and without concurrent use of probe 28. Probe 324 comprises sensing head 372 and insertion shaft 260.

Sensing head 372 and insertion shaft 260 are similar to sensing head 262 and insertion shaft 160, respectively, described above, except that each additionally comprises a releasable coupling interface. Segment 166 comprises coupling interface 361 while sensing head 372 comprises coupling interface 373. Interfaces 361 and 373 are configured to releasably connect to one another. In some implementations, the releasable connection is controlled via a remote electrical signal transmitted by an electrical line of bundle 170 to a connection actuator 363. For example, the connection actuator may include a hook, latch or other mechanism movable by actuator 363 between a sensing head connecting state and a sensing head releasing state. In some implementations, the connection may be magnetic.

Interface 361 further includes electrical contact pads and male/female fluid connectors that are configured to mate with corresponding electrical contact pads and female/male fluid connectors of interface 373. Separation of insertion shaft 260 and sensing head 372 results in electrical disconnection and fluid disconnection. Fluid disconnection results in the connecting ports being closed or sealed upon disconnection or separation of sensing head 372 from insertion shaft 260.

FIG. 7 is a diagram schematically illustrating organ surface ultrasound probe 424. FIG. 7 illustrates an example of how an insertion shaft may be disconnected from a sensing head and withdrawn while the electrical lines and/or fluid lines remain connected to the sensing head, permitting the sensing head to continue to function while acoustically coupled to an organ. Organ surface ultrasound probe 424 is similar to organ surface ultrasound probe 324 described above except that bundle 370 is removably or releasably coupled to insertion shaft 260. In some implementations, insertion shaft 260 may be pulled relative to bundle 370 during its withdrawal from the patient's anatomy, permitting bundle 372 remain connected to sensing head 372. Bundle 370 may continue, extending from sensing head 372 through an insertion opening or incision 475 in the anatomy of the patient. Sensing head 372 may remain secured to the exterior surface 34 of organ 36, continuing to communicate via the electrical lines of bundle 370 and to receive or circulate any fluids via the fluid lines of bundle 370.

Figure 8:
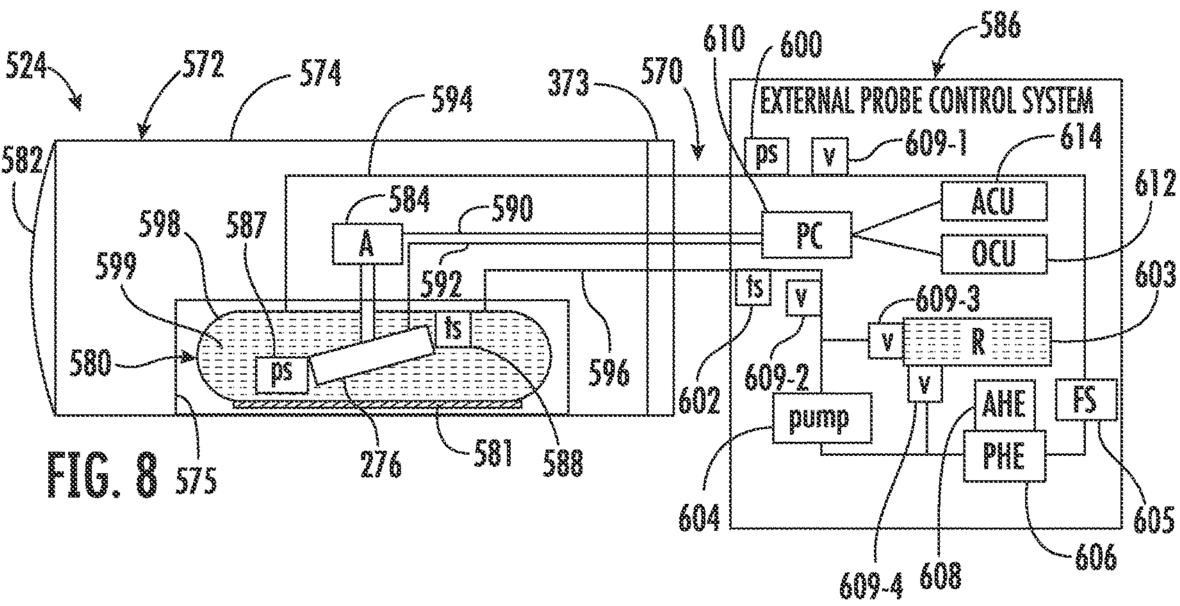
FIG. 8 is a sectional view schematically illustrating portions of an example organ surface ultrasound probe.

FIG. 8 is a diagram schematically illustrating portions of an example organ surface ultrasound probe 524. FIG. 8 schematically illustrates portions of an external probe control system that are associated with the sensing head and that assist in regulating a temperature of the sensing head while controlling the sensing head. Those portions of probe 524 which correspond to portions of probe 424 are numbered similarly and/or are shown in any of FIGS. 4-7 described above. Probe 524 comprises sensing head 572, bundle 570, insertion shaft 260 (shown and described with respect to FIG. 6) and external probe control system 586.

Sensing head 572 comprises housing 574, coupling interface 373 (described above), transducer 276, acoustic coupler 580, adhesive layer 581, actuator 584, pressure sensor 587 and temperature sensor 588. Housing 574 extends along a longitudinal axis from coupling interface 373 to a tip 582. Tip 582 similar to tip 182. In some implementations, tip 582 is blunt and may be soft or elastomeric. Housing 574 supports the remaining components of sensing head 572. Housing 574 includes an internal cavity 575 which opens in a direction transverse to the longitudinal axis of sensing head 572.

Coupling interface 373 and transducer 276 are described above. In the example illustrated, coupling interface 373 provides a releasable mechanical coupling of sensing head 572 to insertion shaft 260. In some implementations, coupling interface 373 as well as the coupling interface 361 of insertion shaft 260 may be magnetic. In one implementation, the magnetic coupling is electromagnetic, wherein the supply of electric current may be reduced or stopped to release sensing head 572 from insertion shaft 260. In some implementations, the electric current may be controlled to reverse the polarity and repel insertion shaft 260 from sensing head 572.

As further shown by FIG. 8, coupling interface 373 and housing 574 support electrically conductive lines 590 (wires or traces) for communication with and/or supplying power to actuator 584 and electrically conductive lines 592 for communication with and/or supplying power to transducer 276. Coupling interface 373 and housing 574 further supports fluid supply line 594 (a tube or fluid passage) and fluid return line 596. Coupling interface 373 connects electrical lines 590, 592 and fluid lines 594, 596 to corresponding electrical and fluid lines contained within bundle 570. Such corresponding electrical and fluid lines connect to external probe control system 586. Like bundle 170, bundle 576 is releasably connected to insertion shaft 260, extending within insertion shaft 160 or through sleeves or other structures along the exterior of insertion shaft 260, permitting insertion shaft 260 to be withdrawn while bundle 570 remains connected to sensing head 572.

As described above, transducer 276 is movable relative to housing 574. Transducer 276 may be reoriented or pivoted within cavity 575. Transducer 276 may be selectively extended or retracted within cavity 575. Transducer 276 is immersed within acoustic coupler 580.

Acoustic coupler 580 provides an efficient path for ultrasound propagation between transducer 276 and surface 34 of organ 36 (shown in FIG. 1). Acoustic coupler 580 comprises flexible bladder 598 and acoustic coupling medium 599. Bladder 598 comprise a thin flexible or deformable film, membrane or layer containing acoustic medium 599. In some implementations, bladder 598 may be formed from a strong and flexible material such as polyethylene, having a thickness from 25 μm to 100 μm. In other implementations, bladder 598 may be formed from other or rigid material such as polyimide, polypropylene, acrylics, polyesters, mylar or the like. Bladder 598 is received within cavity 575 and is configured to be inflated with the fluid coupling medium 599 to an extent such that lower portions of bladder 598 may extend beyond cavity 575. Bladder 598 may be sealed about those portions of actuator 584 extending into the interior bladder 598 for connection to transducer 276. Bladder 598 may be further sealed about ports for fluid lines 594 and 596.

Acoustic coupling medium 599 comprises a coupling agent having a low absorption coefficient and an acoustic impedance similar to a higher than that of the tissue of organ 36. In the example illustrated, the acoustic coupling medium 599 may comprise a liquid or fluid such as water or solutions largely composed of water. As will be described hereafter, the acoustic coupling medium 599 may initially be circulated within bladder 598 to regulate the temperature of transducer 276. In the example illustrated, acoustic coupling medium 599 surrounds the transducer 276. For example, a bottom face and sides of the transducer 276 may be directly adjacent to the acoustic coupling medium.

Adhesive layer 581 extends along a lower surface of bladder 598. Adhesive layer 581 comprises an adhesive material configured to adhesively bond to the exterior surface 34 of organ 36 (shown in FIG. 1). Adhesive layer 581 has a thickness sufficient to retain bladder 580 and sensing head 572 and contact with the organ surface (or a compliant layer as described hereafter). In some implementations, adhesive layer 581 is further configured to react with a solvent for subsequent release from the surface 34 of the organ 36. In some implementations, the adhesive layer may comprise a dissolving or releasing agent for removal after placement. In some implementations, adhesive layer 581 may be directly coated upon bladder 598. In some implementations, adhesive layer 581 may be sprayed upon bladder 598. For example, in some implementations, adhesive layer 581 may comprise a fibrin sealant or material such as Tisseel commercially available from Baxter Healthcare. In such implementations, adhesive layer may have a thickness no greater than 2 mm and, in some implementations, no greater than 1 mm. In other implementations, adhesive layer 581 may be provided as part of a two-sided tape adhesively secured to bladder 598. The materials of adhesive layer 581 and any film supporting the adhesive layer may be acoustically transparent, having acoustic impedance properties similar to that of the acoustic coupling medium 599 and the tissue forming the exterior surface 34 of organ 36. In other implementations, adhesive layer 581 may be omitted or may be replaced with other mechanisms for securing and retaining acoustic coupler 580 relative to and in contact with exterior surface 34 of organ 36.

Actuator 584 comprise a device supported by housing 574 and configured to selectively reorient and/or extend/retract transducer 276 within bladder 598. In one implementation, actuator 584 comprises piezoelectric or piezo-resistive actuators or a PZT bimorphs spaced along a flexible substrate supporting transducer elements of transducer 276 to individually move respective portions of the substrate and to individually steer associated transducer elements supported by the flexible substrate. In some implementations, actuator 584 may comprise other mechanical actuators such as solenoids, hydraulically or pneumatically driven pistons or the like connected to transducer 276 by a gimbal or other joint. Actuator 584 is controlled via electrical signals received via electrical lines 590 and corresponding electrical lines of bundle 170. In some implementations, actuator 584 may alternatively be controlled by signals received wirelessly from external probe control system 586.

Pressure sensor 587 comprises a sensor configured to detect the pressure of the liquid or fluid within bladder 598. Pressure sensor 587 may be in direct communication with the fluid or may be in indirect communication with the fluid using in intermediate film or diaphragm. In some implementations, pressure sensor 587 may be supported within housing 574 outside of cavity 575, wherein a fluid passage is provided from cavity 575 to the pressure sensor 587. Pressure sensor 587 outputs electrical signals which are transmitted to external probe control system 586. Such electrical signals, corresponding to the pressure of acoustic coupling medium 599, may be transmitted wirelessly or through electrical lines provided in housing 574 and interface 373, extending through bundle 570 to external probe control system 586.

Temperature sensor 588 comprises a sensor configured to detect the temperature of transducer 276. In some implementations, temperature sensor 588 directly senses the temperature of transducer 276. In some implementations, temperature sensor 588 indirectly senses the temperature of transducer 276, such as by sensing the temperature of the environment surrounding transducer 276, such as a temperature of acoustic coupling medium 599. In some implementations, temperature sensor 588 may be in direct contact with the acoustic coupling medium. In some implementations, temperature sensor 588 may reside on a thermally conductive material that is in physical contact with the acoustic coupling medium. In some implementations, temperature sensor 588 may comprise a thermistor. Temperature sensor 588 outputs electrical signals corresponding to the sensed temperature of transducer 276, wherein such electrical signals are transmitted to external probe control system 586 either wirelessly or in a wired fashion through electrical lines supported by housing 574 and interface 373 and further extending within bundle 570.

External probe control system 586 controls the operation of sensing head 572 of organ surface ultrasound probe 524. External probe control system 586 is located external to the patient's anatomy and communicates with sensing head 572 either wirelessly or via bundle 570. External probe control system 586 may be part of a larger system which controls other components of ultrasound sensing system 20. For example, external probe control system 586 may share components, processing units and the like, with other control systems that also control intra-organ ultrasound probe 28 or which control tools used during the medical procedure. External probe control system 586 may include display unit 32 described above or may communicate with display unit 32. External probe control system 586 comprises pressure sensor 600, temperature sensor 602, reservoir 603, pump 604, flow sensor 605, passive heat extractor 606, active heat extractor 608, valves 609-1, 609-2, 609-3 and 609-4 (collectively referred to as valves 609), probe controller 610, operator control unit 612 and automated control unit 614.

Pressure sensor 600 comprises a sensor in communication with probe controller 610 and configured to detect the pressure of the fluid serving as the acoustic coupling medium 599. Pressure sensor 600 is located external to the anatomy of the patient as part of system 586. Pressure sensor 600 may detect the pressure of fluid being moved through fluid supply line 594 or being returned via supply return line 596. In some implementations, pressure sensor 587 may be omitted where pressure sensor 600 is provided. In some implementations, pressure sensor 600 may be omitted.

Temperature sensor 602 comprise sensor in electrical communication with probe controller 610 and configured to detect the temperature of the fluid being drawn from or exiting bladder 598. Temperature sensor 602 provides electrical signals indicating the temperature of the fluid which may indirectly correspond to the temperature of transducer 276. Temperature sensor 602 is located external to the anatomy of the patient as part of system 586. In some implementations, temperature sensor 602 may be omitted where temperature sensor 588 is provided. In some implementations, temperature sensor 602 may be omitted.

Reservoir 603 comprises a chamber, container or other volume containing a supply of the fluid serving as acoustic coupling medium 599. Reservoir 603 supplies fluid for those times during which bladder 598 is being inflated with additional fluid. Reservoir 603 receives fluid during those times during which bladder 598 is being deflated.

Pump 604 is located external to the anatomy of the patient. Pump 604 is in electrical communication with probe controller 610 for being controlled by controller 610. Pump 604 is fluidly connected or coupled between fluid return line 596 and fluid supply line 594. In some implementations, pump 604 may comprise a peristaltic pump. In other implementations, pump 604 may comprise other forms of a fluid pump. Pump 604 controllably circulates fluid into bladder 598, across transducer 276, and out of bladder 598. In the example illustrated, the ports of fluid supply line 594 and fluid return line 596 are located on opposite sides of transducer 276 to generate a cross flow of fluid across transducer 276. In the example illustrated, pump 604 draws fluid from bladder 598 through fluid return line 596 so as to create a negative pressure within bladder 598 that draws fluid into bladder 598 through fluid supply line 594. In other implementations, pump 604 may alternatively work in a reverse fashion, directly moving fluid into bladder 598.

Flow sensor 605 comprises a sensor configured to output signals indicating the flow of fluid or acoustic coupling medium 599 through the circulatory system extending through sensing head 572 and external probe control system 586. Flow sensor 605 may comprise a flow meter. Although illustrated as being distinct from pump 604, some implementations, flow sensor 605 may be incorporated as part of pump 604. Flow sensor 605 transmits signals indicating fluid flow probe controller 610 in a wired or wireless fashion. Probe controller 610 may utilize such signals as part of a closed feedback loop to adjust the operation of pump 604 and one or more of valves 609 to modify the flow of fluid to assist in controlling the inflation/deflation of bladder 598 and/or the cooling of transducer 276 by such fluid circulation. In some implementations, flow sensor 605 may additionally or alternatively be provided on sensing head 572 to directly detect the flow of fluid through lines 594 and/or 596.

Passive heat extractor 606 is located between pump 604 and fluid return line 594. Passive heat extractor 606 comprises a fluid passage through a highly thermally conductive material such as aluminum or the like for absorbing heat within the fluid and spreading the heat for dissipation to the surrounding environment. In some implementations, passive heat extractor 606 may comprise a series of fins for dispersing heat from the fluid being circulated and serving as the acoustic coupling medium 599.

Active heat extractor 608 comprises a mechanism to actively withdraw heat from passive heat extractor 606 and from the fluid circulation passenger line that is part of external probe control system 586. Active heat extractor 608 is in electrical communication with probe controller 610 for being controlled by probe controller 610. In some implementations, active heat extractor 608 comprises a fan or blower to move air across the fins of passive heat tractor 606 to dissipate heat therefrom. In some implementations, active heat extractor 608 may comprise a Peltier device. In some implementations, one or both of passive heat effective 606 and active heat tractor 608 may be omitted.

Valves 609 comprise individual valves which are under the control of probe controller 610, communicating with probe controller 610 via electrical wires or traces. Valve 609-1 controls the flow of fluid to fluid supply line 594. Valve 609-2 controls the flow of fluid through fluid return line 596. Valve 609-3 controls the flow of fluid from reservoir 603. Valve 609-4 controls the flow of fluid from reservoir 603. In some implementations, valve 609-3 and 609-4 may be combined into one valve mechanism.

Probe controller 610 comprises a processing unit and instructions contained in a non-transitory computer-readable medium, wherein the instructions direct the program controller 610 control and regulate the operation of sensing head 572. Probe controller 610 may further carry out commands or requests received from either or both of operator control unit 612 and automated control unit 614. Operator control unit 612 comprises a processing unit and instruction contained in an associated non-transitory computer-readable medium. Operator control unit 612 may further comprise an operator input by which an operator or medical practitioner may input a request to initiate the monitoring of organ 36. In some implementations, the operator control unit 612 may output control signals initiating such monitoring based upon additional ongoing conditions as sensed or detected by external probe control system 586.

Automated control unit 614 comprises a processing unit and associated instructions contained in a non-transitory computer-readable medium. Automatic control unit 614 may be part of a larger automated robotic system which automatically makes decisions and outputs control signals based upon a pre-defined or preprogrammed routine which may dynamically adjust to ongoing real-time sensed conditions during a medical procedure. In some implementations, both of units 612 and 614 may cooperate as part of controlling sensing head 572. For example, one of units 612, 614 may output a requested command or action which must be approved by the other of such units 612, 614, whether it be manual approval by an operator or approval by the automated system (such as artificial intelligence) based upon sensed or determined conditions.

In particular implementations, probe controller 610 may automatically actuate pump 604 and one or more valves 609 based upon an imaging mode of probe 524 as selected by operator control unit 612 or automated control unit 614. Different imaging modes may result in different amounts of heat being generated and emitted by transducer 276. Different imaging modes may also have improved performance when transducer 276 is spaced from surface 34 of organ 36 by distance within a predefined range of distances. Upon receipt of a particular imaging mode, print controller 610 may automatically adjust the pumping of fluid, based upon the particular chosen imaging mode, to enhance the performance of probe 524. For example, for those imaging modes which result in transducer 276 generating and emitting a greater amount of heat, upon receiving such a selection, probe controller 610 may automatically increase the rate at which the fluid coupling medium 599 is circulated through bladder 598. For those imaging modes, the performance of which is enhanced by a larger spacing of transducer 276 from the organ surface, probe controller 610 may automatically move transducer 276 or additionally inflate bladder 598 to increase the distance separating transducer 276 from the organ surface. Conversely, for those imaging modes, the performance which is enhanced by smaller spacing of trenches are 276 from the organ surface, probe controller 610 may automatically move transducer 276 or deflate bladder 598 to decrease the distance separating transducer 276 from the organ surface.

Examples of different imaging modes that may be chosen by operator control unit 612 or automated control unit 614 and which result in probe controller 600 making automatic adjustments to the positioning of transducer 276, the operation of pump 604 and/or valve 609, the operation of active heat extractor 608 and the positioning of transducer 276 by actuator 584 include, but are not limited to, ultrasound-based tissue interrogation. Such modes may include: an elasticity imaging mode, a duplex mode, an A-mode reference signal visualization based upon ultrasound reflection data in a single line of interrogation), a B-mode (2D, extended field-of-view 2D and 3D) (an imaging mode producing gray-skill ultrasound images based on ultrasound reflection), a M-mode (signal visualization based on ultrasound reflection depicted as a function of time, and a Doppler mode (characterization of movement based upon Doppler frequency shift). Examples of various Doppler imaging modes include continuous wave (audio signal indicating movement in a line of interrogation), color Doppler (color-coded imaging showing movement with respect to the transducer axial direction), spectral Doppler or pulsed wave (a spectral signal, quantification of movement in user-defined sample volumes), power Doppler (color-coated imaging showing movement with no direction information) and a combination of any of the above Doppler modes. Additional imaging modes of operation may include speckle-tracking or a combination of any of the above modes superimposed on a display. Each of such modes may have has performance when transducer 276 is spaced from the surface the organ by distance within a predefined range. Each of such modes may further result entrances are 276 generating and emitting heat at different rates. By automatically adjusting to the image mode selection, probe controller 610 may enhance imaging performance and reduce likelihood of damage to transducer 276.

FIG. 8 illustrates sensing head 572 in an inactive state in which acoustic coupler 580 is recessed or retracted within cavity 575. Because acoustic coupler 580 is retracted within housing 574, sensing head 572 has a reduced size or diameter, facilitating movement of sensing head 572 through a tube or trocar through the outermost skin of a patient to a position proximate to organ 36.

The retracted or recessed state of acoustic coupler 580 is achieved by probe controller 610 outputting control signals to pump 604 and valves 609 such that a greater volume of fluid is withdrawn from bladder 598 as compared to the amount of fluid being supplied to bladder 598, reducing the extent of inflation of bladder 598. In one implementation, probe controller 610 outputs control signals closing valve 609-1, opening valve 609-2, closing valve 609-3 and opening valve 609-4. Probe controller 610 further outputs control signals actuating pump 604 such that fluid is drawn from bladder 598 and directed into reservoir 603.

Figure 9:
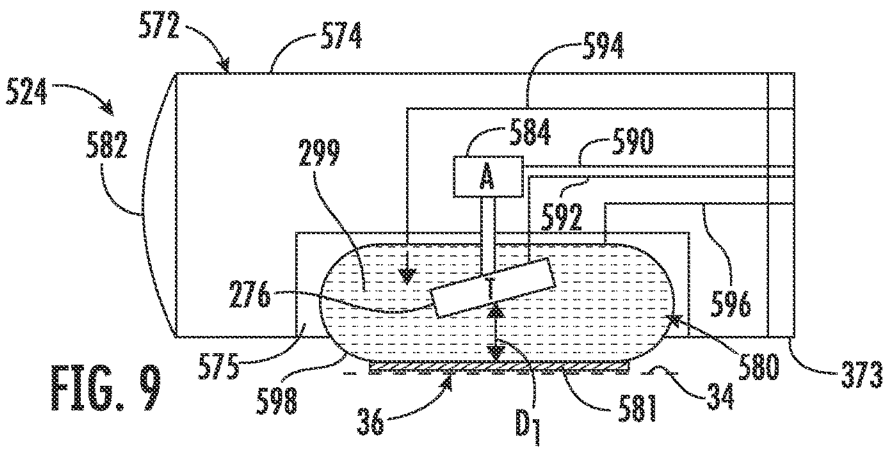
FIG. 9 is a sectional view schematically illustrating a sensing head of the example organ surface ultrasound probe of FIG. 8 with a bladder in a first inflated state.

FIG. 9 illustrates sensing head 572 in an active state in which acoustic coupler 580 is extended beyond cavity 575 for positioning acoustic coupler 580 into acoustic contact with external surface 34 of organ 36 (shown in FIG. 1). The extended state of acoustic coupler 580 is achieved by probe controller 610 outputting control signals such that a greater volume of fluid is supplied to bladder 598 as compared to the amount of fluid being withdrawn from bladder 598, increasing the extent of inflation of bladder 598. In one implementation, probe controller 610 outputs control signals opening valve 609-1 and 609-3 closing valves 609-2 and 609-4. Probe controller 610 further outputs control signals actuating pump 604 such that fluid is drawn from reservoir 603 and directed into bladder 598. Once bladder 598 has been sufficiently inflated or brought into sufficient contact with organ 36, probe controller 610 may output control signals closing valve 609-3. In some implementations, probe controller 610 may further close valve 609-1 and 609-2 and discontinue the operation of pump 604. In some implementations, as described below, probe controller 610 may continue the operation of pump 604 with valve 609-1 and 609-2 open so as to circulate fluid through and across the interior of bladder 598.

In some implementations, a degree of contact of adhesive layer 581/acoustic coupler 580 is determined based upon signals from an external ultrasound sensor. In some implementations, the degree of contact may be determined based on signals from transducer 276. In some implementations, the jury of contact may be determined based upon signals from pressure sensor 587 and/or pressure sensor 600, wherein a sufficient degree of contact may be a determined based upon the sensed pressure exceeding a predetermined threshold.

Once acoustic coupler 580 have been brought into sufficient acoustic communication or contact with the external surface 34 of organ 36, probe controller 610 may output control signals to actuator 584 to position and orient transducer 276 so as to achieve a desired target field of view. Once actuator 584 has moved transducer 276 to the desired position/orientation, probe controller 610 may output control signals to transducer 276 to begin collecting ultrasound data for use by display unit 32 in generating image 50 (shown in FIG. 1).

Transducer 276 may generate and emit heat during its operation. Probe controller 610 may monitor the heating up of transducer 276 based upon signals received from temperature sensor 588 and/or temperature sensor 602. Upon the detected temperature exceeding a predetermined threshold, probe controller 610, following the instructions contained in the non-transitory computer-readable medium, may output control signals initiating the circulation of fluid within bladder 598 and across transducer 276 by actuating pump 604 and opening valves 609-1 and 609-2. In some implementations, probe controller 610 may increase the extraction of heat from fluid 599 to cool transducer 276 by operating pump 604 at a higher rate so as to circulate fluid through bladder 598 at a higher rate. In some implementations, probe controller 610 may further increase the extraction of heat from fluid 599 to cool transducer 276 by turning on active heat exchanger 608 or increasing the rate at which active heat exchanger 608 extracts heat. By monitoring the temperature of transducer 276, directly or indirectly and by circulating fluid through bladder 598, external probe control system 586 may reduce the likelihood of damage to transducer 276 from overheating and/or reduce the likelihood of harm to the patient from excessive heat.

Figure 10A:
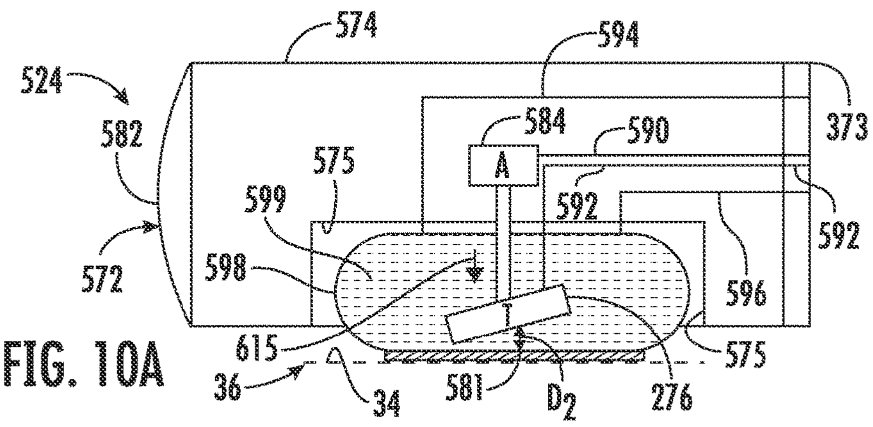
FIG. 10A is a sectional view schematically illustrating the sensing head of the example organ surface ultrasound probe of FIG. 9 with an extended transducer.

FIG. 10A is a diagram schematically illustrating the extension of transducer 276 towards adhesive layer 581 within and relative to bladder 598 by actuator 584 while bladder 598 is inflated beyond cavity 575. Such movement results in transducer 276 moving in the direction indicated by arrow 615 and results in a change in the location of the volume being imaged by probe 524. An example illustrated, transducer 276 is moved from a first position in which transducer 276 is space from surface 34 of organ 36 by a first distance D1 (shown In FIG. 9) to a second position in which transducer 276 is spaced from surface 34 of organ 36 by a smaller distance D2 (shown in FIG. 10A)

In one implementation, actuator 584 includes a telescopic portion which may be extended to extend transducer 276. Prior to moving acoustic coupler 580 to the inactive state in which it is fully recessed within cavity 575, actuator 584 may retract transducer 276 by moving transducer 276 in a direction opposite to that indicated by arrow 615. Thereafter, bladder 598 may be deflated so as to be once again recessed within cavity 575 as shown in FIG. 8. At such time, sensing head 572 will have a reduced profile to facilitate extraction through a tube or trocar.

Figure 10B:
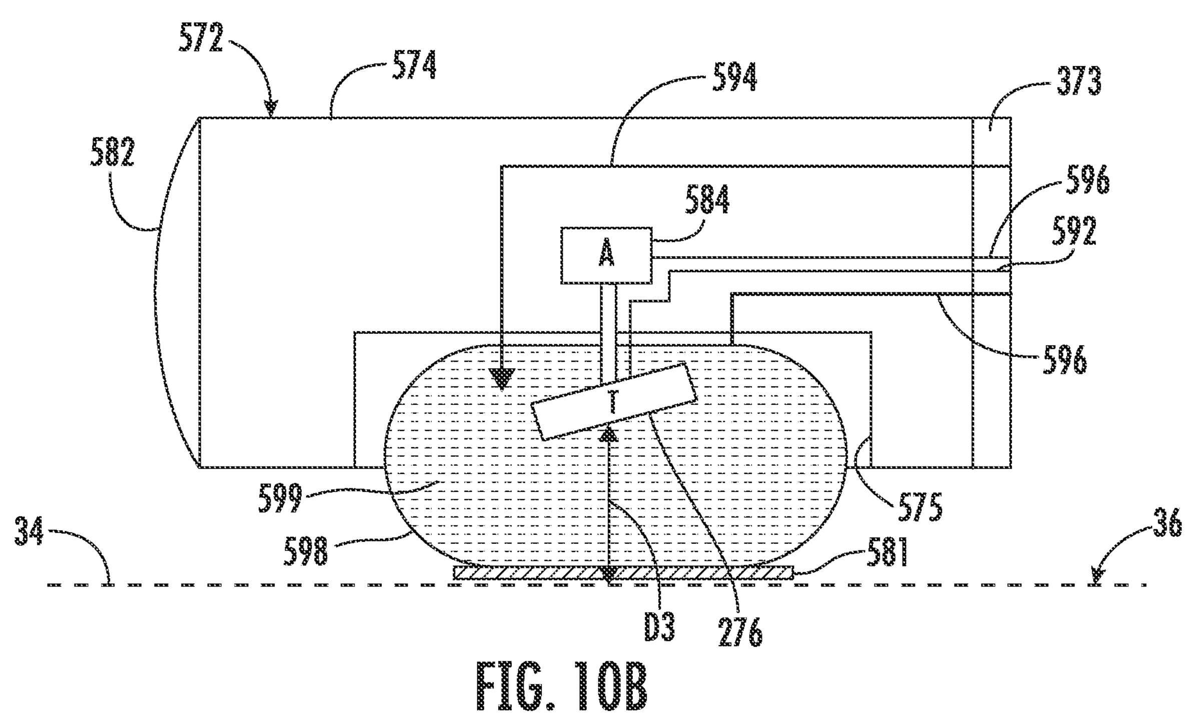
FIG. 10B is a sectional view schematically illustrating the sensing head of the example organ surface ultrasound probe of FIG. 9 with the bladder in a second inflated state.

FIG. 10B is a diagram illustrating the further inflation of bladder 598 with food coupling medium 599 to increase the spacing separating transducer 276 and surface 34 of organ 36. Probe controller 600 may output control signals causing inflation of bladder 598 from the first amount of inflation shown in FIG. 9 to the second grader amount of inflation shown in FIG. 10B. In FIG. 9, bladder 598 projects beyond cavity 575 to space transducer 276 from surface 34 of organ 36 by the distance D1. In FIG. 10B, bladder 598 projects beyond cavity 575 by a greater distance to space transducer 276 from surface 34 of organ 36 by the distance D2 which is greater than distance D1. In some implementations, both the positioning of transducer 276 and inflation of bladder 598 may be controlled to position transducer 276 at a desired distance or spacing from surface 34. In some implementations, transducer 276 may not be extendable retractable, wherein the spacing of transducer 276 from the surface 34 is controlled by the selective inflation or deflation of bladder 598.

Figure 11:
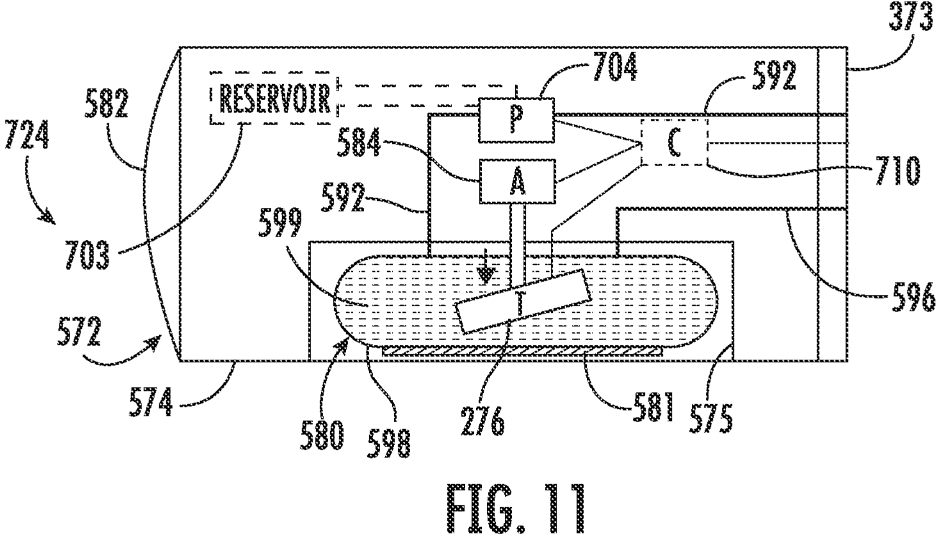
FIG. 11 is a sectional view schematically illustrating portions of an example organ surface ultrasound probe.

FIG. 11 is a diagram schematically illustrating portions of an example organ surface ultrasound probe 724. FIG. 11 illustrates an example of how many of the components of the probe to be locally located on the sensing head itself. Probe 724 is similar to probe 524 described above with respect to FIGS. 8-10 except that probe 724 additionally comprises reservoir 703, pump 704 and controller 710. Those remaining components of probe 724 which correspond to components of probe 524 or numbered similarly and/or are shown in FIGS. 8-10. For example, probe 724 additionally comprises the external probe control system 586 shown in FIG. 8.

In some implementations, reservoirs 603, 703, pumps 604, 704 and controllers 610, 710 may cooperate and share duties with respect to the control and regulation of the sensing head 572. For example, in some implementations, reservoir 703 may provide a smaller local volume of fluid for quicker response times, whereas reservoir 603 provides a larger supply or a larger storage chamber for larger changes to the extent of inflation of bladder 598. Pump 604 may still be employed to move fluid through the passive heat extractor 606 and/or to supply additional fluid from the supplemental reservoir 603. Probe controller 610 may control those components of system 586 such as valve 609 and active heat exchanger 608, whereas controller 710 locally controls pump 704 and actuator 584.

In some implementations, given the local provision of reservoir 703, pump 704 controller 710 on or within sensing head 572, external probe control system 586 may omit reservoir 603, pump 604 and/or probe controller 610. In such implementations, pump 704 may move fluid through passive heat exchanger 606. In some implementations, controller 710 may control valves 609. In such implementations, valves 609-1 and 609-2 may be locally provided as part of housing 574. In some implementations, controller 710 may output control signals controlling the operation of active heat exchanger 608 or may output requests which are transmitted to a separate external controller which controls active heat exchanger 608.

Reservoir 703 comprises a chamber, container or other volume containing a supply of the fluid serving as acoustic coupling medium 599. Reservoir 603 supplies fluid for those times during which bladder 598 is being inflated with additional fluid. Reservoir 603 receives fluid during those times during which bladder 598 is being deflated.

Pump 704 operates similar to pump 604, moving fluid. In the example illustrated, pump 704 moves fluid along fluid supply line 594 into bladder 598. In other implementations, pump 704 may be associated with fluid return line 596, drawing fluid from the interior of bladder 598. As indicated above, pump 704 make operate in cooperation with pump 604.

Controller 710 comprises a processing unit and associated instructions for locally controlling the operation of pump 704, actuator 584 and transducer 276. Controller 710 may receive pressure data from pressure sensor 587 (shown in FIG. 8) and temperature data from temperature sensor 588 (shown in FIG. 8). Based upon such data, controller 710 may control the operational pump 704 and valve 609. As indicated above, controller 710 may share duties with probe controller 610.

Figure 12:
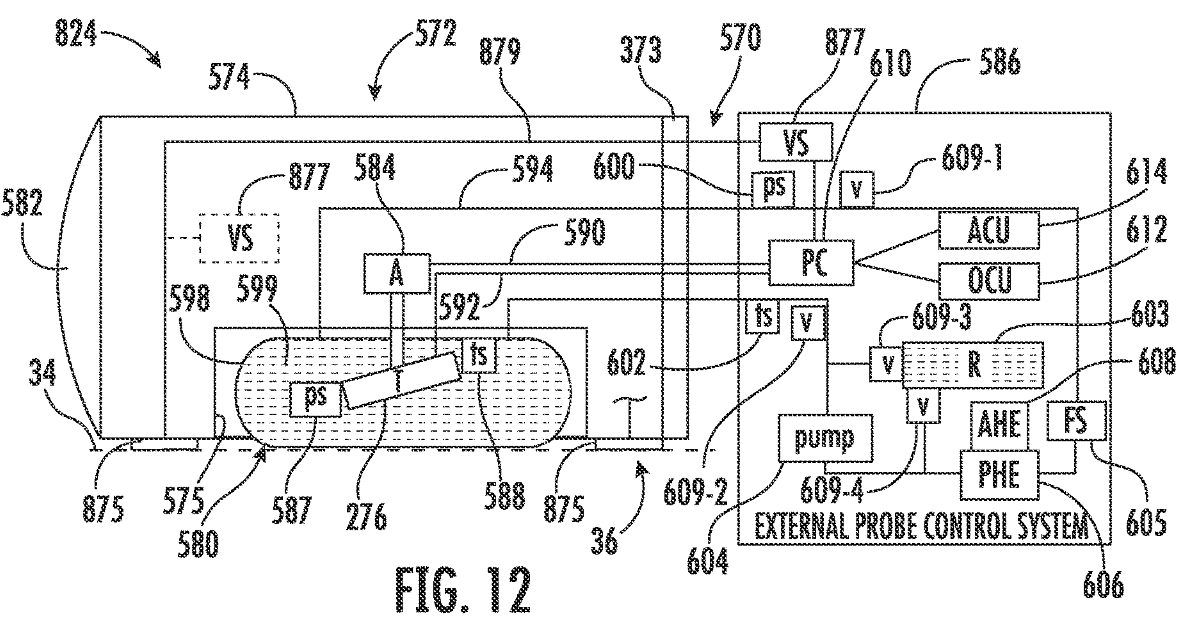
FIG. 12 is a sectional view schematically illustrating portions of an example organ surface ultrasound probe.

FIG. 12 is a diagram schematically illustrating portions of an example organ surface ultrasound probe 824. FIG. 12 illustrates an example of how the sensing head of a probe may be retained in place relative to an organ using grippers rather than relying upon an adhesive layer on the acoustic coupler. Probe 824 is similar to probe 524 described above except that sensing head 572 additionally comprises grippers 875 and that external probe control system 586 additionally comprises vacuum source 877. The remaining components of probe 824 which correspond to components of probe 524 are numbered similarly and/or are shown in FIGS. 8-10. In some implementations, sensing head 572 of probe 824 may include locally provided components as described above with respect to probe 724 in FIG. 11.

Gripper 875 comprise mechanisms configured to releasably grasp or hold onto the exterior surface 34 of organ 36, retaining cavity 575 in place relative to a region of interest of organ 36. Due to this retention, adhesive layer 581 may be omitted. In some implementations, adhesive layer 581 may be retained for additional retention of sensing head 572.

In the example illustrated, gripper 875 comprises a suction cup or multiple suction cups configured to grip surface 34 through the use of suction. In some implementations, gripper 875 comprise a series of spaced gripper elements situated about cavity 575. In some implementations, gripper 875 comprises a single continuous annular gripper extending about cavity 575. Gripper 875 is pneumatically coupled to vacuum source 877 via an airline 879. Airline 879 may extend through housing 574 and through bundle 570 to vacuum source 877.

Vacuum source 877 may comprise a pump or other device for actively creating a vacuum, negative pressure, within gripper 875. Vacuum source 877 is under the control of probe controller 610 which controls the creation of vacuum. When sensing head 572 is to be withdrawn from surface 34, probe controller 610 may output control signals causing vacuum source 877 to reduce the suction or to discontinue supplying the vacuum, permitting grippers 875 to release surface 34. As shown by broken lines, in some implementations, vacuum source 877 may be locally located on sensing head 572. In such implementations, the local vacuum source 877 may be under the control of probe controller 610 or under the control of a local controller such as controller 710 described above. In some implementations, vacuum source 877 and airline 879 may be omitted, wherein grippers 875 rely upon a passively created suction which occurs as elastomeric suction cups of grippers 875 are compressed against surface 34. In some implementations, gripper 875 may alternatively comprise a layer of adhesive provided on housing 574 about cavity 575 for bonding to surface 34 or may comprise other structures for engaging surface 34, such as barbs and the like.

Figure 13:
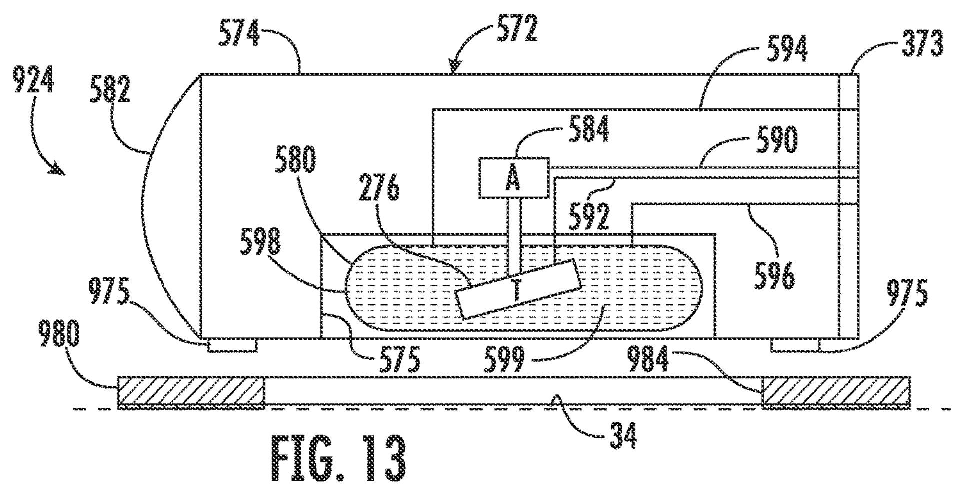
FIG. 13 is a sectional view schematically illustrating portions of an example organ surface ultrasound probe disconnected from an organ conformable panel secured to an organ surface.
Figure 14:
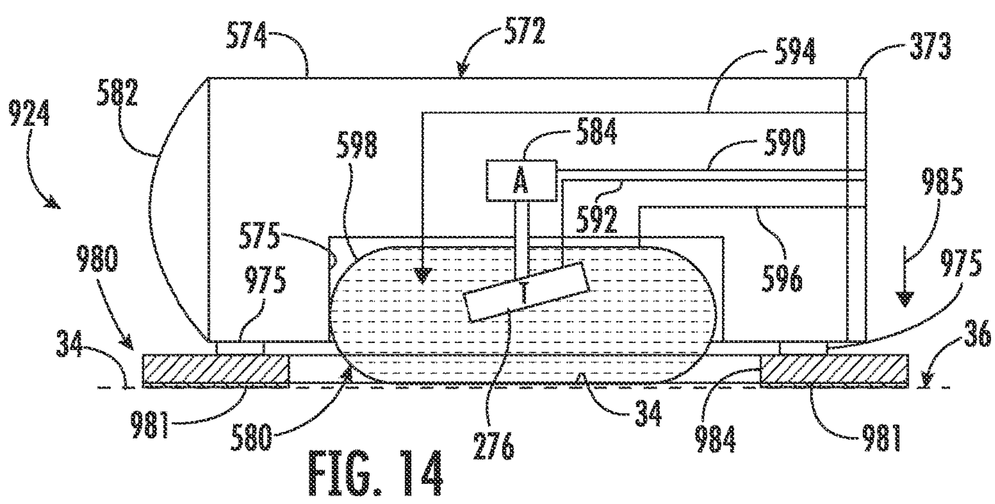
FIG. 14 is a sectional view schematically illustrating the portions of the example organ surface ultrasound probe of FIG. 13 connected to the organ conformable panel which is secured to the organ surface.

FIGS. 13 and 14 are diagrams schematically illustrating portions of an example organ surface ultrasound probe 924. FIGS. 13 and 14 illustrate an example of how a sensing head may be releasably secured to an organ conformable panel secured to an organ, wherein the organ conformable panel acts as a landing pad and retains the sensing head in place. Probe 924 is similar to probe 524 described above except that sensing head 572 additionally includes couplers 975 and organ conformable panel 980. The remaining components of probe 924 which correspond to components of probe 524 are numbered similarly or are shown and described above with respect to FIGS. 8-10. As with probe 524, probe 924 comprises sensing head 572 which is releasably connectable to bundle 570 which provides electrical and fluid connections between sensing head 572 and external probe control system 586.

Couplers 975 comprise structures extending along or from the exterior of housing 574 which are configured to connect to organ conformable panel 980. In some implementations, couplers 975 are configured to releasably connect to organ conformable panel 980. In some implementations, couplers 975 include actuatable or spring biased hooks, pins or the like for latching onto organ conformable panel 980. In some implementations, couplers 975 comprise pins or other structures which provide a friction or press fit within corresponding apertures provided in the surface of organ conformable panel 980. In some implementations, couplers 975 comprise regions of adhesive for bonding to a top surface of organ conformable panel 980.

In some implementations, couplers 975 comprise magnets or magnetically attractable material such as a ferrous material secured along an exterior of sensing head 572 or within sensing head 572, but sufficiently close to the exterior to be magnetically held by magnets or magnetically attractable material provided on organ conformable panel 980. For example, one of couplers 975 and organ conform panel 980 may comprise a magnet, whereas the other of couplers 975 and organ conformable panel 980 comprises a magnetically attractable material. In some implementations, couplers 975 and organ conformable panel 980 comprise magnets, of opposite polarity.

In some implementations, an electromagnet may be provided and selectively electrically powered to turn the electromagnet on and off to control the connection of sensing head 572 to organ conformable panel 980. In one implementation, couplers 975 may comprise an electromagnet for selectively magnetically holding a magnet or magnetically attractable material provided on organ conformable panel 980. In such an implementation, the electromagnet forming couplers 975 may be electrically controlled by electrical switch under the control of probe controller 610 via electrically conductive lines of bundle 570.

Organ conformable panel 980 comprises a panel of bendable, flexible or, in some implementations, elastic material, such that the lower surface of panel 980 may change shape to match or closely conform to the shape of the underlying portions of the exterior surface 34 of organ 36. In some implementations, panel 980 may be provided in sections which are positioned on the organ adjacent to one another. Organ conformable panel 980 may be secured to surface 34 by an adhesive layer.

In some implementations, adhesive layer 981 may comprise a layer of adhesive coated upon housing 574 or may comprise adhesive supported by a substrate such that the adhesive layer form a two-sided tape which is bonded to the bottom or organ facing side of panel 980. Panel 980 may or may not be reusable. In some implementations, adhesive layer 981 may be sprayed upon panel 980. In some implementations, adhesive layer 981 may be first applied to surface 34 prior to panel 980 being positioned into contact with adhesive layer 981 and being adhered for example, in some implementations, adhesive layer 981 may be coated, sprayed or otherwise applied to surface 34 followed by the positioning of panel 980 against the adhesive layer. In some implementations, adhesive layer 981 may comprise a fibrin sealant or similar adhesive, such as Tisseel, commercially available from Baxter Healthcare Healthcare. In yet other implementations, adhesive layer 981 may have other compositions. In some implementations, the adhesive layer may be thickness of no greater than 2 mm, and in some implementations, no greater than 1 mm.

Panel 980 includes an aperture 984 sized to receive bladder 598 upon inflation of bladder 598 such that the lower surface of bladder 598 may be brought into contact with surface 34 through aperture 984. Aperture 984 provides a window by which acoustic coupler 580 may be brought into acoustic contact with the exterior surface 34 of organ 36. Aperture 984 is further sized or shaped such that couplers 975 may engage the top surface of panel 980 while cavity 575 is at least partially aligned with aperture 984.

Panel 980 may be pre-mounted at a desired location on exterior surface 34 of organ 36. In some implementations, panel 980 may be rolled during insertion into the patient and deployed by laparoscopic tools at the desired location. As noted above, in some implementations, different sections of panel 980 may be sequentially mounted to the organ 36 using laparoscopic tools. Thereafter, sensing head 572 may be inserted into the patient through a tube, trocar and oriented opposite to panel 980 with cavity 575 sufficiently aligned with after 984 such that acoustic coupler 580, upon inflation, will pass through aperture 984 into contact with exterior surface 34 of organ 36. Once properly aligned, sensing head 572 may be lowered onto panel 980 in the direction indicated by arrow 985 such that couplers 975 engage panel 980. Upon completion of the medical procedure, sensing head 572 may be separated from panel 980 and withdrawn. Sensing head 572 may be subsequently remounted to the panel 980.

Figures 15, 16, 17, 18:
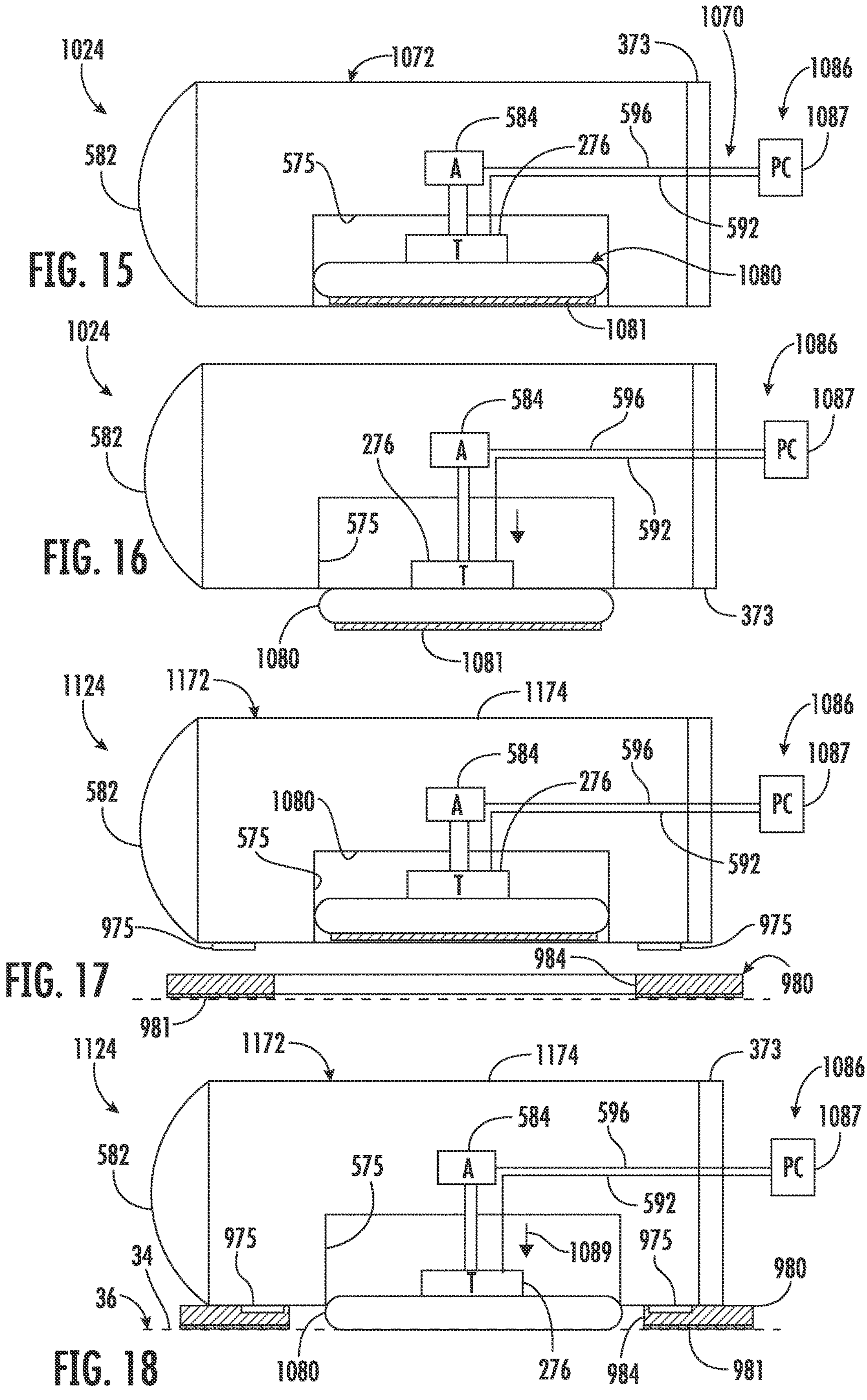
FIG. 15 is a sectional view schematically illustrating portions of an example organ surface ultrasound probe with an acoustic coupler retracted within a sensing head.
FIG. 16 is a sectional view schematically illustrating the portions of the example organ surface ultrasound probe of FIG. 15 with the acoustic coupler projecting from the sensing head.
FIG. 17 is a sectional view schematically illustrating portions of an example organ surface ultrasound probe with an acoustic coupler retracted within a sensing head and with the sensing head disconnected from an organ conformable panel.
FIG. 18 is a sectional view schematically illustrating the portions of the example organ surface ultrasound probe of FIG. 17 with the sensing head connected to the organ conformable panel and with the acoustic coupler projecting from the sensing head through the organ conformable panel.

FIGS. 15 and 16 are diagrams schematically illustrating portions of an example organ surface ultrasound probe 1024. FIGS. 15 and 16 illustrate an example of how an actuator may move a transducer to concurrently move an associated acoustic coupler into acoustic contact with a surface of an organ. Probe 1024 comprises bundle 1070, sensing head 1072, and external probe control system 1086 comprising probe controller 1087.

Bundle 1070 comprises one or more electrical wires, electrical traces of a flexible circuit or the like electrically connecting sensing head 1072 to probe controller 1087 of external probe control system 1086. As with bundle 570, the wires or flexible circuit of bundle 1070 may be grouped and contained within outer sleeve which is removably releasably coupled to insertion shaft 160 (described above). As a result, following the positioning of insertion head 1072 and its retention with respect to the organ, insertion shaft 160 may be withdrawn and separated from bundle 1070, leaving bundle 1070 in place connecting insertion head 1072 to probe controller 1087.

Sensing head 1072 is similar to sensing head 572 except that transducer 276 has a lower face 1074 affixed to acoustic coupler 1080 such that movement of transducer 276 by actuator 584 results in concurrent movement of acoustic coupler 1080. Acoustic coupler 1080 may comprise a solid or semisolid acoustic coupling medium. In some implementations, acoustic coupler 1080 may comprise a bladder, similar to bladder 598, containing in acoustic medium or agent in the form of a liquid. In some implementations, acoustic coupler 1080 may have a construction similar to that described above with respect to acoustic coupler 180 or acoustic coupler 580. In the example illustrated, acoustic coupler 1080 comprises an adhesive layer 1081, similar to adhesive layer 581, for bonding to the exterior surface 34 of organ 36 (shown in FIG. 1).

FIG. 15 illustrates actuator 584 positioning transducer 276 in a retracted position within cavity 575 such that acoustic coupler 1080 and adhesive layer 1081 are also at least partially recessed or retracted into cavity 575. In the example illustrated, transducer 276 is retracted to a position such that acoustic upper 1080 and adhesive layer 1081 are completely retracted within cavity 575. As a result, sensing head 1072 may be more easily passed through a tube trocar during insertion into the patient.

As shown by FIG. 16, once sensing head 1072 has been properly positioned into close proximity to and opposite to a targeted portion of the exterior surface 34 of organ 36, probe controller 610 (shown in FIG. 8) may output control signals causing actuator 584 to extend or move transducer 276 in the direction indicated by arrow 1085 until acoustic coupler 1080 has been brought into acoustic contact with the exterior surface 35 of organ 36. Such contact may be retained with adhesive layer 1081. In the example illustrated, transducer 276 is illustrated as being extended such that the substantially the entirety of acoustic coupler 1080 extends beyond cavity 575. At the same time, transducer 276 remains protected within cavity 575. In other scenarios, transducer 276 may at least be partially extended beyond cavity 575 or acoustic coupler 1080 may be in contact with surface 34 yet partially within cavity 575. Because actuator 584 is used to reposition both transducer 276 and acoustic coupler 1080, acoustic coupler 1080 may be formed from a solid or semisolid material, or acoustic upper 1080 may comprise a fluid within a bladder that need not be inflated or deflated. As a result, sensing head 1072 and external probe control system 1086 may be simplified, omitting components those fluid related components such as reservoir 603 and pump 604.

FIGS. 17 and 18 are diagrams schematically illustrated portions of an example organ surface ultrasound probe 1124. FIGS. 17 and 18 illustrate an example of how a sensing head may be mounted to an organ conformable panel serving as a landing pad and how an actuator may move a transducer to concurrently move an associated acoustic coupler through an aperture of the organ conformable panel into acoustic contact with a surface of an organ. Probe 1124 comprises sensing head 1172 and organ conformable panel 980 (described above with respect to probe 924).

Sensing head 1172 is similar to sensing head 1072 except that sensing head 1172 additionally includes couplers 975 (described above with respect to probe 924). As with sensing head 572 of probe 924 described above, couplers 975 secure housing 1174 to the top surface of organ conformable panel 980. In some implementations, couplers 975 are configured to releasably connect to organ conformable panel 980.

Panel 980 may be pre-mounted at a desired location on exterior surface 34 of organ 36. In some implementations, panel 980 may be rolled during insertion into the patient and deployed by laparoscopic tools at the desired location. Thereafter, sensing head 1172 may be inserted into the patient through a tube or trocar and oriented opposite to panel 980 with cavity 575 sufficiently aligned with aperture 984 for acoustic coupler 1082 be lowered through aperture 984. Once properly aligned, sensing head 1172 may be lowered onto panel 980 such that couplers 975 engage panel 980 as shown in FIG. 18. Thereafter, probe controller 1087 may output control signals causing actuator 584 to move transducer 276 towards the opening of cavity 575 in the direction indicated by arrow 1089 to move acoustic coupler 1080 through aperture 984 into contact with exterior surface 34 of organ 36 as also shown by FIG. 18.

Once acoustic coupler 1080 has been positioned in acoustic contact with the exterior surface 34 of organ 36, probe controller 1087 may transmit control signals to transducer 276 via electrical line 592 to initiate ultrasound sensing. Upon completion of the medical procedure, sensing head 572 may be separated from panel 980 and withdrawn. Sensing head 1172 may be subsequently remounted to the panel 980 which may remain in place on organ 36 despite the earlier withdrawal of sensing head 1172. Because panel 980 and couplers 975 cooperate to retain sensing head 1172 and acoustic coupler 1080 in place relative to organ 36, adhesive layer 1081 may be omitted.

FIGS. 19 and 20 are diagrams schematically illustrating portions of an example organ surface ultrasound probe 1224. FIGS. 19 and 20 illustrate an example of how a sensing head of an organ surface ultrasound probe may utilize a conformable transducer. FIGS. 19 and 20 further illustrate an example of how the sensing head may be releasably secured to a conformable panel serving as a landing pad on the organ. Ultrasound probe 1224 comprises sensing head 1272, conformable panel 980 (shown and described above with respect to FIG. 13), bundle 570, and external probe control system 586 (bundle 570 and system 586 being shown and described above with respect to FIG. 8).

Sensing head 1272 comprises housing 1274, coupling interface 1273, transducer 1276, acoustic coupler 1280, actuator 1284, couplers 1275 and coupler actuators 1279. Housing 1274 is similar to housing 574 in that housing 1274 extends along a longitudinal axis from a coupling interface 1273 to a tip 582. Tip 582 may be elastomeric and blunt. In some implementations, tip 582 may have other shapes or formed from other materials. Housing 1274 further comprises a cavity 575 from which transducer 1276 may extend or project. As with housing 574, housing 1274 housing contains those components of sensing head 1272.

Coupling interface 1273 releasably connects or couples sensing head 1272 to insertion shaft 160 (described above). Coupling interface 1273 may further provide releasable coupling to various fluid and electrical lines of bundle 570. In some implementations, bundle 570 may alternatively be non-removably connected to the corresponding electrical and fluid lines of sensing head 1272 such as when insertion shaft 160 is separated from coupling interface 1273 withdrawn while leaving bundle 570 connected to sensing head 1272.

Transducer 1276 comprises a conformable transducer configured to be positioned in conformable and acoustic contact with portions of exterior surface 34 of organ 36. Transducer 1276 may be in the form of ultrasound transceiver for generating and emitting ultrasound waves and detecting the reflection of such waves, wherein transducer 1276 outputs electrical ultrasound data signals which are transmitted to probe controller 610 and/or display unit 32 (described above). Transducer 1276 comprises flexible substrate 1300, transducer elements 1302-1 . . . **1302-*n* (collectively referred to as transducer elements 1302) and transducer element position indicators 1304** (each being schematically illustrated with an "*").

Flexible substrate 1300 comprises one or more layers of one or more materials forming a flexible, bendable or deformable panel that supports transducer elements 1302 and transducer element position indicators 1304. Substrate 1300 may further support electrically conductive wires or traces for powering and communicating with transducer elements 1302 and transducer element position indicators 1304. Such electrically conductive wires or traces connect via electrical contact pads or the like to electrical line 1292 which may comprise multiple distinct electrical lines for connection to probe controller 610 and/or display unit 32 via bundle 570. Flexible substrate 1300 is sufficiently flexible so as to conform to any surface profile irregularities or undulations of exterior surface 34 of organ 36 as shown in FIG. 21.

In some implementations, flexible substrate 1300 is fluidly sealed against the sides of the interior cavity 575 and is permitted to slide within cavity 575 between the different positions shown in FIGS. 19 and 20. In some implementations, the outer perimeter flexible substrate 1300 is sealed and affixed to the interior sides of cavity 575, wherein flexible substrate 1300 bows inwardly into cavity 575 to retract acoustic coupler 1280 or bows outwardly away from cavity 575 to extend acoustic coupler 1280. In some implementations, flexible substrate 1300 is fixed proximate to the exterior of housing 1274 with acoustic coupler 1280 beyond cavity 575, wherein the amount of fluid 1297 within cavity 575 may be controlled and adjusted to control the degree of stiffness or bendability of flexible substrate 1300.

Transducer elements 1302 comprise a two-dimensional array of such elements supported by flexible substrate 1300. Each transducer element 1302 may comprise an ultrasound transceiver. In some implementations, each transistor element 1302 may comprise a PZT transducer.

Transducer element position indicators 1304 comprise sensors supported by flexible substrate 1300 which are configured to output electrical signals indicating the positioning and/or orientation of those nearby transducer elements 1302. Such electrical signals are transmitted to probe controller 610 and/or display unit 32 for carrying out phase correction with respect to the individual transducer elements 1302. Such signals further indicate the current steering of the field-of-view provided by transducer elements 1302.

In some implementations, transducer element position indicators 1304 may comprise strain sensors which output electrical signals indicating any bending of flexible substrate 1300 which correspondingly indicates or may be used to determine the angular orientation and positioning of nearby transducer elements 1302. In some implementations, transducer element position indicators 1304 may comprise angle sensors, rotary encoders that operate according to a light barrier principal. In some implementations, transducer element position indicators 1304 may comprise static sensors, such as those senses that use inductive or capacitive measuring, or electrical resistance measuring (potentiometers).

In some implementations, transducer element position indicators 1304 may comprise optical angle sensors which can statically measure the rotation angle using an optical medium with an embossed structure that diffracts light according to the Fresnel's formula. Measurement may be conducted by at least two photodiodes (a measuring probe and reference diode). With a stacked construction, the sensor may measure up to more than 270°. The optical angle sensors rely upon the angle-dependent transmission of a light ray having a defined wavelength through an optical interface between material showing different refractive indexes. For example, a depression in the surface of a slice, such as a silicon wafer, may be formed by chemical etching. A laser diode may direct a beam at the depression from different directions. Depending upon the wafer's rotation angle, light may be refractive multiple times, enabling the determination of an angular position using such photodiodes.

In some implementations, the angular positions of the individual ultrasound transducer elements may be optically based using cameras or the like. In some implementations, the angular positions of the individual ultrasound transducer elements may be determined based upon signals from such ultrasound transducer elements over time. Individual signals produced by individual ultrasound transducer elements at a first point in time may be compared to images or individual signals produced by the same ultrasound transducer elements at a second point time to estimate positional changes of the transducer elements and to estimate the current position of such individual transducer elements. For example, in some implementations, a processing method such as correlation may be used to detect positional changes of the individual ultrasound transducer elements. For example, in some implementations, changes in the positioning of transducer elements may result in images becoming blurred, wherein those particular corrections applied to such signals to resolve or enhance the image may also indicate the changes in the positions of the transducer elements that caused the blurred images are signals.

Acoustic coupler 1280 acoustically connects or couples transducer elements 1302 to exterior surface 34 of organ 36.

Acoustic coupler 1280 may have an acoustic coupling medium or agent similar to that described above with respect to acoustic coupler 580 or acoustic coupler 1080. In some implementations, acoustic coupler 1280 may comprise a solid or semi solid material such as a gel. One example of such an acoustic coupling medium is a polyacrylamide gel. This gel may be contained within an outer encasement or film. In some implementations, the acoustic coupling medium may comprise a liquid or fluid such as water or solutions largely composed of water, when the water or other solution is contained within a bladder. The outer encasement, film, or bladder may be partially received within cavity 575 projecting from a bottom side of housing 1274, wherein the encasement, film, or bladder containing the acoustic coupling medium is in contact or is otherwise acoustically coupled to transducer elements 1302. In some implementations, the transducer element 1302 may be at least partially immersed within the acoustic coupling medium of the acoustic coupler. For example, a bottom face and sides of the transducer elements 1302 may be directly adjacent to the acoustic coupling medium. In some implementations, the acoustic coupling medium may be more of a solid, wherein the transducer element 1302 a top face of the acoustic coupler 1280.

In some implementations, the acoustic coupler 1280 may comprise a hydrogel. In some implementations, the hydrogel may include mechanical anchor points located on or embedded in the hydrogel, wherein the anchor points mount and secure transducer elements 1302 to or within the hydrogel. In some implementations, the hydrogel may include electrically conductive traces imprinted upon or embedded in the hydrogel, wherein the electrically conductive traces facilitate electrical powering of transducer element 1302 and transmission of electrical signals to and from transducer element 1302. Such electrical signals may be control signals for controlling transducer elements 1302 as well as data signals representing or based upon sensed reflected ultrasound/mechanical waves.

Actuator 1284 moves acoustic coupler 1280 between a retracted or recessed position within cavity 575 and an extended position beyond cavity 575 for making conformable contact with exterior surface 34 of organ 36. In the example illustrated, actuator 1284 comprises fluid supply line 1294 and fluid return line 1296. Fluid supply line 1294 and fluid return line 1296 are similar to fluid supply line 594 and fluid return line 596, respectively, described above except that such lines circulate fluid 1297 across a backside of flexible substrate 1300 within cavity 575. Rather than inflating bladder 598 as with probe 524, the fluid being circulated by lines 1294 and 1296 differentially fills cavity 575 to controllably move flexible substrate 1300 and the supported transducer elements 1302. In some implementations, fluid 1297 contained within cavity 575 may be further contained within a surrounding bladder position within cavity 575 behind flexible substrate 1300. In such an implementation, the ports of fluid line 1294 and 1296 are sealed to the bladder and communicate with the interior of the bladder.

Because fluid 1297 does not serve as an acoustic coupling medium, fluid 1297 need not necessarily be the same type of fluid as acoustic coupling medium 599. In some implementations, the fluid club 97 may comprise water. In some implementations, the fluid may comprise a gas or air.

Control over the circulation of fluid and the amount of fluid being supplied to or withdrawn from cavity 575 is controlled by external probe control system 586 controlling the operation of pump 604 and valves 609 as described above with respect to FIGS. 8-10. When additional fluid is to be supplied to cavity 575 (or from the bladder) to move transducer 1276 towards the extended position, fluid 1297 may be drawn from reservoir 603. When fluid is to be withdrawn from cavity 575 (or the bladder), fluid 1297 may be extracted and stored in reservoir 603. External probe control system 586 may further control or regulate the temperature of fluid 1297 using passive heat extractor 606 and active heat extractor 608 as described above to cool or otherwise regulate the temperature of transducer elements 1302.

Couplers 1275 are configured to interact with conformable panel 982 secure sensing head 1272 in place relative to the underlying exterior surface 34 of organ 36. Couplers 1275 are similar to couplers 975 described above except that couplers 1275 are movable between a retracted state or position shown in FIG. 19 and an extended state or position shown in FIG. 20. Couplers 1275 may interact with conformable panel 980 in a manner similar to that described above with respect to interaction between couplers 975 and conformable panel 980.

Coupler actuators 1279 comprise devices configured to at least controllably deploy couplers 1275 to an extended state for engaging conformable panel 980. In the example illustrated, actuators 1279 are configured to extend and retract couplers 1275 between the extended and retracted positions. In the example illustrated, couplers 1279 comprise cylinders 1308, Pistons 1310, and fluid line 1312. Cylinders 1308 are formed within or supported by housing 1274. Cylinders 1308 slidably receive and guide pistons 1310. Pistons 1310 are connected to rods that are connected to couplers 1275.

Fluid line 1312 is connected to each of cylinders 1308 and is further connected to each of fluid supply line 1294 and fluid return line 1296. Fluid supply line 1294 may direct fluid into cylinder 1308 to drive pistons 1310 and to move couplers 1275 to the extended position. Fluid return line 1296 may further withdraw fluid from cylinders 1308 to retract pistons 13 10 and to move couplers 1275 to a retracted position. In other implementations, the hydraulic piston-cylinder assemblies may be actuated with other fluid line architectures. In other implementations, coupler actress 1279 may comprise other forms of actuator such as electric solenoids, piezoresistive elements or the like.

FIGS. 19 and 20 illustrate the movement of transducer 1276 between the extended and retracted positions. FIG. 19 illustrates sensing head 1272 in an inactive state in which acoustic coupler 1280 is recessed or retracted within cavity 575. Because acoustic coupler 1280 is retracted within housing 1274, sensing head 1272 has a reduced size or diameter, facilitating movement of sensing head 1272 through a tube or trocar through the outermost skin of a patient to a position proximate to organ 36.

The retracted or recessed state of acoustic coupler 1280 is achieved by probe controller 610 outputting control signals to pump 604 and valves 609 such that a greater volume of fluid is withdrawn from cavity 575 as compared to the amount of fluid being supplied to cavity 575, creating a negative pressure to move transducer 1276 to the retractable position shown in FIG. 19. In one implementation, probe controller 610 outputs control signals closing valve 609-1, opening valve 609-2, closing valve 609-3 and opening valve 609-4. Probe controller 610 further outputs control signals actuating pump 604 such that fluid is drawn from cavity 575 and directed into reservoir 603.

FIG. 20 illustrates sensing head 1272 secured to conformable panel 980 with the deployment of couplers 1275. FIG. 20 further illustrates sensing head 1272 in an active state in which acoustic coupler 1280 is extended beyond cavity 575 for positioning acoustic coupler 1280 into acoustic contact with external surface 34 of organ 36. The extended state of acoustic coupler 1280 is achieved by probe controller 610 outputting control signals such that a greater volume of fluid is supplied to cavity 575 as compared to the amount of fluid being withdrawn from cavity 575, resulting in flexible substrate 1300 either sliding within cavity 575 to move acoustic coupler 1280 through after 984 into acoustic contact with surface 34 or outwardly bowing through aperture 984 into acoustic contact with exterior surface 34. In one implementation, probe controller 610 outputs control signals opening valves 609-1 and 609-3 and closing valves 609-2 and 609-4. Probe controller 610 further outputs control signals actuating pump 604 such that fluid is drawn from reservoir 603 and directed into cavity 575. Once cavity 575 has been sufficiently filled such that acoustic coupler 1280 is in sufficient contact with organ 36, probe controller 610 may output control signals closing valve 609-3. In some implementations, probe controller 610 may further close valve 609-1 and 609-2 and discontinue the operation of pump 604. In some implementations, as described below, probe controller 610 may continue the operation of pump 604 with valve 609-1 and 609-2 open so as to circulate fluid through and across the interior of cavity 575.

In some implementations, a degree of contact of acoustic coupler 1280 is determined based upon signals from an external ultrasound sensor. In some implementations, the degree of contact may be determined based on signals from transducer 1276. In some implementations, the degree of contact may be determined based upon signals from pressure sensor 587 and/or pressure sensor 600 (shown in FIG. 12), wherein a sufficient degree of contact may be a determined based upon the sense pressure exceeding a predetermined threshold.

Once acoustic coupler 1280 has been brought into sufficient acoustic communication or contact with the external surface 34 of organ 36, probe controller 610 may output control signals to transducer 1276 to begin collecting ultrasound data for use by display unit 32 in generating image 50 (shown in FIG. 1).

Transducer 1276 may generate and emit heat during its operation. Probe controller 610 may monitor the heating up transducer 1276 based upon signals received from temperature sensor 588 and/or temperature sensor 602. Upon the detected temperature exceeding a predetermined threshold, probe controller 610, following the instructions contained in the non-transitory computer-readable medium, may output control signals initiating the circulation of fluid within bladder 598 and across transducer 276 by actuating pump 604 and opening valve 609-1 and 609-2. In some implementations, probe controller 610 may increase the extraction of heat from fluid 599 to cool transducer 1276 by operating pump 604 at a higher rate so as to circulate fluid through cavity 575 at a higher rate. In some implementations, probe controller 610 may further increase the extraction of heat from fluid 1297 to cool transducer 1276 by turning on active heat exchanger 608 or increasing the rate at which active heat changes 608 extracts heat. By monitoring the temperature of transducer 1276, directly or indirectly and by circulating fluid through cavity 575, external probe control system 586 may reduce the likelihood of damage to transducer 1276 (transducer elements 1302) from overheating and/or reduce the likelihood of harm to the patient from excessive heat.

FIGS. 22 and 23 illustrate one example construction of a conformable transducer 1376 which may be employed to serve as the flexible substrate 1300 and the transducer elements 1302 of FIGS. 19 and 20. FIG. 22 is a sectional view of the conformable transducer 1376 while FIG. 23 is a top view of the single transducer element 1402. As shown by FIG. 22, the example conformable transducer 1376 comprises PZT elements 1412 disposed above and array of islands 1414. The silicon islands 1414 are connected to one another by polyamide layer 1416. Electrical traces 1418 are formed between the silicon islands 1414 and the PZT elements 1412. Electrical traces 1420 are further formed above the PZT elements 1412. Electrical traces 1420 are covered by a backing layer 1422. This entire construction is encapsulated by layers 1424 and 1426 of parylene. Transducer element position indicators 1304, in the form of strain sensors, may be mounted upon or encapsulated within the structure between the individual transducer elements formed by the PZT elements 1412. In other implementations, the conformable transducer formed by flexible substrate 1300 and transducer elements 1302 may have other particular architectures.

Figure 24:
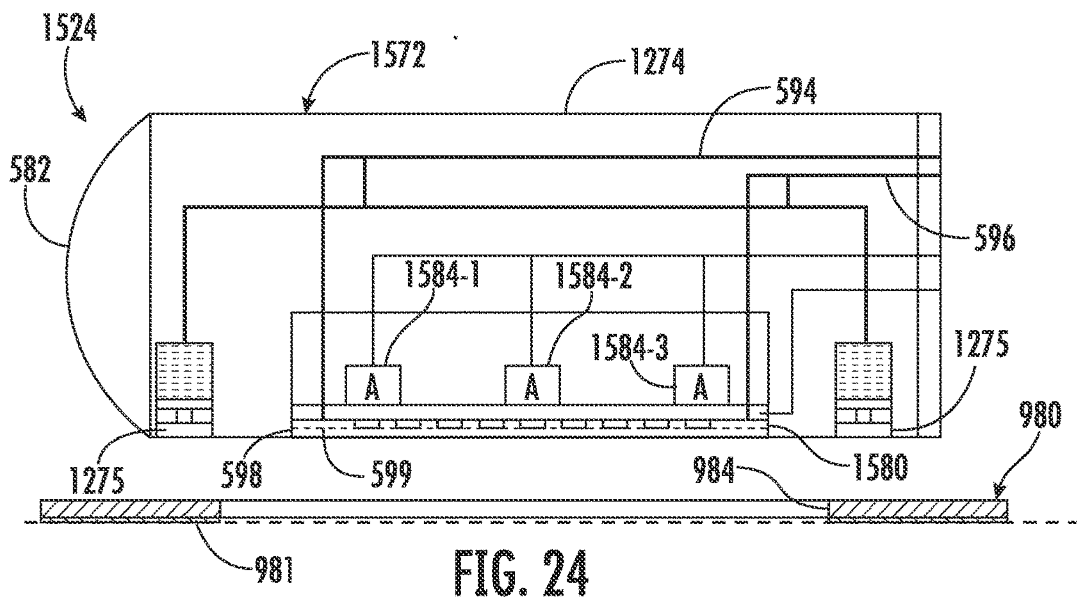
FIG. 24 is a sectional view schematically illustrating portions of an example organ surface ultrasound probe with a sensing head disconnected from an organ conformable panel that is connected to an organ surface.
Figure 25:
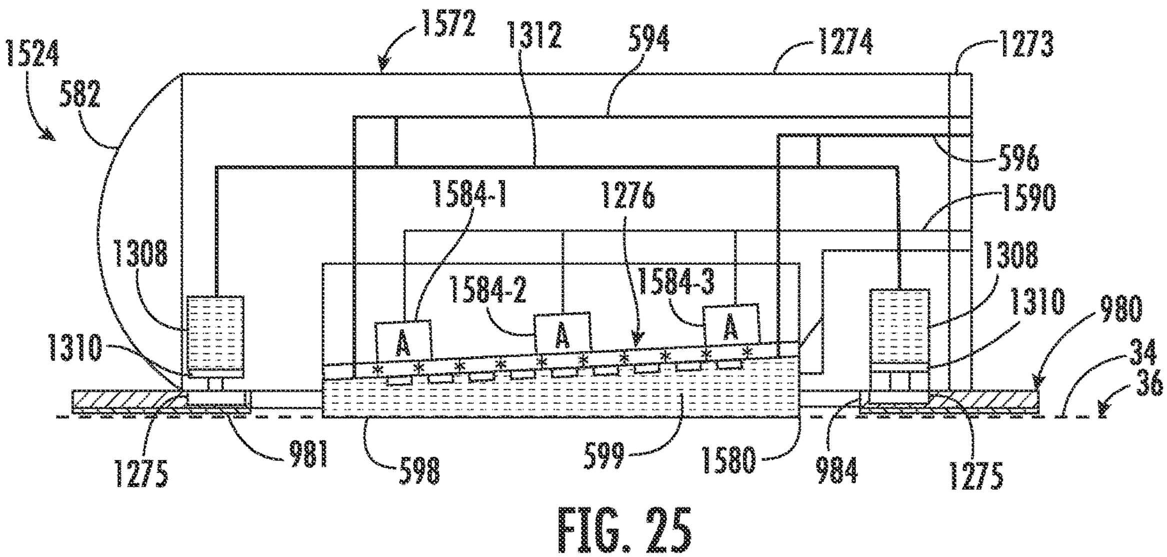
FIG. 25 is a sectional view schematically illustrating the portions of the example organ surface ultrasound probe of FIG. 24 with the sensing head connected to the organ conformable panel and with an acoustic coupler of the sensing head passing through the organ conformable panel into contact with the organ surface.

FIGS. 24 and 25 are diagrams schematically illustrating portions of an example organ surface ultrasound probe 1524. FIGS. 24 and 25 illustrate an example of how distinct portions of the flexible substrate 1300 may be differently moved or actuated to control the positioning of different transducer elements to control the field-of-view provided by the transducer elements. Probe 1524 is similar to probe 1224 described above except that probe 1524 comprises acoustic coupler 1580 in place of acoustic coupler 1280, includes fluid lines 594 and 596 (described above with respect to probe 524 in FIG. 8) and further includes actuators 1584-1, 1584-2 and 1584-3 (collectively referred to as actuators 1584). The remaining components of probe 1524 which correspond to components of probe 1224 are numbered similarly and/or are shown in at least FIGS. 12 and 19.

Acoustic coupler 1580 is similar to acoustic coupler 580 described above. Acoustic coupler 1580 comprises an inflatable bladder 598 enclosing an acoustic coupling medium 599. Fluid lines 594 and 596 supply fluid to withdraw fluid from the interior of bladder 598 to control the inflation level of bladder 598. Fluid lines 594 and 596 may further circulate fluid through bladder 598 and across transducer elements 1302 to extract heat and cool transducer elements 1302. The supply of fluid to and the circulation of fluid within bladder 598 is controlled by external probe control system 586 as described above respect to probe 524 in FIG. 8.

As shown by FIG. 24, the supply of acoustic coupling medium 599 within bladder 598 may be controlled such that bladder 598 is substantially retracted within cavity 575. In this inactive state, sensing head 1572 may be more easily passed through a tube or trocar into the patient. Once positioned into proximity with conformable panel 980, couplers 1275 made be deployed into engagement with conformable panel 980 as shown in FIG. 25, securing sensing head 1572 to conformable panel 980 which is adhesively bonded to surface 34 of organ 36.

As shown by FIG. 25, upon sensing head 1572 being secured to conformable panel 980, probe controller 610 may actuate pump 604 and valves 609 (shown in FIG. 8) to additionally inflate bladder 598 with fluid coupling medium 599 so as to move bladder 598 through aperture 984 of panel 980 and into conformable acoustic coupling contact with surface 34. Acoustic coupling medium 599 (described above with respect to probe 524) acoustically couples transducer elements 1302 to surface 34.

Actuators 1584 comprise independently controllable devices operably coupled to flexible substrate 1300 to controllably and selectively move particular portions of flexible substrate 1300 relative to one another such that individual transducer elements 1302 may be at distinct positions and orientations relative to one another. As a result, such actuators 1584 may be used to adjust the field-of-view provided by the two-dimensional array of transducer elements 1302. Actuators 1584 may be individually controlled via electrical communication lines 1590 which extend through housing 1274 and coupling interface 1273, along bundle 570 and to probe controller 610 of external probe control system 586 (shown in FIG. 8).

Figure 26:
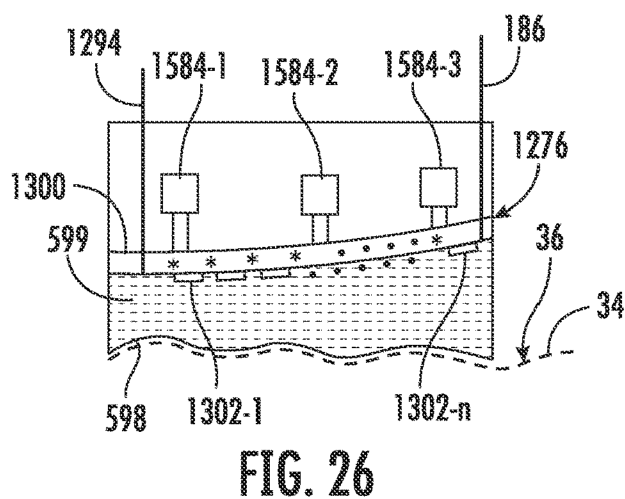
FIG. 26 is an enlarged sectional view illustrating portions of the example organ surface ultrasound probe of FIG. 25 in contact with the organ surface.

FIG. 26 is an enlarged view illustrating an example of the inflation of bladder 598 with a fluid coupling medium 599 such that bladder 598 is brought into conformable contact with surface 34 of organ 36. FIG. 26 further illustrates an example of the bending of flexible substrate 1300 by actuators 1584 to control or adjust the field-of-view provided by transducer elements 1302. In the example illustrated, the field-of-view provided by transducer element 1302 is not perpendicular to the side of sensing head 1572 or housing 1574 but is instead rotated within fluid coupling medium 599 to extend her face in directions oblique to the exterior face of housing 1274. During a medical procedure, actuators 1584 may be differently actuated to provide flexible substrate 1300 with different shapes for providing differently steered or aimed field-of-views.

In some implementations, actuators 1584 may comprise piezoelectric or piezo-resistive actuators or PZT bimorphs spaced along the flexible substrate 1300 to individually move respective portions of the substrate 1300 and to individually steer associated transducer elements 1302 of the conformable transducer 1276. Although FIGS. 24 and 25 illustrate three actuators 1584, in other implementations, additional or fewer of such actuators may be employed. In some implementations, other forms of actuation devices or structures may be employed to differently bend different portions of flexible substrate 1300.

Figure 27A:
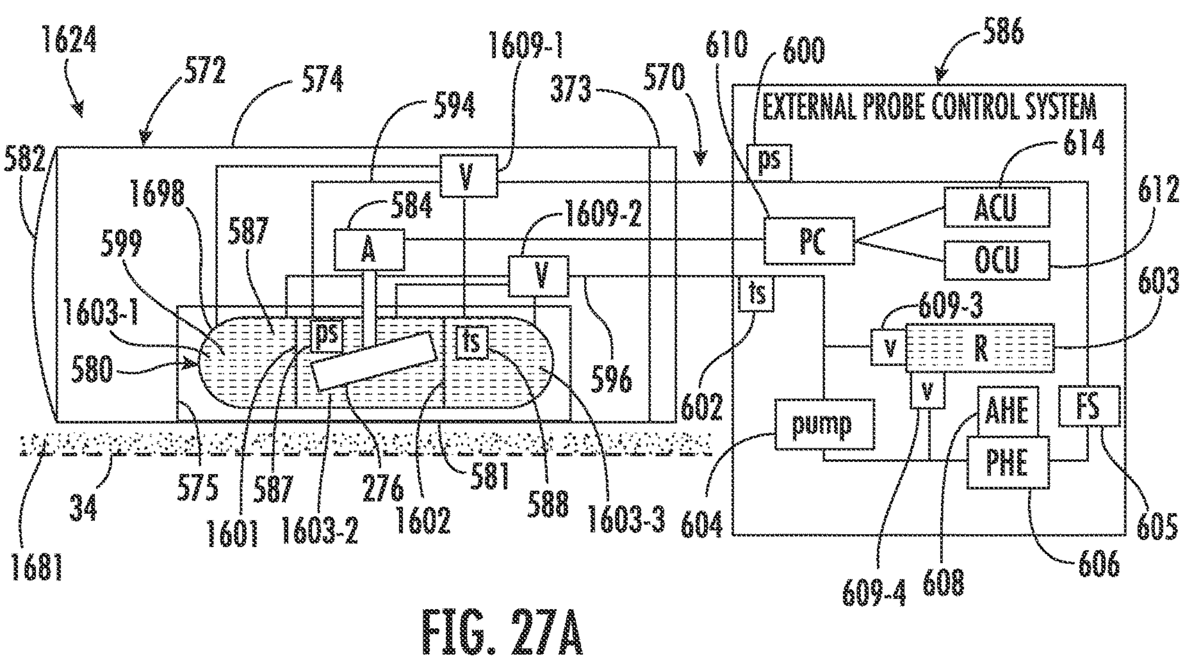
FIG. 27A is a sectional view illustrating portions of an example organ surface ultrasound probe having a compartmentalized bladder in a first inflation state.
Figure 27B:
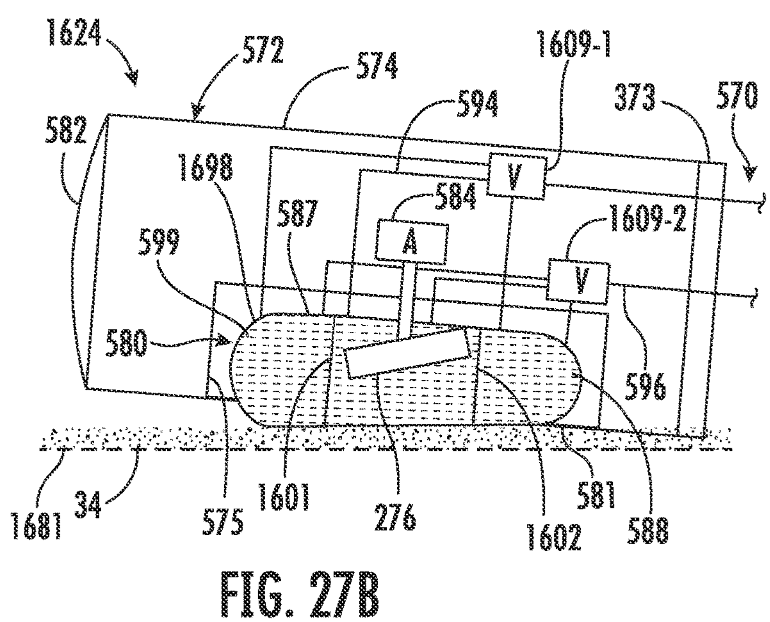
FIG. 27B is a sectional view of the organ surface ultrasound probe of FIG. 27A with the compartmentalize bladder in a second inflation state.

FIGS. 27A and 27B are diagrams schematically illustrating portions of an example organ surface ultrasound probe 1624. FIGS. 27A and 27B illustrate an example of how bladder 598 may be compartmentalized, wherein each of the compartments may be selectively and differently inflated or deflated with the fluid coupling medium 599 to control the orientation of the head 524 on the surface of the organ and to control the field-of-view of transducer 276. As shown by FIG. 27A, probe 1624 is similar to probe 524 described above except that probe 1624 comprises bladder 1698 in place of bladder 598 and comprises multidirectional or multi-output valves 1609-1 and 1609-2 in place of valves 609-1 and 609-2, respectively. Those remaining components of probe 1624 which correspond to components of probe 524 are numbered similarly.

Bladder 1698 is similar to bladder 598 except that bladder 698 additionally includes baffles or divider walls 1601, 1602 which partition, divide or compartmentalize bladder 1698 into compartments 1603-1, 1603-2 and 1603-3 (collectively referred to as compartment 1603). Compartment 1603-2 contains transducer 276. In some implementations, walls 1601, 1602 may be formed from a flexible or collapsible polymeric imperforate panel which is sealed to the outer wall or walls of bladder 598 to fluidly isolate the different compartments 1603 from one another.

Multidirectional valve 1609-1 comprises a valve fluidly coupled to the outlet side of pump 604 and to each of the individual compartment 1603 so as to selectively and controllably channel or direct fluid from pump 604 into the different compartments 1603 so as to control a degree to which each of the individual compartments 1603 are inflated with the fluid coupling medium 599. Multidirectional valve 1609-2 comprises a valve fluidly coupled to the inlet side of pump 604 and to each of the individual compartments 1603 to selectively or controllably channel or direct fluid from such compartments back to pump 604. Both of valves 1609-1 and 1609-2 may be under the control of probe controller 610.

As further shown by FIG. 27A, 524 omits adhesive layer 581, wherein an adhesive layer 1681 is pre-applied to surface 34 of the organ prior to the positioning of probe 1624 against the organ surface 34. In some implementations, adhesive layer 1681 may be coated or sprayed upon surface 34. In some implementations, the adhesive composition of adhesive layer 1681 may comprise an organ adhesive, such as a fibrin sealant or material such as Tisseel commercially available from Baxter Healthcare. Once the lower surface of bladder 6098 has been lowered and such or inflated into contact with adhesive layer 1681, adhesive layer 1681 adhesively secures bladder 1681 against surface 34.

FIG. 27B illustrates probe 1624 with the compartments 1603 of bladder 1698 differently inflated to re-orient or tilt head 572 at an oblique angle relative to surface 34, altering the orientation or angle of transducer 276 relative to surface 34 so as to alter the field-of-view of transducer 276. In the example illustrated, probe controller 610 has output control signals causing valves 1609-1 and 1609-2 to control the flow of the fluid coupling medium 599 into and out of the individual compartments 1603 such that compartment 1603-1 has the largest amount of pressure and/or is inflated to a larger size relative to compartment 1603-2. Likewise, compartment 1603-2 has a larger amount of pressure and/or is inflated to a larger size relative to compartment 1603-3. This results in head 572 being tilted or angled relative to surface 34 while the lower exterior surface of bladder 1698 is adhesively secured to surface 34 by adhesive layer 1681, shifting the field-of-view of transducer 276 to the left as seen in FIG. 27B.

Although bladder 1698 is illustrated as having three compartments 1603 along a single axis (left to right in FIG. 27A), in other implementations, bladder 1698 may include a greater or fewer of such compartments arranged along the same or different axes, wherein each of such compartments may be selectively inflatable to control the orientation of head 572 and the field-of-view of transducer 276. In some implementations, those compartments that do not contain transducer 276 may contain and may be in selectively inflated or deflated with fluids other than acoustic coupling medium 599. Although valves 1609-1, 1609-2 are illustrated as being provided on head 572, in other implementations, valves 1609-1, 1609-2 may alternatively located as part of the external probe control system 586. Although single multidirectional valves are illustrated for controlling the inflation of multiple compartments, each of such compartments 6203 may be provided with a dedicated valve or valves for controlling the extent of inflation of the particular compartment.

Figure 28A:
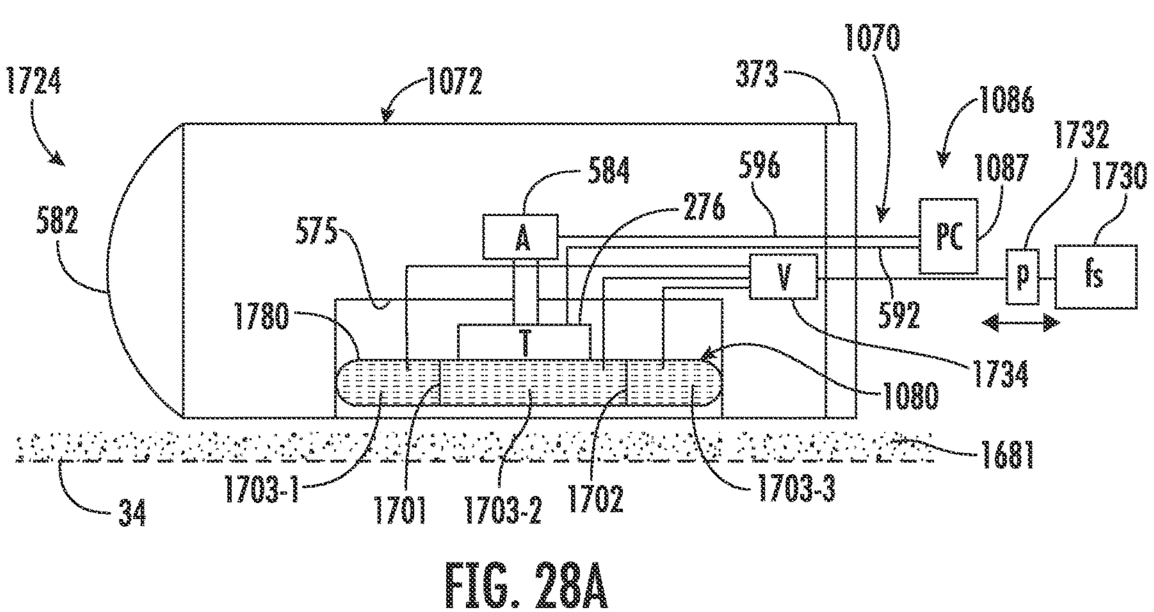
FIG. 28A is a sectional view of portions of an example organ surface ultrasound probe having a compartmentalized bladder in a first inflation state.
Figure 28B:
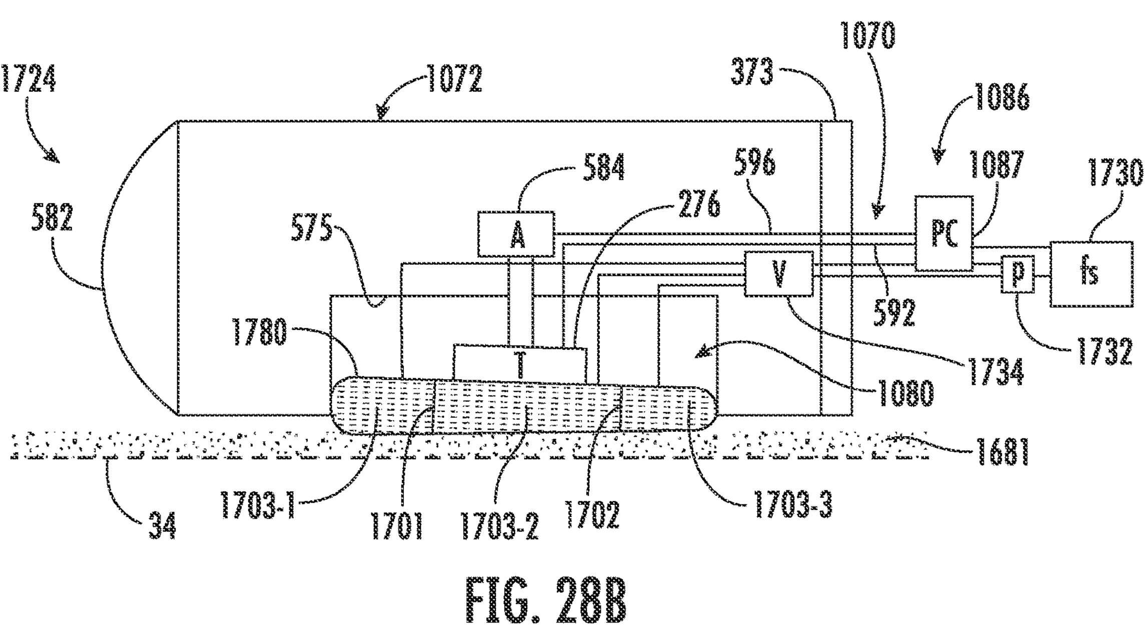
FIG. 28B is a sectional view of the organ surface ultrasound probe of FIG. 28B with the compartmentalize bladder in a second inflation state.

FIGS. 28A and 28B are diagrams schematically illustrating portions of an example organ surface ultrasound probe 1724. FIGS. 28A and 28B illustrate an example of how a compartmentalized bladder may be selectively inflated to control the orientation and field-of-view of a transducer relative to the probe head supporting the transducer. Probe 1724 is similar to probe 1024 described above except that probe 1724 comprises bladder 1780 and acoustic coupling medium 599 in place of acoustic coupler 1080 and additionally comprises fluid source 1730, bidirectional pump 1732 and multidirectional valve 1734. The remaining components of probe 1724 which correspond to components of probe 1024 are numbered similarly.

Bladder 1780 supports transducer 276 and is similar to bladder 598 except that bladder 1780 comprises internal baffles or walls 1701, 1702 which divide and compartmentalize the interior of bladder 1780 into compartments 1703-1, 1703-2 and 1703-3 (collectively referred to as compartments 1703). Walls 1701, 1702 fluidly isolate such compartments 1703 from one another.

Fluid source 1730 comprises a reservoir or container of fluid that serves as an acoustic coupling agent. Pump 1732 comprises a bidirectional pump configured to drive fluid from fluid source 1730 in either direction between fluid source 1730 and valve 1734. Pump 1732 is under the operational control of probe controller 1087. In some implementations, probe controller 1087 may further control fluid source 1730.

Valve 1734 comprise a multidirectional valve configured to selectively direct flow of the fluid from fluid source 1730 between pump 1732 and each of the individual compartments 1703. Valve 1734 is under the control of probe controller 1087. Valve controls the flow of fluid (acoustic coupling medium) between fluid source 1730 in each of the compartments 1703 to control and adjust the inflation level of each of compartments 1703 of bladder 1780.

FIG. 28B illustrates an example where probe controller 1087 has output control signals causing pump 1732 to move fluid from fluid source 1730 to valve 1734 and has further output control signals to valve 1734 such that compartment 1703-1 has the largest amount of pressure and/or is inflated to a larger size relative to compartment 1703-2. Likewise, compartment 1703-2 has a larger amount of pressure and/or is inflated to a larger size relative to compartment 1703-3. This results in transducer 276 being tilted or angled relative to head 1072 and surface 34 while the lower exterior surface of bladder 1780 is adhesively secured to surface 34 by adhesive layer 1681, shifting the field-of-view of transducer 276 to the left as seen in FIG. 28B.

Although bladder 1780 is illustrated as having three compartments 1703 along a single axis (left to right in FIG. 28A), in other implementations, bladder 1798 may include a greater or fewer of such compartments arranged along the same axis or multiple different axes (for example, multiple different horizontal axes intersecting a vertical axis), wherein each of such compartments may be selectively inflatable to control the orientation of transducer 276 and the field-of-view of transducer 276. In some implementations, those compartments not underlying transducer 276 may contain and may be selectively inflated or deflated with fluids other than acoustic coupling medium 599. Although valve 1734 is illustrated as being provided on head 1072, in other implementations, valves valve 1734 may alternatively located as part of the external probe control system. Although single multidirectional valves are illustrated for controlling the inflation of multiple compartments, each of such compartments 1703 may alternatively be provided with a dedicated valve or valves for controlling the extent of inflation of the particular compartment.

In the example illustrated, adhesive layer 1681 (described above) is applied prior to the positioning incest or inflation of bladder 1780 into contact with adhesive layer 1681. In some implementations, adhesive layer 1681 may be coated, sprayed or otherwise applied to organ surface 34, wherein adhesive layer 1681 adheres the inflated bladder 1780 to organ surface 34. In other implementations, the adhesive layer 1681 may alternatively be applied directly to the lower surface of bladder 1780.

In the example illustrated in FIGS. 28A and 28B, the compartmentalized bladder 1780 and valve 1734 are illustrated as being incorporated into and as part of organ surface ultrasound probe 1724, where probe 1724 is adhered to the organ surface by adhesive layer 1681. In other implementations, valve 1734 may be provided as part of the external probe control system. In some implementations, probe 1724 may be adhered or otherwise secured to a compliant layer that is secured to the organ surface 34, such as any of the above-described compliant layers, such as compliant layer 980.

Figures 29, 30:
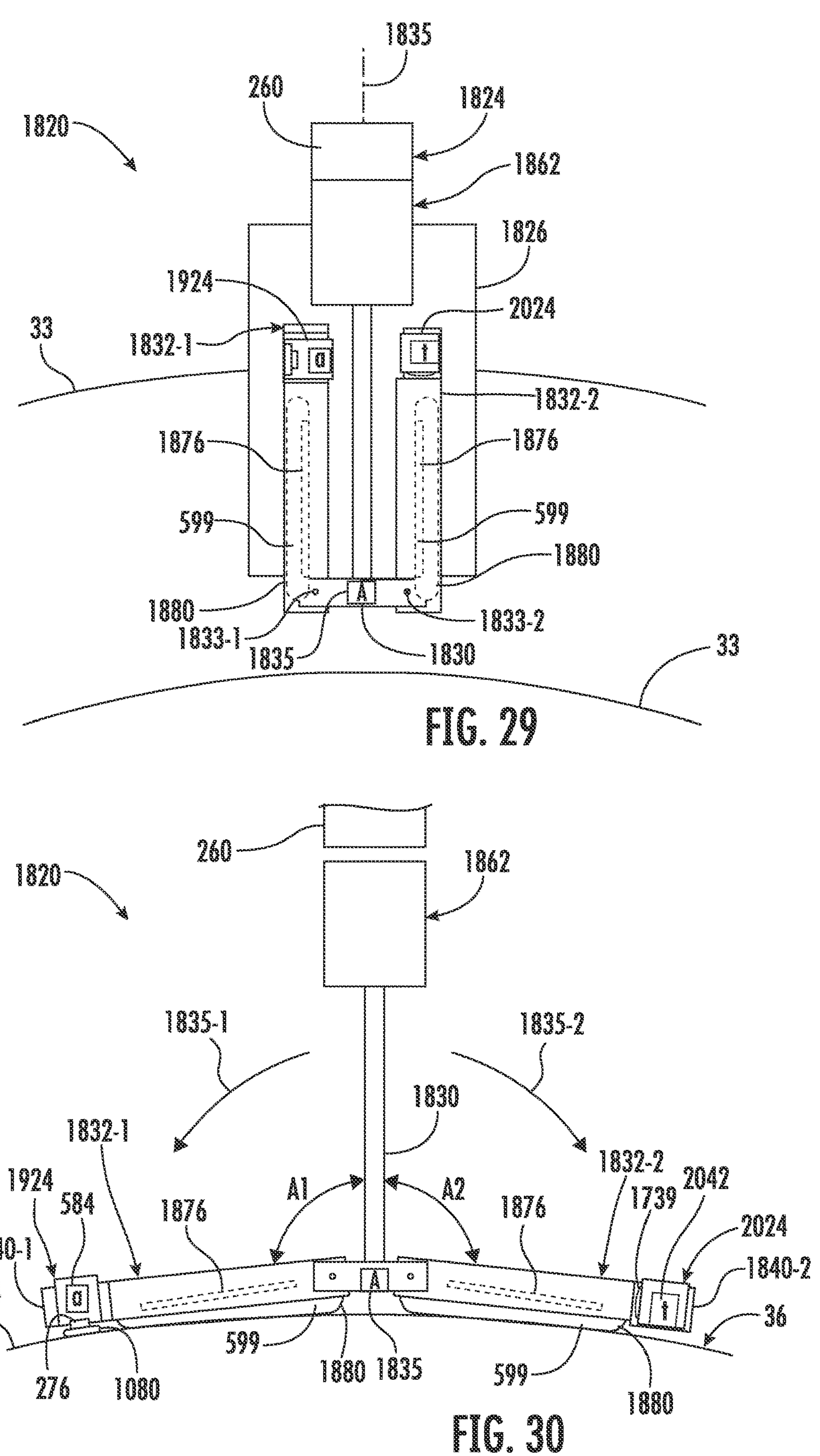
FIG. 29 is a diagram illustrating portions of an example ultrasound sensing system with an example sensing head having wings in a retracted state while being inserted through a trocar.
FIG. 30 is a diagram illustrating the example ultrasound sensing system of FIG. 29 with the wings of the example sensing head in an extended state and in contact with a surface of an organ.

FIGS. 29-30 are diagrams schematically illustrating deployment of an example ultrasound sensing system 1820. FIGS. 29-30 illustrate an example of how an ultrasound sensing system may utilize an organ surface ultrasound probe having a pair of retractable wings supporting ultrasound transducers, wherein the wings are retracted during movements through a trocar and are unfurled or extended onto the organ surface. FIGS. 29-30 further illustrate an example of how an organ surface ultrasound probe may comprise docking stations for supporting the additional satellite ultrasound probes, whether they be organ surface ultrasound probes or intra-organ (interstitial) ultrasound probes. System 1820 comprises organ surface ultrasound probe 1824, trocar 1826, organ surface ultrasound probe 1924, intra-organ ultrasound probe 2024, processing instructions 91, surgical automation 94 and display unit 96.

FIG. 29 illustrates portions of organ surface ultrasound probe 1824 being moved through trocar 1826. Trocar 1826 is similar to trocar 126 described above and comprises a tube. Organ surface ultrasound probe 1824 comprises insertion shaft 260 (described above) and sensing head 1862. Insertion shaft 260 is configured to pass through trocar 1826 through the skin 33 of a patient to allow probe 1824 to be moved towards an internal organ of the patient. As discussed above, insertion shaft 260 may include a bundle 170 of fluid and/or electrical lines.

Sensing head 1862 comprises central support 1830 and wings 1832-1, 1832-2 (collectively referred to as wings 1832). Central support 1830 is releasably connected to insertion shaft 260 and includes internal conduits for routing electrical and/or fluid lines or conduits to each of wings 1832. In some implementations, central support 1830 may additionally how various controllers, sensors, valves and/or pumps for locally controlling wings 1830 and/or supplying electrical power, dating control signals and/or inflation fluid/acoustic coupling fluid to each of wings 1830 as described above. In other implementations, at least some of such valves, pumps, sensors or controllers may be located remotely, such as part of an external probe control system 586 which is connected to the wings 1830.

As shown in FIG. 30, once sensing head 1862 has been positioned against surface 34 of an internal organ, insertion shaft 260 may be disconnected and separated from head 1862. In such implementations, the electrical and or/or fluid lines forming bundle 170 may remain connected to head 1862 and a fashion similar to that described above with respect to FIG. 7. In some implementations head 1862 may include local power in the form of a battery and may be under the control of a remote controller which communicates with head 1862 in a wireless fashion.

Wings 1832 each carry and support an ultrasound transducer 1876 and a bladder 1880 containing an acoustic coupling medium 599 (described above). Each of wings

1832 is pivotally supported or coupled to central support 1830 for pivotal movement between a retracted position as shown in FIG. 29 and one of multiple possible, user selectable extended positions as shown in FIG. 30. Wing 1832-1 pivots about pivot axis 1833-1 to the retracted position shown in FIG. 29 in which the length or longitudinal axis of wing 1832-1 extends non-perpendicular to the longitudinal axis of central support 1830. Similarly, wing 1832-2 pivots about axis 1833-2 to the retracted position shown in FIGS. 29 and 31A in which the length or longitudinal axis of wing 1832-2 extends non-perpendicular to the longitudinal axis of central support 1830. In the example illustrated, when in the retracted positions, wings 1832 each extend substantially parallel to the longitudinal axis 1834 of central support 1830. In some implementations, when in the retracted positions, the backside of wings 1832 may extend at an acute angle relative to the central support 1830.

As shown by FIGS. 30 and 31B, once head 1862 has passed through trocar 1826, wings 1832 may be unfurled or extended to an expanse much wider than the internal diameter with of trocar 1826. During such unfurling, an actuator 18351835 may be used to pivot wings 1832-1, 1832-2 about the respective axes 1833-1, 1833-2 in the directions 1835-1 and 1835-2. In some implementations, actuator 18351835 comprise an electric power device configured to controllably pivot wings 1832 about the respective axes. In some implementations, actuator 1835 (schematically illustrated) may be in the form of an electromagnet positioned along support shaft 1830 and springs, such as a torsion springs for biasing wings 1832 about their respective axes 1833 towards the extended positions, wherein actuation the electromagnet draws or moves wings 1832 against such bias to the retracted positions. In some implementations, wings 1832 may be moved between the retracted and extended positions using a robotic arm, such as the example robotic arm 2037 schematically shown in FIG. 34 or an effector or cutting tool 2040 (shown in FIG. 34). In such implementations, central support 1830 may additionally comprise temporary claws or grips which temporarily retain wings 1832 in the retracted position or alternatively, in the extended position, wherein such wings 1832 are released from such grips in response to a sufficient pivoting force from the robotic arm. In yet other implementations, wings 1832 may be selectively pivoted using other mechanisms.

As further shown by FIG. 30, wings 1832, when extended, extend at angles A1 and A2 relative to central support 1830. In some implementations, angles A1 and A2 are each at least 90°. In some implementations, angles A1 and A2 are greater than 90°, forming an obtuse angle with respect to the longitudinal axis 1834 of central support 1830. In some implementations, angles A1 and A2 may be different from one another. For example, the different wings 1832 may be deployed to different angles A1 and A2 so as to better conform to surface 34. As discussed above, doing retraction, wings 1832 are attracted such angles A1 and A2 are each less than 90° in some implementations, 0° (parallel to axis 1834).

In the example illustrated, each of wings 1832 may have a construction similar to that of sensing head 572 described above. For reasons of illustration, portions of wings 1832 are omitted, wherein such omitted portions may be described above with respect to the other described sensing heads. For example, each of wings 1832 may additionally comprise actuator 584, pressure sensor 587, temperature sensor 588 and an adhesive layer 581 formed on bladder 1880. Bladder 1880 and transducer 1876 may be similar to transducer 276 and bladder 580 described above, wherein transducer 1876 is pivotable, rotatable or otherwise movable within the acoustic coupling medium 599 contained within the bladder 1880. In such implementations, each of wings 1832 may be connected to corresponding components of an external probe control system similar to external probe control system 586 described above. For example, the acoustic coupling medium may be circulated through each of bladders 1880 to cool transducers 1876. In some implementations, each of wings 1832 may alternatively be temporally secured to a conformable or compliant panel, similar to panel 980, so as to be joined to surface 34 fashion similar to that described above with respect to FIGS. 13-14. In yet other implementations, each wings 1832 may have a construction similar to that of head 1072, head 1272 or head 1572 described above.

As further shown by FIGS. 29 and 30, wings 1832 may additionally comprise docking stations for temporarily supporting additional satellite ultrasound probes. In the example illustrated, wings 1832-1 and 1832-2 comprise docking stations 1840-1 and 1840-2, respectively (collectively referred to as docking stations 1840). Docking stations 1840 each comprise a structure configured to support, grip or releasably contain portions of an additional ultrasound probe. For example, docking station 1840-1 may extend about sides of an additional ultrasound probe. In some implementations, docking station 1840-1 may comprise a pair of actuatable or resiliently biased claws 1843 to grasp about sides of an additional ultrasound probe. Docking station 1840-2 may comprise a cup or box into which the additional ultrasound probe may be received. In such implementations, the docking station may be configured to facilitate use of the additional ultrasound probe while the additional ultrasound probe is secured by the docking station. For example, each of such docking stations 1840 may include a lower window, a lower bladder of acoustic coupling medium or other structure that facilitates acoustic coupling of the additional satellite ultrasound probe with surface 34 while the additional probe is docked.

In the example illustrated, docking station 1840-1 is illustrated as releasably or removably supporting or containing an additional ultrasound probe 1924. Ultrasound probe 1924 is illustrated as having a construction similar to that of probe 1024 described above. Probe 1924 may have features, projections, detents or the like, that facilitate repeatable release and attach of probe 1924 by a gripping device, such as the gripping device of a robotic surgical arm. Probe 1924 comprises transducer 276, bladder 1880 and actuator 584, each of which is described above. Docking station 1840-1 has a lower opening or window through which transducer 276 and bladder 180 may project into acoustic contact with surface 34 while probe 1924 is retained by docking station 1840-1. As a result, system 1820 may concurrently acquire ultrasound image data from each of transducers 186 of wings 1832 and transducer 276 of probe 1924.

In the example illustrated, docking station 1840-2 is illustrated as releasably or removably supporting or containing an additional ultrasound probe 2024. Ultrasound probe 2024 may be configured as an intra-organ or interstitial ultrasound probe. For example, probe 2024 may have a construction or configuration similar to that of probes 1728, 1828, 1928, 2028, 2128, 2228, 2328, 2428 or head 2530 described above. Probe 2024 may have features, projections, detents or the like, that facilitate repeatable release and attach of probe 1924 by a gripping device, such as the gripping device of a robotic surgical arm. Ultrasound probe 2024 comprises a transducer 2042. In the example illustrated, probe 2024 comprises a rounded and blunt tip 1739 (described above). In other implementations, probe 2424 may comprise a tip 2038 (described above). In other implementations, docking station 1840-2 may retain another organ surface ultrasound probes.

Although head 1862 is illustrated as having a pair of opposite wings 1832 (angularly spaced 180 agrees from one another about axis 1834), in other implementations, head 1862 may comprise a multitude of different pivotable wings extending about central support 1830. For example, as shown by FIGS. 32A and 32B, head 1862 may include three pivotable wings 1832-1, 1832-2 and 1832-3, each wing being angularly spaced from each of the two other wings by 120° about axis 1834. FIG. 32A illustrates the three wings in the retracted position while FIG. 32B illustrates the wings 1832 extended. Wing 1832-3 is similar to wing 1832-1. In such implementations, wings 1832 also pivots between one or more extended positions and one or more retracted positions similar to that shown in FIGS. 29 and 30.

Figures 33A, 33B:
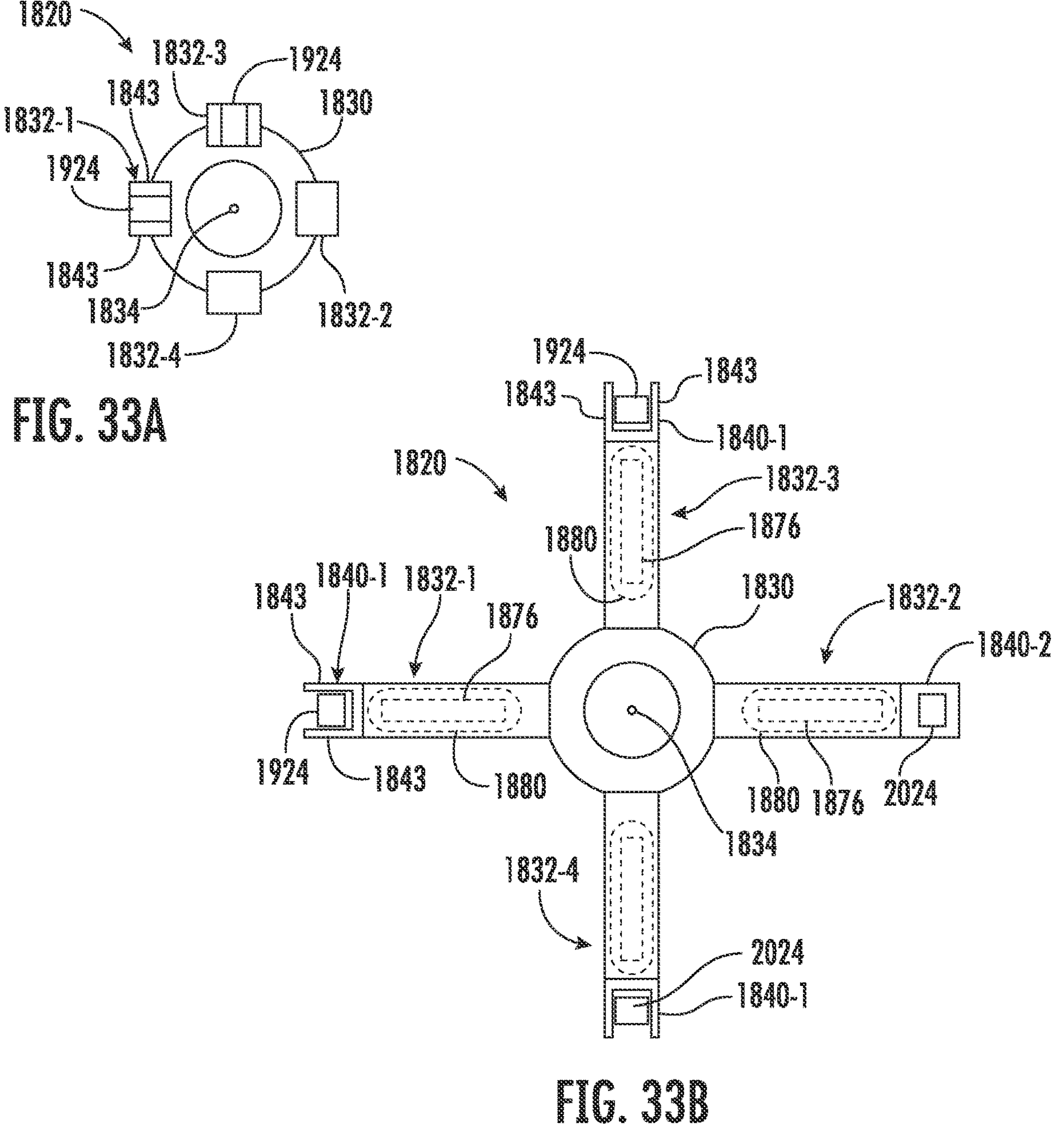
FIG. 33A is a top view illustrating portions of an example ultrasound sensing system with an example sensing head having wings in a retracted state.
FIG. 33B is a top view illustrating portions of the example ultrasound sensing system of FIG. 33A with the wings and an extended state.

As shown by FIGS. 33A and 33B, head 1862 may include four pivotable wings 1832-1, 1832-2, 1832-3 and 1832-4, each wing being angularly spaced from adjacent wings by 90° about axis 1834. FIG. 33A illustrates the four wings in the retracted position while FIG. 33B illustrates the wings 1832 extended. Wing 1832-4 is similar to wing 1832-2. In other implementations, each of heads 1862 may have various other combinations of wings similar to wing 1832-1 or wing 1832-2. In some implementations, the different wings of the sensing head 1862 may be of one type of wing, the type of wing 1832-1 or the type of wing 1832-2. In such implementations, wings 1832 also pivot between extended position and retracted positions similar to that shown in FIGS. 29 and 30.

Figure 34:
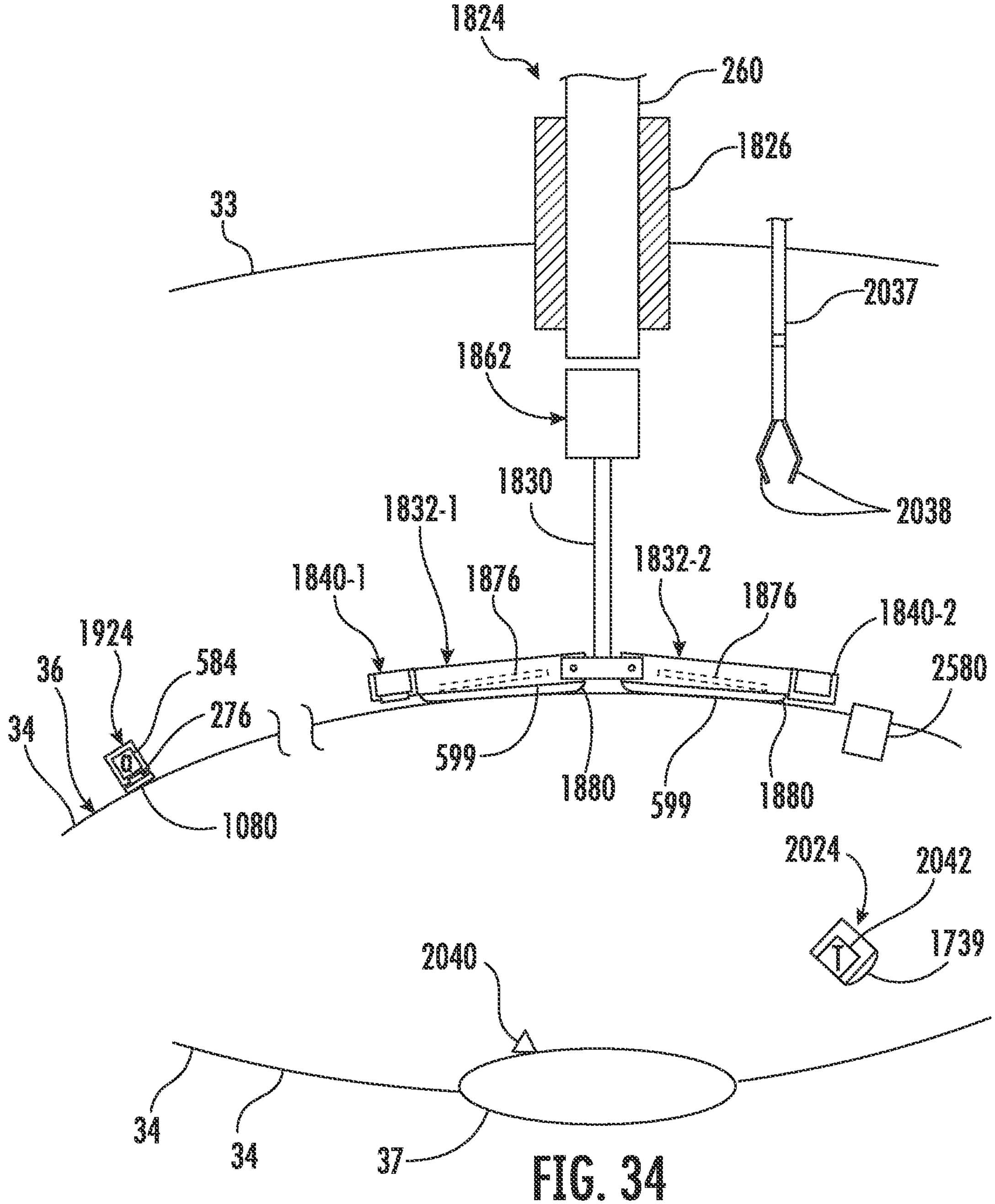
FIG. 34 is a diagram schematically illustrating portions of the example ultrasound sensing system of FIG. 30 with satellite ultrasound probes being removed from docking stations and deployed.

As shown by FIG. 34, prior to or following positioning of wings 1832 adjacent to and along surface 34 of the organ, probe 1924 and/or 2024 may be deployed. In the example shown in FIG. 31, an articulated an extendable robotic arm 2037 having a pair of grippers 2038 may be used to assist in removing the probes 1924, 2024 from their respective docking stations 1840-1, 1840-2. In the example illustrated, robotic arm 2037 has removed probe 1924 from docking station 1840-1 and position probe 1924 at a location spaced from sensing head 1862 so as to image the example tumor 37 along the opposite organ surface 34. In the example illustrated, probe 1924 may further image an inserted cutting tool 2040 being used to excise or remove tumor 37. In some implementations, probe 1924 may be positioned so as to have a field-of-view containing regions just forward of the effector or cutting tool 2040, regions along the expected path of cutting tool 2040. As discussed above, probe 1924 may communicate to an external probe controller in a wired or wireless fashion.

As further shown by FIG. 34, in the example illustrated, robotic arm 2037 has removed probe 2024 from its docking station 1840-2 and has moved probe 2024 through trocar 2580 into the interior of the example organ 36. Probe 2024 may be positioned such that the field-of-view of transducer 2042 contains portions of tumor 37 and/or the effector 2040. In some implementations, probe 2024 may be positioned so as to have a field-of-view containing regions just forward of the effector or cutting tool 2040, regions along the expected path of cutting tool 2040. As with probe 1924, probe 2024 may communicate in a wired or wireless fashion with an external probe controller and processing unit 90.

In the example illustrated, processing unit 90 may receive ultrasound image data from each of probes 1824, 1924 and 2024. Processing unit 90 may receive ultrasound image data from both of transducers 1876 which may or may not be at the same angle. The various ultrasound image data may include tumor 37, portions of tumor 37 or effector 2040. The image data may be taken at different angles. As discussed above, processing unit 90, following instructions contained in a non-transitory computer-readable medium 91, superimposes and/or registers the first ultrasound data obtained from ultrasound probe 1824, second ultrasound data obtained from ultrasound probe 1924 and third ultrasound data received from probe 2024. For example, ultrasound data values from each of the transducers 276, 1876 and 2042 may be assigned or aligned to the same physical location, a registration of coordinates. As discussed above with respect to FIG. 3C, the registered sets of data may be transmitted to a controller 94 to assist with automation or robotic surgery. The superimposed and/or registered ultrasound data may additionally or alternatively be communicated to a display unit 96 which uses the registered ultrasound data to generate and display superimposed and registered ultrasound images for viewing by a medical practitioner or other person.

In some implementations, the different transducers 276, 1876 and 2042 may operate in different modes depending upon where the ultrasound energy is being focused. For example, in circumstances where the ultrasound probe is focusing its energy on portions of tumor 37 which is to be surgically removed, a controller may increase the intensity of the ultrasound energy to a level above or exceeding existing Food and Drug Administration (FDA) guidelines for exposure levels for healthy tissue. Because the tissue 84 receiving the otherwise excessive ultrasound output exposure levels is designated for removal, any risk of damage to such tissue caused by excessive acoustic output exposure levels is not relevant and disregarded. Because the ultrasound probe is operated at a higher intensity in the focused upon area of the organ, which is to be removed, the penetration of the ultrasound waves into the tissue may be deeper and the images generated or derived from such ultrasound waves may have a greater resolution.

Figure 35:
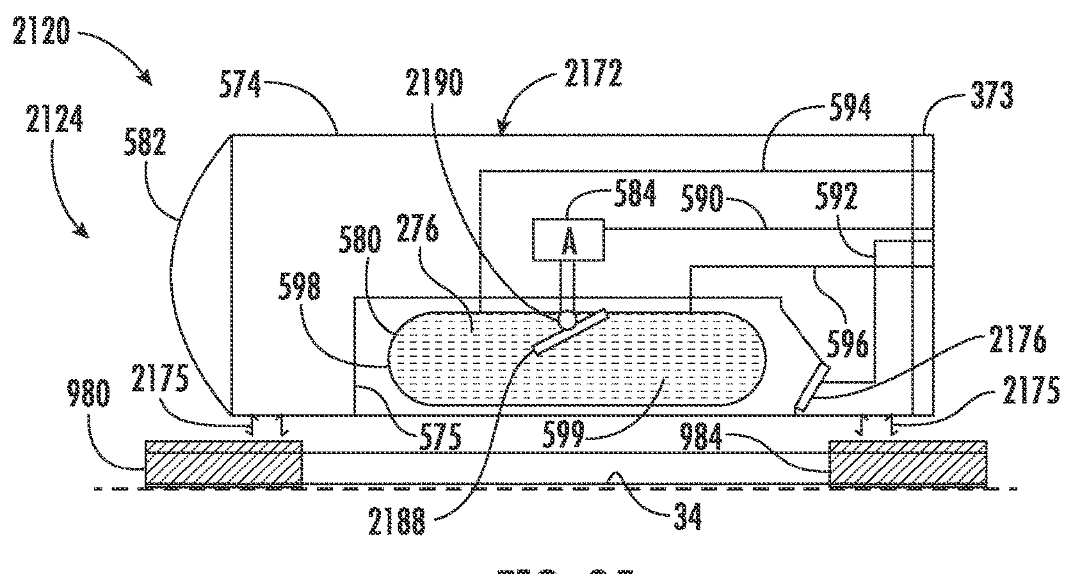
FIG. 35 is a sectional view schematically illustrating portions of an example organ surface ultrasound having a bladder in a first inflation state.
Figure 36A:
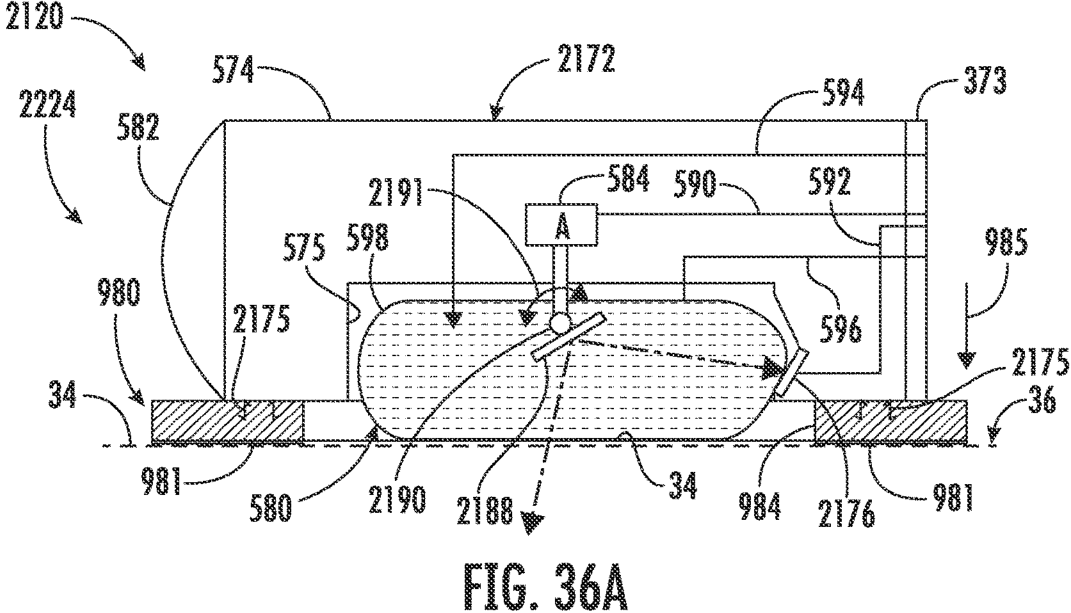
FIG. 36A of the example organ surface ultrasound probe of FIG. 35 with the bladder in a second inflation state.

FIGS. 35 and 36A schematically illustrates portions of an example ultrasound sensing system 2120. FIGS. 35 and 36A illustrated example of how an ultrasound transducer and an acoustic mirror may be used to control and expand a field of view of the ultrasound transducer in a sensing head. FIGS. 35 and 36A further provide an example of how a sensing head of an ultrasound probe may be secured to a compliant member which is itself secured to the surface of an organ. System 2120 comprises external probe control system 586 (described above) and sensing head 2172. Sensing head 2172 is similar to except that sensing head 2172 comprises ultrasound transducer 2176, acoustic mirror 2188 and a gimbal 2190 in place of transducer 276. System 2120 further comprises couplers 2175 in place of couplers 975. Those remaining components of system 2120 which correspond to components of system 820 are numbered signal and/or are shown and described above with respect to FIGS. 12-13 above.

Ultrasound transducer 2176 is similar to ultrasound transducer 276 described above except that ultrasound transducer 2176 is supported or mounted within chamber 575 of head 217, and external to bladder 580, at an orientation so as to direct ultrasound waves towards acoustic mirror 2188. Acoustic mirror 2188 comprises an acoustic mirror movably supported by a gimbal 2190 and movable by actuator 584. Although sensing head 2172 is illustrated as being mountable to conformable panel 980, in other implementations, sensing head 2090 may be directly secured to surface 34 of the underlying organ 36. As discussed above, housing 574 and/or bladder 580 may directly adhered to surface 34 by an adhesive, by barbs, or by other attachment mechanisms described above.

As shown in FIG. 36A, bladder 580 may be inflated such that surface of bladder 580 moves into contact with surface 34 of organ 36. Surfaces of bladder 580 may additionally move into contact with transducer 2176 for acoustic coupling with transducer 2176. Following the connection, directly or indirectly, to surface 34, and the positioning of bladder 580 into contact with surface 34, transducer 2176 may emit ultrasound mechanical waves at an angle which are directed off of acoustic mirror 2188 and reflected towards organ surface 34. Probe controller 610 (shown and described above) may output control signals causing actuator 584 to pivot acoustic mirror 2188 about multiple different axes (similar to a ball joint) (as indicated by arrows 2191) so as to control and vary the location of the field-of-view of the ultrasound waves being output by transducer 2176.

Transducer 2176 and acoustic mirror 2188 increases the propagation distance of the ultrasound waves, increasing or widening the field-of-view of sensing head 2172. In some implementations, probe controller 610 may output control signals causing actuator 584 to continuously rock acoustic mirror 2188 about one or more axes to further widen the field-of-view or imaging provided by transducer 2176 and sensing head 2172. In some implementations, transducer 2176 may also be pivotally supported and may be pivoted by an associated actuator for further precise control over the location of the field-of-view of sensing head 2172.

Although acoustic mirror 2188 and its associated gimbal 2190 are illustrated as being contained within bladder 598, surrounded by acoustic coupling medium 599, in other implementations, acoustic mirror 2188 and its associated gimbal 2190 may be supported external to bladder 598, but in contact with or acoustically coupled to the exterior of bladder 598. Regardless of whether acoustic mirror 2188 is internal or external to bladder 598, acoustic mirror may be positioned so as to receive and reflect the mechanical waves from transducer 2176 towards the organ 36.

Couplers 2175 secure housing 574 of sensing head 2172 to compliant panel 980. Couplers 2175 comprise barbs or barbed fasteners projecting from a lower surface of housing 574 and sensing head 2172. Couplers 2175 penetrate compliant panel 980 and have hooks/barbs that inhibit inadvertent withdrawal of couplers 2175 from compliant panel 980.

Figure 36B:
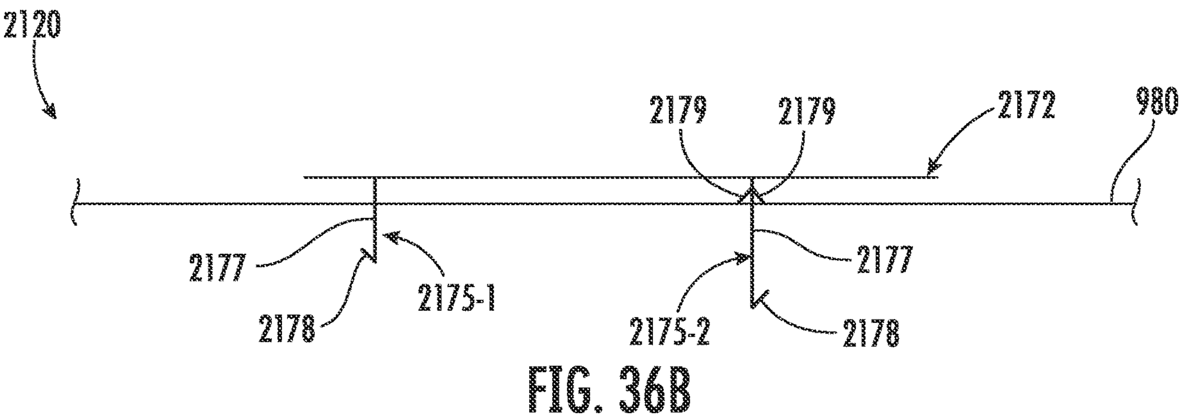
FIG. 36B is an enlarged fragmentary sectional view of the example organ surface ultrasound probe of FIG. 36A illustrating coupling of a sensing head to a compliant panel secured to an organ surface.

FIG. 36B is an enlarged view illustrating portions of sensing head 2172 secured to compliant panel 980. FIG. 36B illustrates two example couplers 2175-1 and 2175-2 (collectively referred to as couplers 2175). Each of couplers 2175 comprises a post 2177 and a hook 2178. Coupler 2175-2 is longer than coupler 2175 and additionally comprises lateral struts 2179. Hook 2178 obliquely projects from post 2177 and upward angle towards sensing head 2172 and is configured to resist withdrawal of post 2177 from compliant panel 980 once coupler 2175 has been inserted into compliant panel 980. Lateral struts 2179 obliquely project from post 2177 in a downward direction towards hook 2178. Lateral struts 2179 inhibit insertion of coupler 2175-2 to control the depth at which post 2177 may be penetrated into compliant panel 980.

Figure 37A:
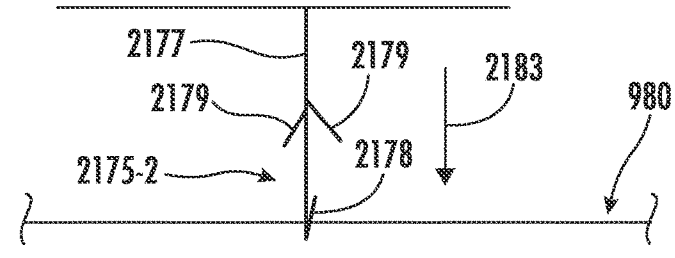
FIG. 37A is an enlarged fragmentary sectional view of a portion of the example organ surface ultrasound probe of FIG. 36B illustrating insertion of an example coupler.
Figure 37B:
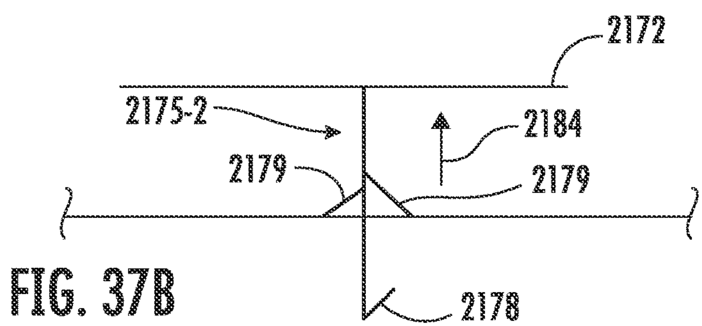
FIG. 37B is an enlarged fragmentary sectional view of the portion of the example organ surface ultrasound probe of FIG. 37A illustrating retention of the coupler to the compliant panel
Figure 37C:
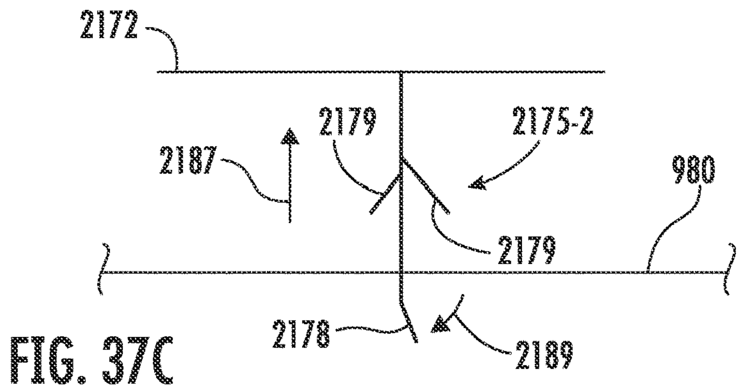
FIG. 37C is an enlarged fragmentary sectional view of the portion of the example organ surface ultrasound probe of FIG. 37B illustrating withdrawal of the coupler from the compliant panel.

FIGS. 36A, 36B and 36C illustrates insertion and subsequent withdrawal of coupler 2175-2 with respect to compliant member 980. FIG. 37A insertion and initial penetration of coupler 2175-2 into compliant panel 980. As shown by FIG. 37A, in some implementations, hook 2178 has a stiffness less than that of post 2177. During insertion of coupler 2175-2 in the direction indicated by arrow 2183, hook 2178 resiliently bends inwardly towards post 2177, facilitating insertion into compliant panel 980 and providing a reduced insertion opening (less damage to compliant member 980). Thereafter, as shown by FIG. 37B, forces exerted upon coupler 2175-2 in the direction indicated by arrow 2185 may result in hook 2178 resiliently returning to its initial angular position relative to post 2177 such that the hook 2178 more broadly engages the material of compliant panel 980 to inhibit inadvertent withdrawal of coupler 2175-2.

As shown by FIG. 36C, intended withdrawal of coupler 2175-2 and the intended withdrawal of sensing head 2172 from compliant panel 980 results in a sufficient force in the direction indicated by arrow 2187 such that hook 2178 deforms or bends towards the longitudinal axis of post 2177 in the direction indicated by arrow 2189. This results in hook 2178 being more in line with the longitudinal axis of post 2177, facilitating easier withdrawal of coupler 2175-2 in reducing any tears or surface damage to compliant member 980 as coupler 2175-2 is withdrawn. In other implementations, coupler 2175-1 or coupler 2175-2 may have other configurations.

Figure 38:
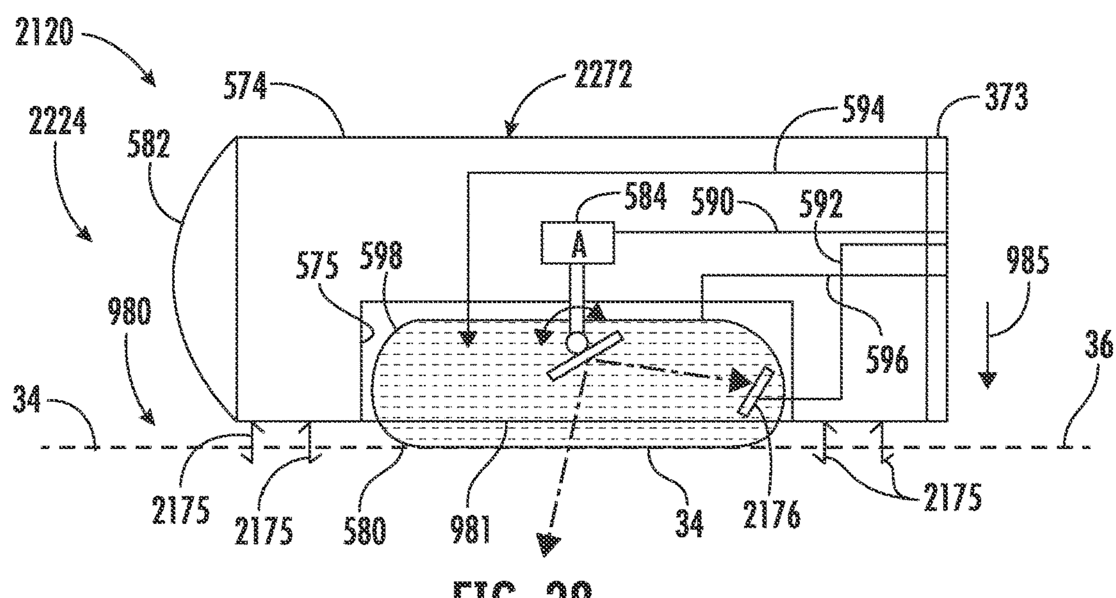
FIG. 38 is an enlarged fragmentary sectional view of an example organ surface ultrasound probe having a sensing head directly coupled to an organ surface.

FIG. 38 schematically illustrates portions of an example sensing system 2220. FIG. 38 illustrates an example of how a transducer may be provided within an inflatable bladder and may cooperate with a movable mirror to control the location of a field-of-view of the transducer. System 2220 is similar to system 2120 described above except that transducer 2176 is sealed within and mounted within bladder 580 rather than being external to bladder 580. Following the connection, directly or indirectly, to surface 34, and the positioning of bladder 580 into contact with surface 34, transducer 2176 may emit ultrasound sound waves at an angle which are directed off of acoustic mirror 2188 and reflected towards organ surface 34. Probe controller 610 (shown and described above) may output control signals causing actuator 584 to pivot acoustic mirror 2188 about multiple different axes (similar to a ball joint) (as indicated by arrows 2191) so as to control and vary the location of the field-of-view of the ultrasound waves being output by transducer 2176.

Transducer 2176 and acoustic mirror 2188 increases the propagation distance of the ultrasound waves, increasing or widening the field-of-view of sensing head 2272. In some implementations, probe controller 610 may output control signals causing actuator 584 to continuously rock acoustic mirror 2188 about one or more axes to further widen the field-of-view or imaging provided by transducer 2176 and sensing head 2272. In some implementations, transducer 2176 may also be pivotally supported and may be pivoted by an associated actuator for further precise control over the location of the field-of-view of sensing head 2272.

Similar to sensing head 2172, sensing head 2272 includes couplers 2175. In contrast to couplers 2175 of sensing head 2172, couplers 2175 of sensing head 2272 are configured (sized, shaped and formed from one or more materials) so as to penetrate surface 34 of organ 36. Couplers 2175 may have configuration similar to couplers 2175-1 and 2175-2 described above. Couplers 2175 of sensing head 2272 may interact with surface 34 of organ 36 in a fashion similar to the interaction of such couplers of sensing head 2172 with respect to compliant panel 980. In other implementations, sensing head 2172 and 2272 may alternatively be directly connected to compliant panel 980 and surface 34, respectively, by an adhesive layer. In other implementations, bladder 580 may additionally or alternatively include a lower adhesive layer for directly bonding to surface 34.

FIGS. 39-47 illustrate various examples of different intra-organ ultrasound surface probes which may serve as the intra-organ ultrasound probe 28 of system 20 described above or which may be used in other systems. Such intro-organ ultrasound probes, sometimes referred to as interstitial ultrasound probes, may be using conjunction with any of the above-described organ surface ultrasound probes or may be used independent of such organ surface ultrasound probes. Such intra-organ ultrasound probes are configured (sized and shaped) for insertion through a tube or trocar 2326.

Figure 39:
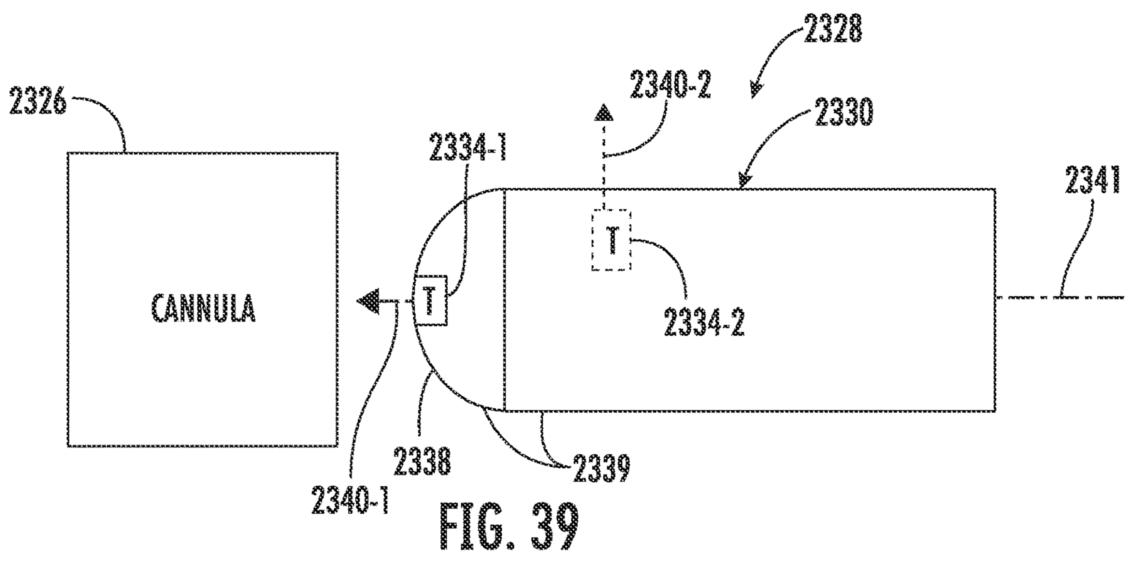
FIG. 39 is a diagram schematically illustrating portions of an example intra-organ ultrasound probe.

FIG. 39 illustrates an example portions of an example intra-organ ultrasound probe 2328. Intra-organ ultrasound probe 2328 comprises a probe head 2330 and transducers 2334-1 and 2334-2 (collectively referred to as transducers 2334).

Head 2330 comprise a body or housing for supporting transducers 2334. In the example illustrated, head 2330 terminates at a blunt tip 2338. Tip 2338 is round or smooth so as to reduce the potential for tissue laceration as head 2330 is positioned within an internal organ of a patient. In some implementations, tip 2338 is elastomeric, being formed from an elastomeric or rubber-like material to flex, bend and/or compress during contact enforceable engagement with organ tissue. In other implementations, tip 2338 may be formed from other materials or have other shapes.

In the example illustrated, at least portions of both tip 2338 and remaining exterior portions of head 2330 are coated, covered or otherwise provided with an outer hydrophobic surface 2339. Hydrophobic surface 2339 may be formed from a material such as polytetrafluoroethylene (TEFLON). Hydrophobic surface 2339 facilitates movement of head 2330 through trocar 2326. In some implementations, hydrophobic surface 2339 may be omitted. Transducers 2334 comprise ultrasound transducers.

Transducers 2334, sometimes referred to as ultrasonic sensors, each comprise a device configured to generate and sense ultrasound energy, mechanical waves. In the example illustrated, each of transducers 2334 comprises an ultrasound transceiver, a device that may convert electrical signals into ultrasound or mechanical waves and that may receive and convert reflected ultrasound or mechanical waves into electrical signals which are then transmitted to display unit 32 (shown in FIG. 1) via electrical wires or cables, or wirelessly. In some implementations, each of transducers 2334 comprises a piezoelectric (PZT) transducer that converts alternating electrical current (AC) into ultrasound using piezoelectric crystals, wherein the AC voltage oscillates such crystals to produce the ultrasonic sound or mechanical waves. In some implementations, each of transducers 2334 may comprise a capacitive transducer which generates ultrasound or mechanical waves using electrostatic fields between a conductive diaphragm and a backing plate. In some implementations, each of transducers 2334 may comprise a plurality of individual transducer elements or an array of transducer elements. In some implementations, each of transducers 2334 may comprise a conformable (conformal) transducer, a transducer having multiple transducer element supported by a flexible substrate.

Transducer 2334-1 is located proximate to tip 2338 and emits ultrasound waves in the direction generally indicated by arrow 2340-1. Images generated from or derived from signals from transducer 2334-1 may be used to steer and guide probe 2328. Although not illustrated, an acoustic coupling medium may be provided between transducer 2334-1 and the exterior surface of tip 2338.

Transducer 2334-2 is located along a side of head 2330 and emits ultrasound waves in the direction generally indicated by arrow 2340-2. Transducer 2334-2 emits waves and injection generally transverse or perpendicular to the longitudinal axis 2341 of head 2330. Because transducer 2334-2 emits ultrasound waves in a transverse direction to the longitudinal axis 2341 of head 2330, transducer 2334-2 may be easier to position for the capture of ultrasound data from a targeted region of in organ. Although not illustrated, an acoustic coupling media may be provided between transducer 2334-2 and the exterior surface of head 2330.

Figure 40:
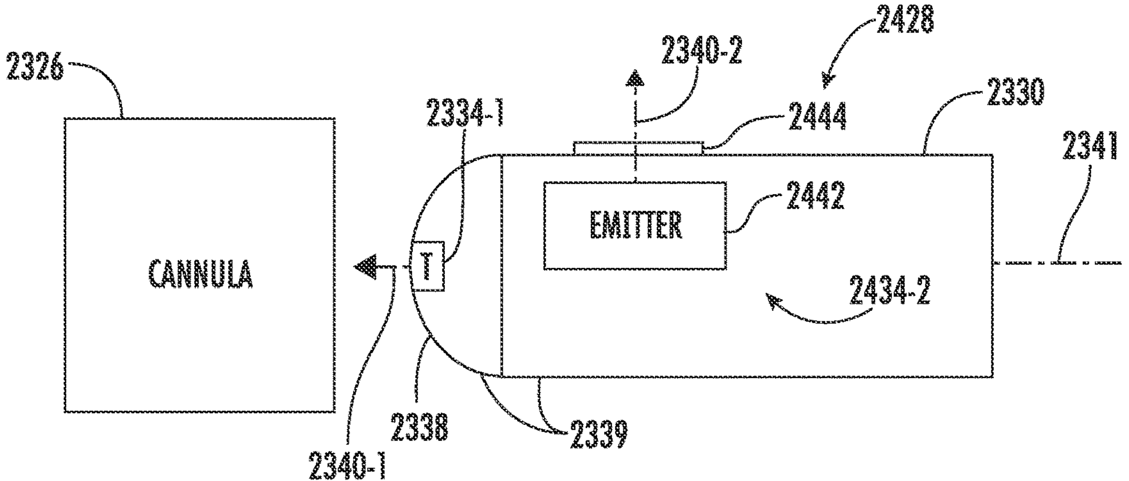
FIG. 40 is a diagram schematically illustrating portions of an example intra-organ ultrasound probe.

FIG. 40 is a diagram schematically illustrating portions of an example intra-organ ultrasound probe 2428. FIG. 40 illustrates transducer 2434-2, one example construction for transducer 2334-2. Those remaining components of probe 2428 which correspond to components of probe 2328 are numbered similarly.

Transducer 2434-2 comprises an emitter 2442 which emits ultrasound waves in the direction of arrow 2340-2. In the example illustrated, the emitted ultrasound waves are passed through a window 2444 provided along the side of head 2330. In some implementations, an acoustic coupling medium may be provided between emitter 2442 and the window 2444.

Figure 41:
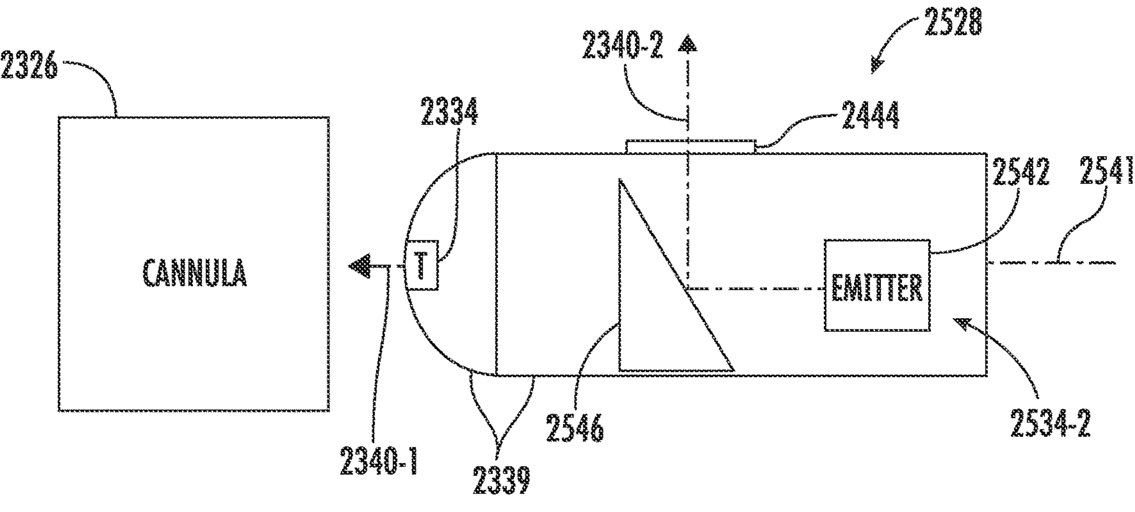
FIG. 41 is a diagram schematically illustrating portions of an example intra-organ ultrasound probe.

FIG. 41 is a diagram schematically illustrating portions of an example intra-organ ultrasound probe 2528. FIG. 40 illustrates transducer 2434-2, one example construction for transducer 2534-2. Those remaining components of probe 2528 which correspond to components of probe 2328 are numbered similarly.

Transducer 2534-2 comprises an emitter 2542 and an ultrasound deflector/acoustic mirror 2546. Emitter 2542 emits ultrasound waves in the direction parallel to axis 2341 towards tip 2338 and towards deflector 2546. Deflector 2546 comprise an angled mirror or other structure configured to deflect the ultrasound waves innate direction transverse to axis 2341, through window 2444 and in the direction indicated by arrow 2340-2. In some implementations, an acoustic coupling medium may be provided between emitter 2442 and the deflector 2546, and between the deflector 2546 and the window 2444.

Figure 42:
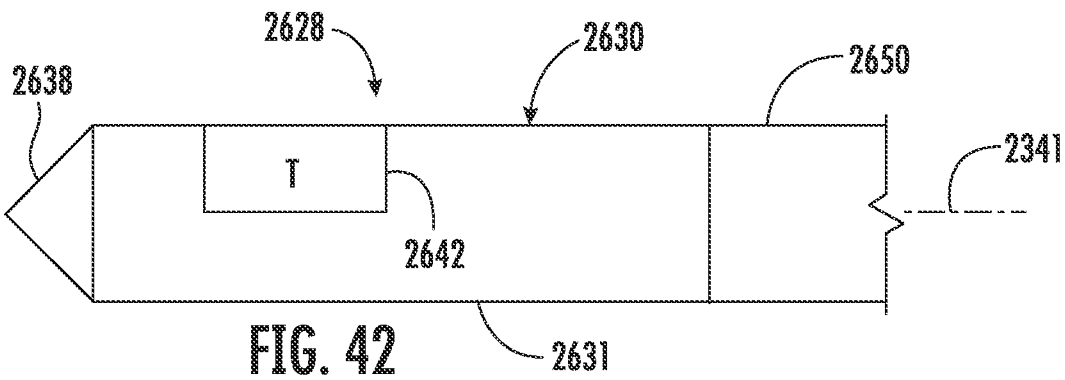
FIG. 42 is a diagram schematically illustrating portions of an example intra-organ ultrasound probe.

FIG. 42 is a diagram schematically illustrating portions of an example intra-organ ultrasound probe 2628. FIG. 42 illustrates an example of how an intra-organ ultrasound probe may be provided with a pointed tip for puncturing an organ and may be positioned by an insertion shaft. Probe 2628 comprises head 2630 and insertion shaft 2650.

Head 2630 comprise a body or housing 2031 which supports transducer 2642. Housing 2631 terminates at a pointed tip 2638 to facilitate puncturing through an organ surface.

Transducer 2642 is similar to transducer 2334-2 described above. In some implementations, transducer 2642 may have a construction similar to that described above with respect to transducer 1834-2. In some implementations, transducer 2642 may have a construction similar to that described above with respect to transducer 1934-2. Transducer 2642 emits ultrasound waves and injection generally transverse to the longitudinal axis 2341 of head 2630. Based upon reflected ultrasound waves, transducer 2642 transmits signals in a wired or wireless fashion to display unit 32 described above.

Insertion shaft 2650 extends from head 2630 and is configured to be passed through trocar 2326 (described above). Insertion shaft 2650 may be manipulated manually or by an automated robotic system for positioning head 2630. In some implementations, insertion shaft 2650 includes an internal lumen or passage through which electrical wiring or cabling extends for connection to transducer 2642.

Figure 43:
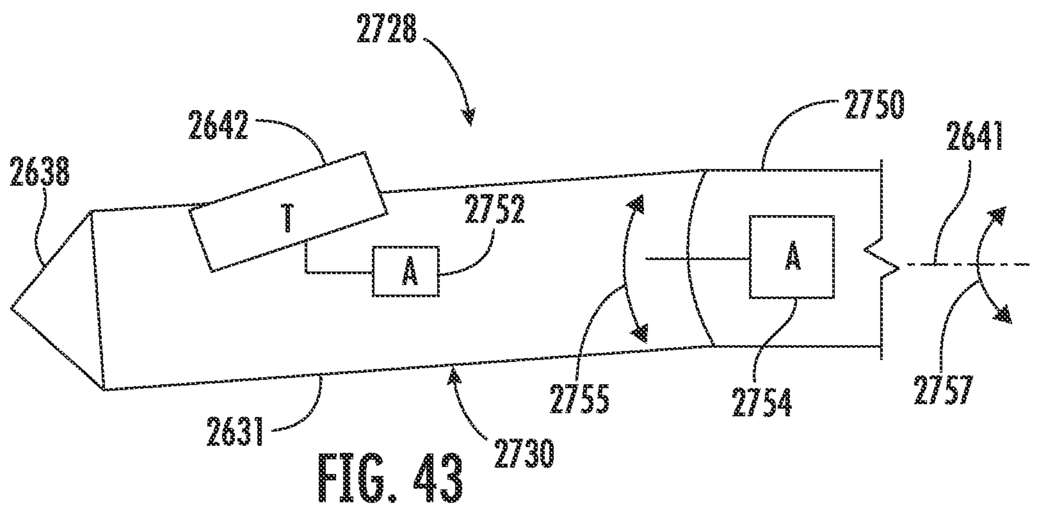
FIG. 43 is a diagram schematically illustrating portions of an example intra-organ ultrasound probe.

FIG. 43 is a diagram schematically illustrating portions of an example intra-organ ultrasound probe 2728. FIG. 43 illustrates an example of how the transducer of an intra-organ ultrasound probe may be controllably positioned relative to its supporting head and how the head itself may be controllably positioned relative to its supporting insertion shaft. Probe 2728 comprises head 2730 and insertion shaft 2750.

Head 2730 comprises body 2631 which terminates at tip 2638 as described above with respect to head 2630. Head 2730 movably supports transducer 2642 and is pivotably connected to insertion shaft 2750. As further shown by FIG. 43, head 2730 comprises an actuator 2752 operably coupled to transducer 2642 to selectively and controllably position or pivot transducer 2642. As a result, actuator 2752 may steer the field-of-view of transducer 2642. Actuator 2752 may receive control signals from a remote controller in a wired or wireless fashion. In some implementations, actuator 2752 may comprise an electric motor, an electric solenoid, a piezo resistive device, a hydraulic or pneumatic piston-cylinder assembly, or the like.

Insertion shaft 2750 is similar to insertion shaft 2650 except that insertion shaft 2750 is pivotably coupled to head 2730 to permit head 2730 to articulate or pivot relative to insertion shaft 2750 in directions about an axis that is perpendicular to the longitudinal axis 2641 of shaft 2750 (as indicated by arrows 2755). Such pivoting may be up-down and/or side-to-side. In some implementations, insertion shaft 2750 is additionally or alternatively pivotable/rotatable relative to head 2730 in directions about the axis 2641 (as indicated by arrows 2757). Such pivoting or rotation facilitates the selective positioning of transducer 2642 and its field-of-view for capturing ultrasonic image data of a tumor, effector or other region of interest. Such pivoting a rotation may further facilitate the steering of head 2730 as it is being moved through a trocar, moved through an organ surface and/or move within the organ. In the example illustrated, insertion shaft 2750 comprises an actuator 2754 for selectively and controllably positioning or pivoting head 2730 relative to insertion shaft 2750. Actuator 2754 may comprise an electric motor, electric solenoid or other forms of actuation mechanisms.

Figure 44:
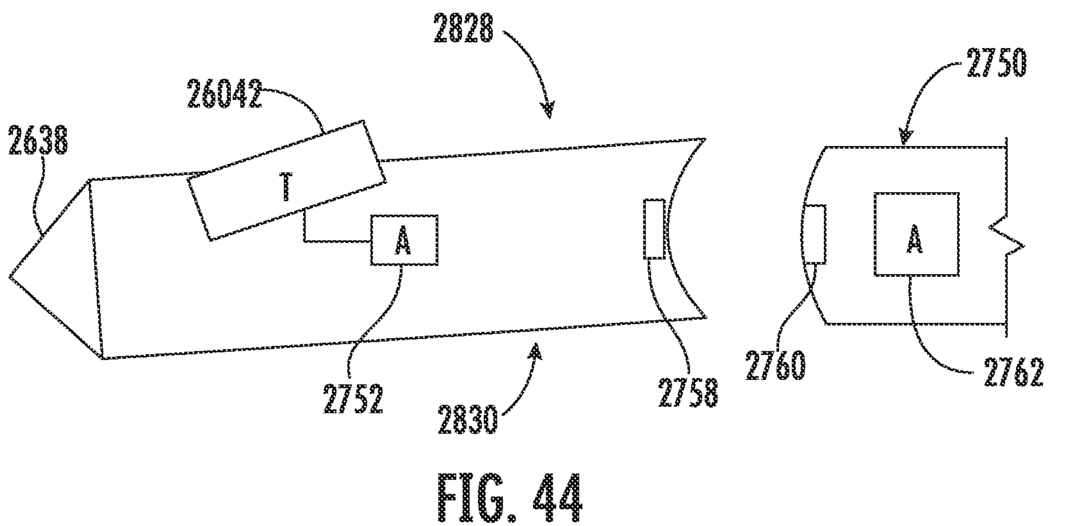
FIG. 44 is a diagram schematically illustrating portions of an example intra-organ ultrasound probe.

FIG. 44 is a diagram schematically illustrating portions of an example intra-organ ultrasound probe 2828. FIG. 44 illustrates an example of how the head of an intro-organ ultrasound probe may be disconnected both from the insertion shaft used to position the head within an organ. Probe 2828 comprises head 2830 and insertion shaft 2750.

Head 2830 is similar to head 2730 described above except that had 2830 is releasably or removably coupled to insertion shaft 2750 for separation from insertion shaft 2750 as illustrated in FIG. 44. Those remaining components of head 2830 which correspond to components of head 2730 are numbered similarly. In the example illustrated, head 2830 is magnetically coupled to insertion shaft 2750. In some implementations, one of head 2830 and insertion shaft 2750 comprises a magnet and the other of head 2830 and insertion shaft 2750 comprises either a magnet of opposite polarity or a ferrous or magnet attractable material connector or interface.

In some implementations, the magnet comprise an electromagnet capable of being turned on and turned off by an electric switch controlling the supply of current. For example, in the example illustrated, head 2830 comprises a magnet attractable connector interface 2758 while insertion shaft 2750 comprises an electromagnet 2760. Insertion shaft 2750 further comprises an actuator 2762 in the form of an electrical switch for selectively controlling the supply of electrical current to the electromagnet 2760. Electrical signals from a remote controller to actuator 2762 may be used to selectively connect insertion shaft 2750 to and from head 2830 using magnetic coupling. In other implementations, head 2830 may be releasably connected to insertion shaft 2750 and may be selectively released using other connection mechanisms and actuators.

Figure 45:
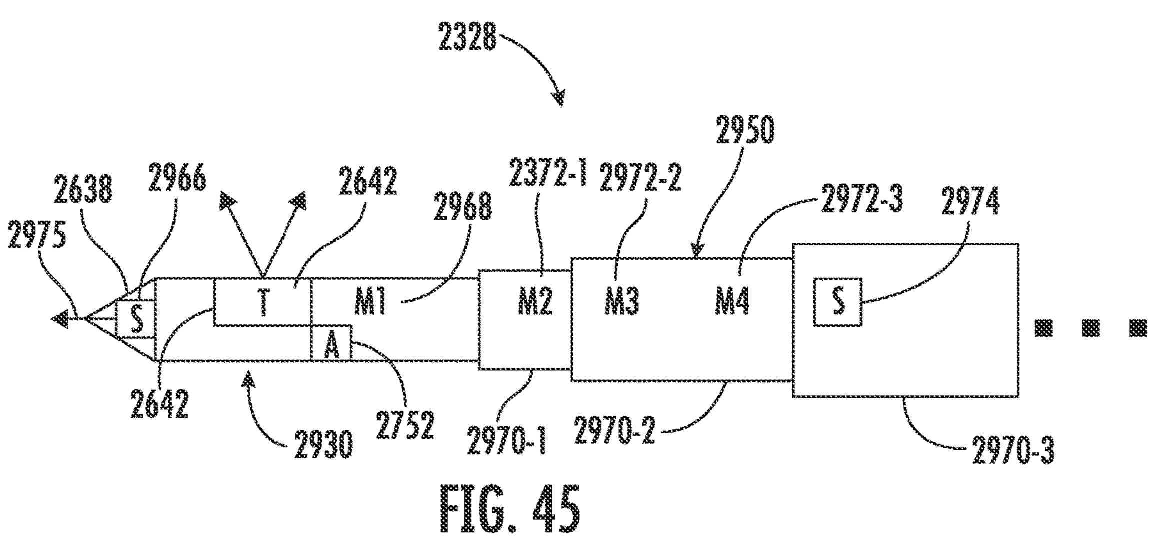
FIG. 45 is a diagram schematically illustrating portions of an example intra-organ ultrasound probe.

FIG. 45 is a diagram thematically tilting portions of an example intra-organ ultrasound probe 2928. FIG. 45 illustrates an example of how: (1) a sensor may be used to detect forces encountered during insertion of the head into an organ; (2) how an insertion shaft form from multiple segments may be used to extend and retract the head; and (3) how markers on the head and the insertion shaft may be used to facilitate remote detection of the positioning of the head and insertion shaft. Probe 2928 comprises head 2930 and insertion shaft 2950. Head 2330 is similar to head 2830 described above except that head 2930 additionally comprises sensor 2966 and marker (M1) 2968.

Sensor 2966 comprise a sensor positioned proximate to tip 2638 and configured to detect forces exerted upon tip 2638. Sensor 2966 outputs signals to a remote controller which may utilize such signals to determine the state or positioning of probe 2928 affected organ into which head 2930 is being inserted. For example, sensor 2966 may experience a high force level as tip 2638 is puncturing an organ during insertion, whereas following such insertion, the level of forces experienced by sensor 2966 may decline. In one such implementation, sensor 2966 comprises a strain gauge.

In other implementations, sensor 2966 may comprise an optical sensor vision behind a transparent portion of tip 2638. Sensor 2966 may be utilized to provide image signals such that a medical practitioner or automated control system may visually determine the position or state of head 2930. In particular implementations, sensor 2966 may comprise a camera. In yet other implementations, sensor 2966 may be omitted. Marker 2968 comprises an indicium formed in or upon head 2930 which is detectable by a sensor or probe external to the organ in which probe 2928 is positioned. In some implementations, marker 2968 may generate a sparkling artifact when imaged with ultrasound. Such markers may be composed of non-metallic materials that enhance the sparkling artifact. For example, in some implementations, marker 2968 may be formed from polymethyl methacrylate (PMMA), or an artificial uric acid which may be detected by an external ultrasound system such as an organ surface ultrasound probe similar to those described above. In yet other implementations, marker 2968 may be formed from other materials having similar characteristics. For example, marker 2968 may be formed using a metal detectable permanent marker.

Insertion shaft 2950 is releasably coupled to head 2930 and is configured to insert head 2930 through trocar 2326 and into the interior of an organ. Insertion shaft 2950 comprises segments 2970-1, 2970-2 and 2970-3 (collectively referred to as segments 2970), markers 2972-1, 2972-2, and 2972-3 (collectively referred to as markers 2972), and sensor 2974. Segments 2970 are movably coupled to one another. In the example illustrated, segments 2970 are telescopically connected to one another to extend and retract. Although insertion shaft 2950 is illustrated as including three such segments, in other implementations, insertion shaft 2950 may have other numbers of segments movably coupled to one another as indicated by the three ellipses.

Markers 2972 are each similar to marker 2968. Marker 2972-1 is located on segment 2970-1. Markers 2972-2 and 2972-3 are located at actually spaced apart locations along segment 2970-2. Markers 2972 facilitate the external detection of the positioning of each of segments 2970 relative to one another to facilitate the determination of the positioning of head 2930.

Sensor 2974 comprises sensing device configured to detect those forces exerted by segment 2970-2 in an axial direction towards segment 2970-3. Sensor 2974 is connected in a wired or wireless fashion to an external controller. External control may utilize such signals to determine any resistance experienced by further movement of head 2930 in the direction indicated by arrow 2975, such resistance indicating whether tip 2638 is currently puncturing or passing through tissue of an organ. In some implementations, sensor 2974 may comprise a pressure sensor. In some implementations, sensor 2974 may comprise a strain gauge. In yet other implementations, sensor 2974 may comprise other forms of sensors. In some implementations, sensor 2974 and/or markers 2972 may be omitted.

Figure 46:
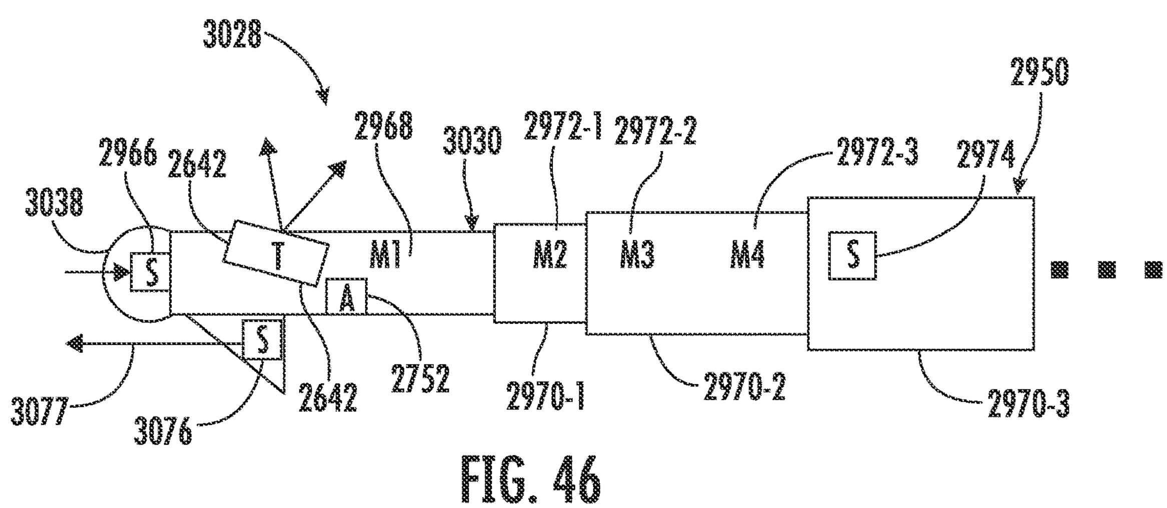
FIG. 46 is a diagram schematically illustrating portions of an example intra-organ ultrasound probe.

FIG. 46 is a diagram schematically illustrating portions of an example intra-organ ultrasound probe 3028. FIG. 46 illustrates an example of an alternative form for the tip of the probe head and the use of additional sensors for detecting the positioning of the probe head. Probe 3028 comprises head 3030 and insertion shaft 2950 (described above). Head 3030 is similar to head 3030 except that head 3030 comprise tip 3038 and sensor 3076.

Tip 3038 comprises a blunt tip, a tip having a rounded contour. In some implementations, tip 3038 is formed from an elastic, deformable and/or compressible material in this figure to transmit forces to sensor 2966 which senses resistance forces during insertion of head 3030 into an organ. In some implementations, tip 3038, serving as an active tip, may include additional or other types of sensors. For example, tip 3038 may additionally or alternatively comprise a sensor in the form of an elastography sensor, a torque sensor and/or a force sensing piezo sensor. In some implementations, tip 3038 may include a Doppler transducer or sensor for sensing when probe 3028 is moving towards a major vasculature or a forward blood vessel. In some implementations, tip 3038 may include a strain gauge serving as a sensor for detecting forces exerted upon tip 3038. In some implementations, tip 3038 may include electronic components of a tracking beacon.

Sensor 3076 is located along the exterior of head 3030 and is configured to sense in a forward direction as indicated by arrow 3077. In one implementation, sensor 3076 comprises an optical sensor, as a camera. Signals from sensor 3076 may be transmitted, wirelessly or in a wired fashion, to an external controller and/or display unit. Such signals may allow an automated system or a medical practitioner to move head 3030 through trocar 2326 (shown FIG. 27) and into an interior of an organ.

Figure 47:
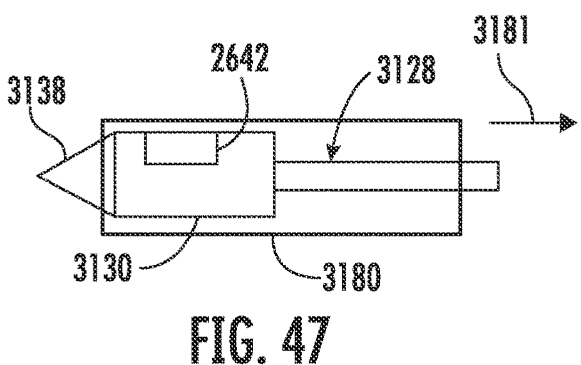
FIG. 47 is a diagram schematically illustrating portions of an example intra-organ ultrasound probe.

FIG. 47 is a diagram schematically illustrating the positioning of an example intra-organ ultrasound probe 3128 partially positioned within an outer sleeve 3180. FIG. 47 illustrated example of how an additional outer sleeve may be used to protect a majority of the transducer head during insertion into an organ, wherein the tip of the head may project from the sleeve and be used for puncturing the organ to pass into the organ. In the example illustrated, probe 3128 has a head 3130 determining at a pointed tip 3138 and supporting a sideways facing transducer 2642. Tip 3138 projects from sleeve 3180 while sleeve 3180 protects those remaining portions of head 3130, including transducer 2642. Once reaching the interior of the organ, sleeve 3180 may be retracted in the direction indicated by arrow 3181, exposing transducer 2642 for ultrasound sensing of the interior of the organ or associated tissue. In other implementations, the illustrated intra-organ ultrasound probe 3128 may be replaced with any of the above-described intra-organ ultrasound probes. In those implementations in which the tip of the head of the ultrasound probe is not pointed, a prior incision may be used to facilitate passing of the probe and the protective sleeve 3180 into the organ.

Although the present disclosure has been described with reference to example implementations, workers skilled in the art will recognize that changes may be made in form and detail without departing from the disclosure. For example, although different example implementations may have been described as including features providing various benefits, it is contemplated that the described features may be interchanged with one another or alternatively be combined with one another in the described example implementations or in other alternative implementations. Because the technology of the present disclosure is relatively complex, not all changes in the technology are foreseeable. The present disclosure described with reference to the example implementations and set forth in the following definitions is manifestly intended to be as broad as possible. For example, unless specifically otherwise noted, the definitions reciting a single particular element also encompass a plurality of such particular elements. The terms “first”, “second”, “third” and so on in the definitions merely distinguish different elements and, unless otherwise stated, are not to be specifically associated with a particular order or particular numbering of elements in the disclosure.

The present disclosure is directed to the features set forth in the following definitions.

1. An ultrasound sensing system comprising:
   - a first ultrasound probe comprising an organ surface ultrasound probe to connect to an exterior surface of an organ, the first ultrasound probe to be spaced from a region of interest of the organ by a first distance;
   - a second ultrasound probe to be spaced from the region of interest by a second distance less than the first distance; and
   - a processing unit to superimpose and register first ultrasound data from the organ surface ultrasound probe and second ultrasound data from the second ultrasound probe,
   - wherein the first ultrasound probe has a first field-of-view and wherein the second ultrasound probe has a second field-of-view less than the first field-of-view.
2. The system of definition 1, wherein the processing unit is part of a display unit and wherein the processing unit is to superimpose and register a first image based on the first ultrasound data based and a second image based on the second ultrasound data from the second ultrasound probe.
3. The system of definition 2, wherein the display unit is configured to depict an effector on the first and the second image.
4. The system of definition 2, wherein the first image has a first resolution and wherein the second image has a second resolution greater than the first resolution.
5. The system of definition 1, wherein the first ultrasound data and the second ultrasound data are superimposed and registered in real time by the processing unit.
6. The system of definition 1, wherein the second organ ultrasound probe is to connect to the exterior surface of the organ.
7. The system of definition 1, wherein the second ultrasound probe comprises an intra-organ ultrasound probe.

8. The system of definition 1, wherein the organ surface ultrasound probe emits mechanical waves at a first frequency and wherein the second ultrasound probe emits mechanical waves at a second frequency greater than the first frequency.
9. The system of definition 1, wherein the organ surface ultrasound probe has a first depth of view and wherein the second ultrasound probe has a second depth of view less than the first depth of view.
10. The system of definition 1, further comprising a trocar configured to receive the organ surface ultrasound probe.
11. The system of definition 1, wherein the organ surface ultrasound probe comprises:
 a transducer;
 a housing supporting the transducer; and
 an acoustic coupler for positioning between the transducer and the exterior surface of the organ.
12. The system of definition 11, wherein the transducer (50) comprises a conformable ultrasound array.
13. The system of definition 12 further comprising an actuator to move the conformable ultrasound array relative to the housing.
14. The system of definition 13, wherein conformable ultrasound array comprises:
 a flexible substrate supporting an array of transducer elements; and
 an acoustic coupler adjacent the transducer elements, wherein the actuator is configured to move the acoustic coupler from a retracted position in which the acoustic coupler is retracted within the housing and an extended position at least partially beyond the housing.
15. The system of definition 14, wherein the transducer elements extend on a first side of the flexible substrate and wherein the actuator comprises a fluid chamber on a second side of the flexible substrate opposite the first side.
16. The system of definition 14, wherein the acoustic coupler comprises a flexible chamber containing an acoustic coupling fluid and wherein the actuator comprises a fluid line connected to an interior of the flexible chamber to supply additional acoustic coupling fluid to expand the flexible chamber to the extended position.
17. The system of definition 16 further comprising a second actuator coupled to the flexible substrate to move the flexible substrate.
18. The system of definition 17 further comprising a third actuator coupled to the flexible substrate, wherein the second actuator and the third actuator are configured to independently move different respective portions of the flexible substrate.
19. The system of definition 11, wherein the actuator is configured to move the acoustic coupler from a retracted position in which the acoustic coupler is retracted within the housing and an extended position at least partially beyond the housing.
20. The system of definition 11, wherein the actuator is configured to move the transducer relative to the housing.
21. The system of definition 20, wherein the actuator is configured to reorient the transducer relative to the housing.
22. The system of definition 14, wherein the transducer is at least partially immersed within the acoustic coupler.
23. The system of definition 14, wherein the transducer abuts an exterior of the acoustic coupler.
24. The system of definition 14, wherein the acoustic coupler has an exterior coated with an adhesive for bonding to the organ.
25. The system of definition 14, wherein the housing comprises grippers to grip the exterior surface of the organ.
26. The system of definition 25, wherein the grippers are configured to grip the exterior surface of the organ via suction.
27. The system of definition 26, wherein the grippers comprise a vacuum source to selectively generate suction.
28. The system of definition 14 further comprising an organ conformable panel for being secured to the exterior surface of the organ, the organ conformable panel comprising an aperture configured to receive the acoustic coupler.
29. The system of definition 5, wherein the housing and the organ conformable panel are configured to releasably connect to one another.
30. The system of definition 29, wherein the housing comprises couplers configured to be releasably connect to the organ conformable panel.
31. The system of definition 30, when the couplers are deployable from a retracted state to an extended state.
32. The system of definition 1, wherein the organ surface ultrasound probe (928) comprises:
 a transducer; and
 a head having a housing supporting the transducer, the head having a hydrophilic exterior surface.
33. The system of definition 32, wherein the head extends along an axis, terminating at a tip and wherein the transducer is configured to sense in a direction transverse to the axis.
34. The system of definition 33, wherein the tip is blunt.
35. The system of definition 1, wherein the organ surface ultrasound probe comprises:
 an insertion shaft;
 a head supporting a transducer, the head being removably coupled to the insertion shaft for separation from the insertion shaft while the head is connected to the exterior surface of the organ.
36. The system of definition 35, wherein the organ surface ultrasound probe comprises an insertion shaft for insertion through a trocar, the insertion shaft comprising:
 a first segment coupled to the transducer support;
 a second segment pivotably coupled to the first segment; and
 an actuator to selectively pivot the first segment and the second segment relative to one another.
37. The system of definition 36 further comprising electrical lines connected to the transducer and extending along and supported by the insertion shaft.
38. The system of definition 37, wherein the electrical lines are removably coupled to the insertion shaft such that the insertion shaft is withdrawable while connected to the transducer and while the head remains in contact with the exterior surface of the organ.
39. The system of definition 1, wherein the organ surface ultrasound probe comprises:
 an insertion shaft;
 a head supporting a transducer, the head being pivotably coupled to the insertion shaft.
40. The system of definition 1, wherein intra-organ ultrasound probe comprises:
 an insertion shaft; and a head coupled to an end portion of the insertion shaft and supporting a transducer.

41. The system of definition 40, wherein the intra-organ ultrasound probe further comprises an actuator extending along the insertion shaft and coupled to the head for selectively pivoting the head relative to the insertion shaft.

42. The system of definition 41, wherein the head is removably coupled to the insertion shaft for separation from the insertion shaft while within the organ.

43. The system of definition 42, wherein the head is magnetically coupled to the insertion shaft.

44. The system of definition 39, wherein the insertion shaft comprises:

a flexible guide sheath; and a wire extending through and along the flexible guide sheath to the head.

45. The system of definition 39, wherein the insertion shaft has an adjustable length.

46. The system of definition 45, wherein the insertion shaft is telescopic.

47. The system of definition 39, wherein the insertion shaft comprises a plurality of segments, each of the segments being movable relative to other segments.

48. The system of definition 39, wherein the insertion shaft comprises a plurality of markings being detected by the organ surface ultrasound probe.

49. The system of definition 39, wherein the intra-organ ultrasound probe has a tip, the tip comprising a sensor to detect engagement of the tip with soft tissue.

50. The system of definition 39, wherein the insertion shaft is telescopic and wherein the insertion shaft comprises a sensor configured to detect forces resisting telescopic extension of the insertion shaft.

51. The system of definition 39, wherein the head comprises a tip having a sharp transparent lens for soft tissue puncturing and a forward sensor rearward the sharp lens and having a field of view through the transparent lens.

52. The system of definition 39, wherein the insertion shaft extends along an axis, terminating at a tip, and wherein the transducer is configured to sense in a direction transverse to the axis.

53. The system of definition 39, wherein the head comprises a tip that is blunt.

54. The system of definition 39, wherein the head comprises a tip that is sharp for soft tissue puncturing.

55. The system of definition 39, wherein the head comprises an elastomeric the tip.

56. An intra-organ ultrasound probe comprising:

an insertion shaft; and a head coupled to an end portion of the insertion shaft and supporting a transducer.

57. The intra-organ ultrasound probe of definition 56, wherein the intra-organ ultrasound probe further comprises an actuator extending along the insertion shaft and coupled to the head for selectively pivoting the head relative to the insertion shaft.

58. The intra-organ ultrasound probe of definition 56, wherein the transducer comprises a deformable transducer array.

59 The intra-organ ultrasound probe of definition 56, wherein the head is removably coupled to the insertion shaft for separation from the insertion shaft while within the organ.

60. The intra-organ ultrasound probe of definition 59, wherein the head is magnetically coupled to the insertion shaft.

61. The intra-organ ultrasound probe of definition 56, wherein the insertion shaft comprises:

a flexible guide sheath; and a wire extending through and along the flexible guide sheath to the head.

62. The intra-organ ultrasound probe of definition 56, wherein the insertion shaft has an adjustable length.

63. The intra-organ ultrasound probe of definition 62, wherein the insertion shaft is telescopic.

64. The intra-organ ultrasound probe of definition 56, wherein the insertion shaft comprises a plurality of segments, each of the segments being movable relative to other segments.

65. The intra-organ ultrasound probe of definition 56, wherein the insertion shaft comprises a plurality of markings for being detected by the organ surface ultrasound probe.

66. The intra-organ ultrasound probe of definition 56, wherein the intra-organ ultrasound probe has a tip, the tip comprising a sensor to detect engagement of the tip with soft tissue.

67. The intra-organ ultrasound probe of definition 66, wherein the insertion shaft is telescopic and wherein the sensor is configured to detect forces resisting telescopic extension of the insertion shaft.

68. The intra-organ ultrasound probe of definition 66, wherein the tip comprise a sharp transparent lens for soft tissue puncturing and a forward sensor rearward the sharp lens and having a field of view through the transparent lens.

69. The intra-organ ultrasound probe of definition 66, wherein head extends along an axis, terminating at a tip, and wherein the transducer is configured to sense in a direction transverse to the axis.

70. The intra-organ ultrasound probe of definition 69, wherein the tip is blunt.

71. The intra-organ ultrasound probe of definition 69, wherein the tip is sharp for soft tissue puncturing.

72. The intra-organ ultrasound probe of definition 69, wherein the tip is elastomeric.

73. An organ surface ultrasound probe comprising:

a head comprising:

a transducer;

a housing supporting the transducer;

an acoustic coupler for positioning between the transducer and the exterior surface of the organ; and an actuator to move the transducer relative to the housing.

74. The organ surface ultrasound probe of definition 73, wherein the transducer (50) comprises a conformable ultrasound array.

75. The organ surface ultrasound probe of definition 74, wherein conformable ultrasound array comprises:

a flexible substrate supporting an array of transducer elements; and an acoustic coupler adjacent the transducer elements, wherein the actuator is configured to move the acoustic coupler from a retracted position in which the acoustic coupler is retracted within the housing and an extended position at least partially beyond the housing.

76. The organ surface ultrasound probe of definition 75, wherein the transducer elements extend on a first side of the flexible substrate and wherein the actuator comprises a fluid chamber on a second side of the flexible substrate opposite the first side.

77. The organ surface ultrasound probe of definition 75, wherein the acoustic coupler comprises a flexible chamber containing an acoustic coupling fluid and wherein the actuator comprises a fluid line connected to an interior of the flexible chamber to supply additional acoustic coupling fluid to expand the flexible chamber to the extended position.

78. The organ surface ultrasound probe of definition 77 further comprising a second actuator coupled to the flexible substrate to move the flexible substrate.

79. The organ surface ultrasound probe of definition 78 further comprising a third actuator coupled to the flexible substrate, wherein the second actuator and the third actuator are configured to independently move different respective portions of the flexible substrate.

80. The organ surface ultrasound probe of definition 73, wherein the actuator is configured to move the acoustic coupler from a retracted position in which the acoustic coupler is retracted within the housing and an extended position at least partially beyond the housing.

81. The organ surface ultrasound probe of definition 73, wherein the actuator is configured to move the transducer relative to the housing.

82. The organ surface ultrasound probe of definition 81, wherein the actuator is configured to reorient the transducer relative to the housing.

83. The organ surface ultrasound probe of definition 73, wherein the transducer is at least partially immersed within the acoustic coupler.

84. The organ surface ultrasound probe of definition 73, wherein the transducer abuts an exterior of the acoustic coupler.

85. The organ surface ultrasound probe of definition 73, wherein the acoustic coupler has an exterior coated with an adhesive for bonding to the organ.

86. The organ surface ultrasound probe of definition 73, wherein the housing comprises grippers to grip the exterior surface of the organ.

87. The organ surface ultrasound probe of definition 86, wherein the grippers are configured to grip the exterior surface of the organ via suction.

88. The organ surface ultrasound probe of definition 87, wherein the grippers comprise a vacuum source to selectively generate suction.

89. The organ surface ultrasound probe of definition 73 further comprising an organ conformable panel for being secured to the exterior surface of the organ, the organ conformable panel comprising an aperture configured to receive the acoustic coupler.

90. The organ surface ultrasound probe of definition 89, wherein the housing and the organ conformable panel are configured to releasably connect to one another.

91. The organ surface ultrasound probe of definition 89, wherein the housing comprises couplers configured to be releasably connect to the organ conformable panel.

92. The organ surface ultrasound probe of definition 91, when the couplers are deployable from a retracted state to an extended state.

93. The organ surface ultrasound probe of definition 73, wherein the head has a hydrophilic exterior surface.

94. The organ surface ultrasound probe of definition 73, wherein the head extends along an axis, terminating at a tip and wherein the transducer is configured to sense in a direction transverse to the axis.

95. The organ surface ultrasound probe of definition 94, wherein the tip is blunt.

96. The organ surface ultrasound probe of definition 73, wherein the organ surface ultrasound probe comprises:
an insertion shaft, wherein the head is removably coupled to the insertion shaft for separation from the insertion shaft while the head is connected to the exterior surface of the organ.

97. The organ surface ultrasound probe of definition 73, wherein the organ surface ultrasound probe comprises an insertion shaft for insertion through a trocar, the insertion shaft comprising:
a first segment coupled to the head;
a second segment pivotably coupled to the first segment; and
an actuator to selectively pivot the first segment and the second segment relative to one another.

98. The organ surface ultrasound probe of definition 97 further comprising electrical lines connected to the transducer and extending along and supported by the insertion shaft.

99. The organ surface ultrasound probe of definition 98, wherein the electrical lines are removably coupled to the insertion shaft such that the insertion shaft is withdrawable while connected to the transducer and while the head remains in contact with the exterior surface of the organ.

100. The organ surface ultrasound probe of definition 73, wherein the organ surface ultrasound probe comprises:
an insertion shaft, wherein the head is pivotably coupled to the insertion shaft.

101. The organ surface ultrasound probe of definition 73, wherein the acoustic coupler comprises a chamber containing an acoustic coupling fluid and wherein the organ surface ultrasound probe further comprises:
a pump fluidly coupled to an interior of the chamber to circulate the acoustic coupling fluid across the transducer.

102. The organ surface ultrasound probe of definition 101, wherein the chamber has an inlet port through which the pump moves the acoustic coupling fluid circulates into the interior and an outlet port through which the acoustic coupling fluid circulates out of the interior.

103. The organ surface ultrasound probe of definition 102 further comprising a controller, wherein the controller is configured to output control signals operating the transducer in a first mode and a second mode different than the first mode and wherein the controller is configured to output control signals causing the pump to circulate the acoustic coupling fluid across the transducer at a first rate during operation of the transducer in the first mode and at a second rate, different than the first rate, during operation of the transducer in the second mode.

104. The organ surface ultrasound probe of definition 103, wherein the transducer emits a first amount of heat in the first mode and a second amount of heat, greater than the first amount of heat, in the second mode and wherein the second rate is greater than the first rate.

105. The organ surface ultrasound probe of definition 103, wherein the controller is configured to output control signals that focus the transducer on a first portion of an organ of a patient during the first mode and that focus the transducer on a second portion of the organ of the patient during the second mode.

106. The organ surface ultrasound probe of definition 105, wherein the second portion of the organ of the patient consists of tissue to be removed.

107. The organ surface ultrasound probe of definition 102 further comprising:
a temperature sensor to output temperature signals; and
a controller, wherein the controller outputs control that cause the pump to circulate the acoustic coupling fluid at different rates based upon the temperature signals.

108. The organ surface ultrasound probe of definition 102 further comprising a passive heat extractor, wherein the pump is configured to circulate fluid across the passive heat extractor.

109. The organ surface ultrasound probe of definition 102 further comprising:
an active heat extractor; and
a controller to output control signals to operate the active heat extractor in different heat extraction states.

110. The organ surface ultrasound probe of definition 109, wherein the controller is configured to output control signals causing the transducer to operate in a first mode and a second mode different than the first mode and wherein the controller is configured to output first control signals operating the active heat extractor in a first heat extraction state during the first mode and a second heat extraction state, different than the first heat extraction state during the second mode.

111. The organ surface ultrasound probe of definition 109 further comprising a temperature sensor to output temperature signals, wherein the controller is configured up with the control signals to differently operate the active heat extractor based upon the temperature signals.

112. The organ surface ultrasound probe of definition 102 further comprising:
a flow meter to output flow signals; and
a controller configured to output control signals controlling operation of the pump based upon the flow signals.

113. The organ surface ultrasound probe of definition 102, wherein the chamber comprises a flexible bladder, the organ surface ultrasound probe further comprising a controller to output control signals controlling the pump, wherein the controller is configured to output first control signals causing the pump to inflate the flexible bladder with the acoustic coupling medium to an extended state extending beyond the housing into contact with an organ of a patient to space the transducer from the organ by distance and second control signals causing the pump to deflate the flexible bladder to a retracted state within the housing.

114. The organ surface ultrasound probe of definition 113, wherein the controller is configured to output third control signals causing the pump to inflate the flexible bladder with the acoustic coupling medium to a second extended state beyond the housing into contact with the organ of the patient to space the transducer from the organ by a second distance different than the first distance.

115. The organ surface ultrasound probe of definition 113 further comprising a reservoir containing the acoustic coupling medium, wherein the pump is configured to move the acoustic coupling medium from the bladder into the reservoir during deflation of the flexible bladder and is configured to move the acoustic coupling medium from the reservoir and into the flexible bladder during inflation of the flexible bladder.

116. An organ surface ultrasound probe comprising:
a head comprising:
a transducer;
a housing supporting the transducer;
a flexible bladder containing an acoustic coupling medium for positioning between the transducer and the exterior surface of the organ; and
a pump; and
a controller to output control signals causing the pump to inflate the bladder with the acoustic coupling medium from a first extended state, extending beyond the housing into contact with an organ surface of a patient to space the transducer from the organ surface by first distance, to a second extended state extending beyond the housing into contact with the organ surface of the patient to space the transducer from the organ surface by second distance different than the first distance.

117. The organ surface ultrasound probe of definition 116 further comprising an actuator to move transducer relative to the housing.

118. The organ surface ultrasound probe of definition 116, wherein the pump is fluidly coupled to an interior of the flexible bladder to circulate fluid through the flexible bladder.

119. An organ surface ultrasound probe comprising:
a head comprising:
a transducer having a front sensing face and a rear face;
a housing supporting the transducer;
a fluid chamber containing fluid adjacent the transducer; and
a pump to selectively supply fluid to and draw fluid from an interior of the fluid chamber.

120. The surface ultrasound probe of definition 119, wherein the fluid comprises a fluid coupling medium and wherein the interior of the fluid chamber extends adjacent the front sensing face of the transducer.

121. The surface ultrasound probe definition 120, wherein the fluid chamber has an inlet port and an outlet port and wherein the pump is configured to circulate the fluid across the front sensing face of the transducer.

122. The surface ultrasound probe of definition 119, wherein the interior the fluid chamber extends adjacent the rear face of the transducer.

123. The surface ultrasound probe of definition 122, wherein the fluid chamber has an inlet port and an outlet port and wherein the pump is configured to circulate the fluid across the rear face of the transducer.

124. The organ surface ultrasound probe of definition 119 further comprising a controller, wherein the controller is configured to output control signals operating the transducer in a first mode and a second mode different than the first mode and wherein the controller is configured to output control signals causing the pump to circulate the acoustic coupling fluid across the transducer at a first rate during operation of the transducer in the first mode and at a second rate, different than the first rate, during operation of the transducer in the second mode.

125. The organ surface ultrasound probe of definition 124, wherein the transducer emits a first amount of heat in the first mode and a second amount of heat, greater than the first amount of heat, in the second mode and wherein the second rate is greater than the first rate.

126. The organ surface ultrasound probe of definition 124, wherein the controller is configured to output control signals that focus the transducer on a first portion of an organ of a patient during the first mode and that focus the transducer on a second portion of the organ of the patient during the second mode.

127. The organ surface ultrasound probe of definition 126, wherein the second portion of the organ of the patient consists of tissue to be removed.

128. The organ surface ultrasound probe of definition 119 further comprising:
- a temperature sensor to output temperature signals; and
- a controller, wherein the controller outputs control that cause the pump to circulate the acoustic coupling fluid at different rates based upon the temperature signals.

129. The organ surface ultrasound probe of definition 119 further comprising a passive heat extractor, wherein the pump is configured to circulate fluid across the passive heat extractor.

130. The organ surface ultrasound probe of definition 119 further comprising:
- an active heat extractor; and
- a controller to output control signals to operate the active heat extractor in different heat extraction states.

131. The organ surface ultrasound probe of definition 130, wherein the controller is configured to output control signals causing the transducer to operate in a first mode and a second mode different than the first mode and wherein the controller is configured to output first control signals operating the active heat extractor in a first heat extraction state during the first mode and a second heat extraction state, different than the first heat extraction state during the second mode.

132. The organ surface ultrasound probe of definition 130 further comprising a temperature sensor to output temperature signals, wherein the controller is configured up with the control signals to differently operate the active heat extractor based upon the temperature signals.

133. The organ surface ultrasound probe of definition 119 further comprising:
- a flow meter to output flow signals; and
- a controller configured to output control signals controlling operation of the pump based upon the flow signals.

134. An organ surface ultrasound probe comprising:
- a transducer; and
- a controller configured to:
  - output first control signals operating the transducer in a first mode with an acoustic field emission focused on an organ of a patient and having a first output exposure level;
  - identify tissue associated with the organ for removal based upon signals from the transducer when operating in the first mode; and
  - output second control signals operating the transducer in a second mode within acoustic field emission focused on the identified tissue having a second output exposure level greater than the first output exposure level.

135. The organ surface ultrasound probe of definition 134, wherein the first output exposure level complies with Food and Drug Administration (FDA) acoustic output exposure level guidelines and wherein the second output exposure level exceeds the FDA acoustic output exposure level guidelines.

136. The organ surface ultrasound probe of definition 134, wherein the first output exposure level is less than or equal to 190 W/cm$^2$ and wherein the second output exposure level exceeds 190 W/cm$^2$.

137. The organ surface ultrasound probe of definition 134, wherein the first output exposure level is less than or equal to 720 mW/cm$^2$ and wherein the second output exposure level exceeds 720 mW/cm$^2$.

138. The organ surface ultrasound probe of definition 134, wherein the transducer as a front sensing face and a rear face and wherein the organ surface ultrasound probe further comprises:
- a housing supporting the transducer;
- a fluid chamber containing fluid adjacent the transducer; and
- a pump to circulate fluid through an interior of the fluid chamber.

139. The organ surface ultrasound probe of definition 138, wherein the controller is configured output control signals causing the pump to circulate the fluid through the interior of the fluid chamber at a first rate in response to the first control signals and causing the pump to circulate the fluid through the interior of the fluid chamber at a second rate, greater than the first rate, in response to the second control signals.

140. The organ surface ultrasound probe of definition 139, wherein the interior the fluid chamber extends adjacent the front sensing face of the transducer and wherein the fluid comprises an acoustic coupling medium.

141. The organ surface ultrasound probe of definition 140, wherein the fluid chamber is at least partially bound by a flexible bladder.

142. The organ surface ultrasound probe of definition 138 further comprising:
- an active heat extractor, wherein the controller is configured to output control signals to operate the active heat extractor in different heat extraction states and wherein the controller is configured to output first control signals operating the active heat extractor in a first heat extraction state during the first mode and a second heat extraction state, different than the first heat extraction state, during the second mode.

143. A method comprising:
- operating a transducer in a first mode with an acoustic field emission focused on an organ of a patient and having a first output exposure level;
- identifying tissue associated with the organ for removal based upon signals from the transducer when operating in the first mode; and
- operating the transducer in a second mode with an acoustic field emission focused on the identified tissue having a second output exposure level greater than the first output exposure level.

144. The method of definition 143, wherein the first output exposure level complies with Food and Drug Administration (FDA) acoustic output exposure level guidelines and wherein the second output exposure level exceeds the FDA acoustic output exposure level guidelines.

145. The method of definition 143, wherein the first output exposure level is less than or equal to 190 W/cm$^2$ and wherein the second output exposure level exceeds 190 W/cm$^2$.

146. The method of definition 143, wherein the first output exposure level is less than or equal to 720 $mW/cm^2$ and wherein the second output exposure level exceeds 720 $mW/cm^2$.

147. A method comprising:
identifying tissue associated with an organ for surgical removal; and
operating an ultrasound transducer with an acoustic field emission focused on the identified tissue having an output exposure level exceeding FDA acoustic output exposure level guidelines for the organ.

148. The method of definition 147 wherein the output exposure level exceeds 190 $W/cm^2$.

149. The method of definition 147 and wherein the second output exposure level exceeds 720 $mW/cm^2$.

150. A method comprising:
receiving signals from an ultrasound transducer element over time; and
determining a position of the ultrasound transducer element based upon the signals.

What is claimed is:

1. An organ surface ultrasound probe comprising:
a head comprising:
a transducer;
a housing supporting the transducer; and
a flexible bladder containing an acoustic coupling medium for positioning between the transducer and an exterior surface of an organ; and
a pump; and
a controller to output control signals causing the pump to inflate the flexible bladder to different inflation states, wherein the different inflation states comprise a first inflation state while the flexible bladder is fully retracted within the housing and a second inflation state while the flexible bladder protrudes from the housing, wherein the transducer is external to the flexible bladder.

2. The organ surface ultrasound probe of claim 1 further comprising an actuator to move the transducer relative to the housing.

3. The organ surface ultrasound probe of claim 1, wherein the pump is fluidly coupled to an interior of the flexible bladder to circulate fluid through the flexible bladder.

4. The organ surface ultrasound probe of claim 1, wherein the transducer is contained within the flexible bladder.

5. The organ surface ultrasound probe of claim 1, wherein the head comprises:
a first retractable and extendable wing supporting the transducer and the flexible bladder, wherein the first retractable and extendable wing is configured to pivot at least 90 degrees from a retracted position to an extended position; and
a second retractable and extendable wing supporting a second transducer and a second flexible bladder containing a second acoustic coupling medium, wherein the second retractable and extendable wing is configured to pivot at least 90 degrees from a retracted position to an extended position.

6. The organ surface ultrasound probe of claim 1, wherein the flexible bladder comprises independently inflatable compartments.

7. The organ surface ultrasound probe of claim 6, wherein the independently inflatable compartments comprise a first compartment, a second compartment and a third compartment between the first compartment and the second compartment and wherein the transducer is adjacent the third compartment with the third compartment containing the acoustic coupling medium which is sandwiched between the transducer and the exterior surface of the organ.

8. The organ surface ultrasound probe of claim 1, wherein the transducer is adjacent to an external flexible surface of the flexible bladder and wherein the flexible bladder is configured to be sandwiched between the transducer and the exterior surface of the organ.

9. An organ surface ultrasound probe comprising:
a head comprising:
a transducer;
a housing supporting the transducer; and
a flexible bladder containing an acoustic coupling medium for positioning between the transducer and an exterior surface of an organ such that the flexible bladder contacts the exterior surface of the organ to acoustically couple the transducer to the exterior surface of the organ, wherein the transducer is external to the bladder;
a pump; and
a controller to output control signals causing the pump to inflate the flexible bladder to different inflation states, wherein the flexible bladder comprises independently inflatable compartments.

* * * * *